US008333970B2

(12) United States Patent
Aukerman et al.

(10) Patent No.: US 8,333,970 B2
(45) Date of Patent: Dec. 18, 2012

(54) METHODS OF MONITORING THE EFFICACY OF ANTI-CD40 ANTIBODIES IN TREATING A SUBJECT HAVING AN INFLAMMATORY OR AUTOIMMUNE DISEASE

(75) Inventors: Sharon Lea Aukerman, Moraga, CA (US); Bahija Jallal, Emeryville, CA (US); Mohammad Luqman, Danville, CA (US)

(73) Assignees: Novartis AG, Basel (CH); Xoma Technology Ltd., Berkeley, CA (US)

(*) Notice: Subject to any disclaimer, the term of this patent is extended or adjusted under 35 U.S.C. 154(b) by 979 days.

(21) Appl. No.: 11/914,710

(22) PCT Filed: May 18, 2006

(86) PCT No.: PCT/US2006/019325
§ 371 (c)(1),
(2), (4) Date: Jul. 11, 2008

(87) PCT Pub. No.: WO2006/125117
PCT Pub. Date: Nov. 23, 2006

(65) Prior Publication Data
US 2008/0274118 A1    Nov. 6, 2008

Related U.S. Application Data

(60) Provisional application No. 60/682,575, filed on May 18, 2005, provisional application No. 60/749,336, filed on Dec. 9, 2005.

(51) Int. Cl.
*A61K 39/395* (2006.01)
*C12Q 1/00* (2006.01)
*C12Q 1/68* (2006.01)
*G01N 33/53* (2006.01)

(52) U.S. Cl. ........... 424/144.1; 424/143.1; 424/153.1; 424/173.1; 435/4; 435/6.1; 435/7.1; 435/7.2

(58) Field of Classification Search .......... None
See application file for complete search history.

(56) References Cited

U.S. PATENT DOCUMENTS

| | | | |
|---|---|---|---|
| 6,444,233 B1* | 9/2002 | Arntzen et al. | 424/725 |
| 7,063,845 B2* | 6/2006 | Mikayama et al. | 424/153.1 |
| 7,288,252 B2* | 10/2007 | Chu et al. | 424/153.1 |
| 2002/0009444 A1 | 1/2002 | Grillo-Lopez | |
| 2003/0211100 A1 | 11/2003 | Bedian et al. | |
| 2004/0219616 A1* | 11/2004 | Seery et al. | 435/7.23 |
| 2007/0254850 A1* | 11/2007 | Lieberman et al. | 514/44 |
| 2007/0292439 A1* | 12/2007 | Luqman | 424/172.1 |
| 2008/0254026 A1* | 10/2008 | Long et al. | 424/133.1 |
| 2009/0215895 A1* | 8/2009 | Ferrante et al. | 514/560 |

FOREIGN PATENT DOCUMENTS

| | | |
|---|---|---|
| WO | WO 99/42075 | 8/1999 |
| WO | WO 01/80884 A1 | 11/2001 |
| WO | WO 02/28481 A2 | 4/2002 |
| WO | WO 03/040170 A2 | 5/2003 |
| WO | WO 2005/044306 A2 | 5/2005 |

OTHER PUBLICATIONS

Biomarkers Definitions Working Groups., Clin. Pharmacol. Ther. 69: 89-95, 2001.*
Cherukuri et al., Blood 106, 11, Part 1: p. 832A, Abstract 2965, Nov. 16, 2005.*
Alexandroff, et al., "Role for CD40-CD40 ligand interactions in the immune response to solid tumours," *Molecular Immunology*, 2000, pp. 515-526, vol. 37.
Kwekkeboom et al., "CD40 plays an essential role in the activation of human B cells by murine EL4B5 cells," *Immunology*, 1993, pp. 439-444, vol. 79(3).
Baker, et al., "Modulation of Life and Death by the TNF Receptor Superfamily," *Oncogene*, 1998, pp. 3261-3270, vol. 17.
Boon et al., "Prevention of Experimental Autoimmune Encephalomyelitis in the Common Marmoset (*Callithrix jacchus*) Using a Chimeric Antagonist Monoclonal Antibody Against Human CD40 Is Associated with Alterered B Cell Responses," *The American Association of Immunologists*, 2001, pp. 2942-2949, vol. 167.
Brams et al., "A Humanized Anti-Human CD154 Monoclonal Antibody Blocks CD154-CD40 Mediated Human B Cell Activation," *Internationl Immunopharmacology*, 2001, pp. 277-294.
Mohan et al., "Interaction Between CD40 and Its Ligand gp39 in the Development of Murine Lupus Nephritis," *The Journal of Immunology*, 1995, pp. 1470-1480, vol. 154.
Howard et al., "Mechanisms of Immunotherapeutic Intervention by Anti-CD40L (CD154) Antibody in an Animal Model of Multiple Sclerosis," *The Journal of Clinical Investigation*, 1999, pp. 281-290, vol. 103, No. 2.
Xu et al., "The Role of CD40-CD154 Interaction in Cell Immunoregulation," *Journal of Biomedical Science*, 2004, pp. 426-438, vol. 11.
Hase, H., et al., "Roles of Co-stimulatory Molecules: Mechanism of Anti-apoptotic Effect on B Cell Apoptosis by CD27 and CD40 Signaling," *Clin. Immunol.*, 2003, vol. 40, No. 5, pp. 487-493.
Yasui, T., et al., "Signal transduction and gene—CD40 Signal," *Genetic Medicine*, 1999, vol. 3, No. 2, pp. 64-69.

* cited by examiner

*Primary Examiner* — Phillip Gambel
(74) *Attorney, Agent, or Firm* — Alston & Bird LLP

(57) ABSTRACT

Methods for identifying subjects having an inflammatory disease and/or autoimmune disease that will benefit from anti-CD40 therapeutic agents that modulate CD40L-mediated CD40 signaling are provided. The methods comprise the use of biomarkers of cellular apoptosis, cell proliferation and survival, and CD40 signaling pathways to monitor ex vivo response to one or more anti-CD40 therapeutic agents of interest that modulate CD40 signaling on CD40-expressing cells. The ex vivo prognostic assays can be used alone or in conjunction with other prognostic assays to identify candidate subjects who will benefit from treatment with anti-CD40 therapeutic agents. Methods of the invention also comprise the use of these biomarkers to monitor in vivo efficacy of treatment with an anti-CD40 therapeutic agent.

51 Claims, 1 Drawing Sheet

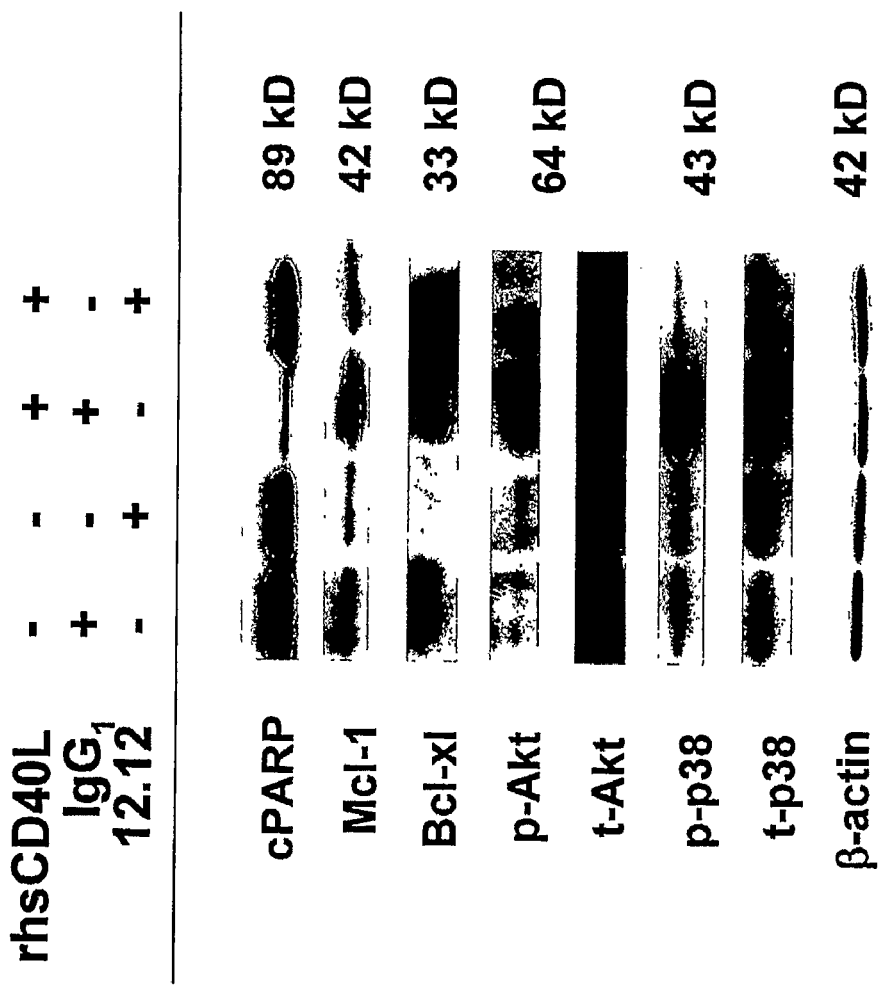

METHODS OF MONITORING THE EFFICACY OF ANTI-CD40 ANTIBODIES IN TREATING A SUBJECT HAVING AN INFLAMMATORY OR AUTOIMMUNE DISEASE

CROSS-REFERENCE TO RELATED APPLICATIONS

This application is a national stage of International Patent Application No. PCT/US2006/019325, filed May 18, 2006, which claims the benefit of U.S. Provisional Application No. 60/682,575, filed May 18, 2005, and U.S. Provisional Application No. 60/749,336, filed Dec. 9, 2005.

FIELD OF THE INVENTION

The invention relates to the field of diagnostic and prognostic medicine, more particularly to methods for determining efficacy of therapeutic agents in treatment of diseases having an autoimmune and/or inflammatory component that is associated with aberrant CD40 signaling.

BACKGROUND OF THE INVENTION

Many members of the tumor necrosis factor (TNF) family of ligands and their corresponding receptors regulate growth of normal cells by inducing apoptosis or enhancing cell survival and proliferation. It is this balance between apoptotic signals and survival and proliferation signals that maintains normal cellular homeostasis. At least 26 TNF family receptors and 18 TNF family ligands have been identified to date. The biologically active forms of both the receptors and ligands are self-assembled protein trimers. Transmembrane and soluble forms of both the receptors and ligands have been identified. Though the intracellular domains of the receptors share no sequence homology, their extracellular domains comprise 40-amino-acid, cysteine-rich repeats. Their cytoplasmic tails signal by interacting with two major groups of intracellular proteins: TNF receptor-associated factors (TRAFs) and death domain (DD)-containing proteins. Interaction between at least six human TRAFs and TRAF-binding sites on the cytoplasmic tail of some of these receptors initiates several signaling pathways, including AKT (the serine/threonine kinase referred to as protein kinase B or PKB), nuclear factor-κB (NF-κB), and mitogen-activated protein kinases (MAPK). See, for example, the review by Younes and Kadin (2003) *J. Clin. Oncol.* 18:3526-3534.

The TNF family receptor member CD40 is a 50-55 kDa cell-surface antigen present on the surface of both normal and neoplastic human B cells, dendritic cells, monocytes, macrophages, CD8$^+$ T cells, endothelial cells, and monocytic and epithelial cells. The CD40 antigen is also expressed on activated T cells, activated platelets, inflamed vascular smooth muscle cells, eosinophils, synovial membranes in rheumatoid arthritis, dermal fibroblasts, and other non-lymphoid cell types. Depending on the type of cell expressing CD40, ligation can induce intercellular adhesion, differentiation, activation, and proliferation. For example, binding of CD40 to its cognate ligand, CD40L (also designated CD154), stimulates B-cell proliferation and differentiation into plasma cells, antibody production, isotype switching, and B-cell memory generation. During B-cell differentiation, CD40 is expressed on pre-B cells but lost upon differentiation into plasma cells.

The CD40 ligand (CD40L), also known as CD154, is a 32-33 kDa transmembrane protein that also exists in two smaller biologically active soluble forms, 18 kDa and 31 kDa, respectively (Graf et al. (1995) *Eur. J. Immunol.* 25:1749-1754; Mazzei et al. (1995) *J. Biol. Chem.* 270:7025-7028; Pietravalle et al. (1996) *J. Biol. Chem.* 271:5965-5967). CD40L is expressed on activated, but not resting, CD4$^+$ T-helper cells (Lane et al. (1992) *Eur. J. Immunol.* 22:2573-2578; Spriggs et al. (1992) *J. Exp. Med.* 176:1543-1550; and Roy et al. (1993) *J. Immunol.* 151:1-14). Both CD40 and CD40L have been cloned and characterized (Stamenkovi et al. (1989) *EMBO J.* 8:1403-1410; Armitage et al. (1992) *Nature* 357:80-82; Lederman et al. (1992) *J. Exp. Med.* 175: 1091-1101; and Hollenbaugh et al. (1992) *EMBO J.* 11:4313-4321). See also U.S. Pat. No. 5,945,513, describing human CD40L. Cells transfected with the CD40L gene and expressing the CD40L protein on their surface can trigger B-cell proliferation, and together with other stimulatory signals, can induce antibody production (Armitage et al. (1992) supra; and U.S. Pat. No. 5,945,513). Patients with autoimmune disease have elevated serum levels of soluble CD40L (sCD40L) that are not seen in healthy subjects. Overexpression of CD40L causes autoimmune diseases similar to systemic lupus erythromatosus in rodent models (Higuchi et al. (2002) *J. Immunol.* 168:9-12). In contrast, absence of functional CD40L on activated T cells causes X-linked hyper-IgM syndrome (Allen et al. (1993) *Science* 259:990; and Korthauer et al. (1993) *Nature* 361:539). Further, blocking of CD40/CD40L interaction can prevent transplant rejection in non-human primate models. See, for example, Wee et al. (1992) *Transplantation* 53:501-7.

CD40 expression on APCs plays an important co-stimulatory role in the activation of these cells. For example, agonistic anti-CD40 monoclonal antibodies (mAbs) have been shown to mimic the effects of T helper cells in B-cell activation. When presented on adherent cells expressing FcγRII, these antibodies induce B-cell proliferation (Banchereau et al. (1989) *Science* 251:70). Moreover, agonistic anti-CD40 mAbs can replace the T helper signal for secretion of IgM, IgG, and IgE in the presence of IL-4 (Gascan et al. (1991) *J. Immunol.* 147:8). Furthermore, agonistic anti-CD40 mAbs can prevent programmed cell death (apoptosis) of B cells isolated from lymph nodes.

These and other observations support the current theory that the interaction of CD40 and CD40L plays a pivotal role in regulating both humoral and cell-mediated immune responses. More recent studies have revealed a much broader role of CD40/CD40L interaction in diverse physiological and pathological processes.

The CD40 signal transduction pathway depends on the coordinated regulation of many intracellular factors. Like other members of the TNF receptor family, CD40 activates TRAFs, including TRAF-1, TRAF-2, -3, -5, and -6, which upregulate diverse signaling pathways following engagement of CD40 with CD40L (either membrane-bound CD40L or soluble CD40L), including extracellular signal-regulated kinase (ERK), c-jun amino terminal kinase (JNK), p38 MAPK, and NF-κB (see, for example, Younes and Carbone (1999) *Int. J. Biol. Markers* 14:135-143; van Kooten and Banchereau (2000) *J. Leukoc. Biol.* 67:2-17).

Signaling via CD40 has been shown to prevent cell death from apoptosis (Makus et al. (2002) *J. Immunol.* 14:973-982). Apoptotic signals are necessary to induce programmed cell death in a coordinated manner. Cell death signals can include intrinsic stimuli from within the cell such as endoplasmic reticulum stress or extrinsic stimuli such as receptor binding of FasL or TNFα. The signaling pathway is complex, involving activation of caspases such as Caspase-3 and Caspase-9, and of poly (ADP ribose) polymerase (PARP). During the cascade, anti-apoptotic signaling proteins, such as Mcl-1 and Bcl-x, and members of the IAP family of proteins, such as X-Linked Inhibitor of Apoptosis (XIAP), are down-regulated (Budihardjo et al. (1999) *Annu. Rev. Cell Dev. Biol.* 15:269-290). For example, in dendritic cells, CD40 cell signaling can block apoptosis signals transduced by FasL (Bjorck et al. (1997) *Intl. Immunol.* 9:365-372).

Thus, CD40 engagement by CD40L and subsequent activation of CD40 signaling are necessary steps for normal immune responses; however, dysregulation of CD40 signaling can lead to disease. The CD40 signaling pathway has been shown to be involved in autoimmune disease (Ichikawa et al. (2002) *J. Immunol.* 169:2781-2787 and Moore et al. (2002) *J. Autoimmun.* 19:139-145). Additionally, the CD40/CD40L interaction plays an important role in inflammatory processes. For example, both CD40 and CD40L are overexpressed in human and experimental atherosclerosis lesions. CD40 stimulation induces expression of matrix-degrading enzymes and tissue factor expression in atheroma-associated cell types, such as endothelial cells, smooth muscle cells, and macrophages. Further, CD40 stimulation induces production of proinflammatory cytokines such as vascular endothelial growth factor (VEGF), IL-1, IL-6, and IL-8, and adhesion molecules such as ICAM-1, E-selectin, and VCAM. Inhibition of CD40/CD40L interaction prevents atherogenesis in animal models. In transplant models, blocking CD40/CD40L interaction prevents inflammation. It has been shown that CD40/CD40L binding acts synergistically with the Alzheimer amyloid-beta peptide to promote microglial activation, thus leading to neurotoxicity.

In patients with rheumatoid arthritis (RA), CD40 expression is increased on articular chondrocytes, thus, CD40 signaling likely contributes to production of damaging cytokines and matrix metalloproteinases. See, Gotoh et al. (2004) *J. Rheumatol.* 31:1506-1512. Further, it has been shown that amplification of the synovial inflammatory response occurs through activation of MAPKs and NF-κB via ligation of CD40 on CD14$^+$ synovial cells from RA patients (Harigai et al. (2004) *Arthritis. Rheum.* 50:2167-2177). In an experimental model of RA, anti-CD40L antibody treatment prevented disease induction, joint inflammation, and anti-collagen antibody production (Durie et al. (1993) *Science* 261:1328-1330). Finally, in clinical trials, it has been shown that depleting CD20$^+$ positive B cells of RA patients by administering Rituxan® (generally indicated for B cell lymphoma) improves symptoms (Shaw et al. (2003) *Ann. Rheum. Dis.* 62(Suppl. 2):ii55-ii59).

Blocking CD40/CD40L interactions during antigen presentation to T cells has also been shown to induce T cell tolerance. Therefore, blocking CD40/CD40L interaction prevents initial T cell activation as well as induces long term tolerance to re-exposure to the antigen.

Given the important role of CD40L-mediated CD40 signaling in maintenance of normal immunity, methods for identifying individuals with an autoimmune and/or inflammatory disease who would be responsive to treatment regimens that target CD40 signaling are needed.

BRIEF SUMMARY OF THE INVENTION

Methods for identifying subjects having an inflammatory disease and/or autoimmune disease that will benefit from anti-CD40 therapeutic agents including those that modulate CD40L-mediated signaling and/or modulate antibody-dependent cellular cytotoxicity (ADCC) are provided. Such anti-CD40 therapeutic agents include, but are not limited to, antagonist anti-CD40 antibodies, antagonist anti-CD40L antibodies, and pharmacologic agents that block or interfere with CD40/CD40L interaction, particularly CD40L-mediated CD40 signaling, as well as antagonist anti-CD40 antibodies that additionally, or alternatively, have ADCC activity as a mode of action. In some embodiments, the methods comprise the use of biomarkers of cellular apoptosis, cell proliferation and survival, and CD40 signaling pathways to monitor ex vivo cellular response to one or more anti-CD40 therapeutic agents of interest. These ex vivo prognostic assays comprise providing a test biological sample and a control biological sample from a candidate subject, where these biological samples comprise CD40-expressing cells that have been stimulated with a CD40 ligand, either in vivo or ex vivo; contacting the test biological sample with the anti-CD40 therapeutic agent of interest; detecting the expression level of at least one biomarker within the test biological sample; and comparing the expression level of the biomarker(s) with the corresponding expression level detected in the control biological sample that has not been contacted with the anti-CD40 therapeutic agent of interest. Biomarkers for use in these ex vivo prognostic assays include proteins and/or genes whose expression levels are prognostic indicators of responsiveness to treatment intervention, including biomarkers of cellular apoptosis, biomarkers of CD40L-mediated CD40 signaling pathways, and biomarkers of cell proliferation or survival, depending upon the mode of action of the anti-CD40 therapeutic agent. Where the anti-CD40 therapeutic agent has its mode of action via disruption of CD40L-mediated CD40 signaling, biomarkers of cellular apoptosis, CD40L-mediated CD40 signaling pathways, and cell proliferation or survival can be used in these ex vivo prognostic assays. In some embodiments, additional markers of CD40L-mediated CD40 signaling can be assayed, including, but not limited to, cytokines that are upregulated via CD40L-CD40 interaction, for example, vascular endothelial growth factor (VEGF), interleukin (IL-)6, IL-8, IL-10, tumor necrosis factor-α (TNF-α), monocyte chemoattractant protein-1 (MCP-1), and macrophage inflammatory protein-1β (MIP-1β). Where the anti-CD40 therapeutic agent has its mode of action via ADCC, for example, an anti-CD40 antibody, biomarkers of cellular apoptosis can be used in these ex vivo prognostic assays.

In other embodiments of the invention, candidate subjects are screened for the expression level of one or more CD40-related factors that are predictive of an individual, or a subpopulation of individuals, who will benefit from intervention with anti-CD40 therapeutic agents. Thus, in one embodiment, biological samples collected from candidate subjects, for example, subjects having a disease comprising an autoimmune and/or inflammatory component, are screened for one or more CD40-related factors selected from the group consisting of expression level of cell-surface CD40 antigen on cells of a biological sample, expression level of cell-surface CD40L on cells of a biological sample, circulating level of soluble CD40 (sCD40), and circulating level of soluble CD40L (sCD40L). These CD40-related factors can be prognostic indicators of the disease, and can further be used to identify subjects who would or would not respond to therapeutic intervention with anti-CD40 therapeutic agents, regardless of the mode of action of the anti-CD40 therapeutic agent. An elevated level of expression of one or more of these CD40-related factors within a biological sample when compared to a control or reference standard would be indicative of an individual who would benefit from therapeutic intervention with an anti-CD40 therapeutic agent that modulates CD40L-mediated CD40 signaling, modulates ADCC, or both. Candidate subjects identified with this screening process can be treated with an anti-CD40 therapeutic agent of interest, or can be further screened for responsiveness to anti-CD40 therapeutic agents using the ex vivo prognostic assays described herein.

In yet other embodiments, candidate subjects are screened for the presence or absence of one or more clinically useful prognostic markers in order to define subpopulations of candidate subjects who have a poor prognosis with other classes of therapeutics but who will benefit from intervention with anti-CD40 therapeutic agents. In this manner, biological samples collected from candidate subjects are screened for one or more clinically useful prognostic markers known to be indicators of poor prognosis with current therapeutics whose mode of action is not via CD40 targeting or CD40L-mediated CD40 signaling. Any clinically useful prognostic marker for a given autoimmune or inflammatory disease can be included in the screening process. Candidate subjects within a subpopulation identified with this screening process can be further screened for responsiveness to anti-CD40 therapeutic agents using the ex vivo prognostic assays described herein.

The present invention also provides methods for monitoring efficacy of an anti-CD40 therapeutic agent in treatment of a subject having an inflammatory disease or autoimmune disease. In this manner, a subject undergoing therapy with an anti-CD40 therapeutic agent, who may or may not have been previously screened using an ex vivo prognostic assay disclosed herein, is monitored for in vivo changes in the expression of at least one biomarker of cellular apoptosis, cell proliferation and survival, and/or one or more CD40L-mediated CD40 signaling pathways following treatment with the anti-CD40 therapeutic agent. The particular biomarkers to be assayed can be chosen based on mode of action of the therapeutic agent as noted above. Alternatively, or additionally, the subject can be monitored for in vivo changes in the expression level of one or more CD40-related factors selected from the group consisting of cell-surface CD40 antigen on cells, cell-surface CD40L on cells, circulating level of sCD40, and circulating level of sCD40L following treatment with the anti-CD40 therapeutic agent. In this manner, a first biological sample is obtained from the subject and assayed for the expression level of one or more of these biomarkers and/or CD40-related factors to obtain a baseline level of expression for each factor assayed, and then one or more subsequent biological samples is obtained from the subject and assayed for the same biomarker(s) and/or CD40-related factor(s), where the subsequent biological sample is obtained following the administration of at least one dose of the anti-CD40 therapeutic agent of interest. Monitoring can occur at a single point in time, or at multiple points in time, to ascertain efficacy of any given treatment protocol wherein the anti-CD40 therapeutic agent is administered to the subject. Depending upon the biomarker being assayed, a decrease or increase in the expression level of the biomarker between any two time points can be indicative of efficacy of the anti-CD40 therapeutic agent in treatment of the inflammatory disease or autoimmune disease. Where monitoring reveals a decrease in the expression level of one or more of the CD40-related factors, such a result can be indicative of efficacy of the anti-CD40 therapeutic agent in treatment of the inflammatory disease or autoimmune disease.

Expression level of these various biomarkers and CD40-related factors, and any clinically useful prognostic markers in a biological sample can be detected at the protein or nucleic acid level, using, for example, immunohistochemistry techniques or nucleic acid-based techniques such as in situ hybridization and RT-PCR. In some embodiments, an elevated level or an increase in expression of at least one biomarker is indicative of a positive therapeutic response to treatment with an anti-CD40 therapeutic agent. In other embodiments, a diminished level or a decrease in expression of at least one biomarker is indicative of a positive therapeutic response to treatment with the anti-CD40 therapeutic agent.

The methods of the present invention can be used to identify subjects for whom anti-CD40 therapeutic intervention would be beneficial in preventing, ameliorating, or treating diseases comprising an autoimmune and/or inflammatory component, including, but not limited to, autoimmune and inflammatory diseases such as systemic lupus erythematosus (SLE), discoid lupus, lupus nephritis, sarcoidosis, inflammatory arthritis, including, but not limited to, juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, sarcoidosis, Type I and Type II diabetes mellitus, type 1, 2, 3, and 4 delayed-type hypersensitivity, allergy or allergic disorders, unwanted/unintended immune responses to therapeutic proteins, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like.

BRIEF DESCRIPTION OF THE DRAWINGS

FIG. 1 shows that signaling and survival of normal human B Cells are induced by CD40L and blocked by CHIR-12.12.

DETAILED DESCRIPTION OF THE INVENTION

The present invention is directed to methods for identifying subjects having an inflammatory disease or autoimmune disease that would benefit from treatment with anti-CD40 therapeutic agents that target the CD40 receptor and which modulate ADCC, interfere with CD40 signaling, particularly CD40 signaling pathways that are mediated by interaction of CD40 with the CD40 ligand (CD40L), or both. In one embodiment, the methods comprise the use of ex vivo prognostic assays to monitor the effects of antagonist anti-CD40 therapeutic agents that block or interfere with CD40L-mediated CD40 signaling on the expression level of three classes of biomarkers that are associated with CD40L-mediated CD40 signaling, particularly biomarkers of cell proliferation or survival and cell apopototic pathways and biomarkers of key CD40L-mediated CD40 signaling pathways, including the AKT, NF-κB, and mitogen-activated protein kinase (MAPK) signaling pathways. Additional markers that can serve to monitor effects of antagonist anti-CD40 therapeutic agents that block or interfere with CD40L-mediated CD40 signaling include cytokines that are upregulated via CD40L-mediated CD40 signaling, as noted herein below. Biomarkers for cell apoptotic pathways can also serve to monitor effects of anti-CD40 therapeutic agents that modulate ADCC, for example, anti-CD40 antibodies having ADCC as a mode of action. Therapeutic agents that act as antagonists of CD40 signaling, referred to herein as "CD40 antagonists," can interfere with one or more of the signaling cues normally triggered by binding of CD40L to the CD40 receptor. The ex vivo prognostic assays of the present invention can be used to discriminate between subjects who would benefit from intervention with CD40 antagonists and therapeutic agents that target CD40 and modulate ADCC and those for whom intervention with these types of therapeutic agents would not be beneficial. Candidate subjects can additionally, or alternatively, be screened for the presence or absence of, or elevated or diminished levels of, one or more CD40-related factors and/or one or more clinically useful prognostic markers to define individuals or subpopulations of candidate subjects who would benefit from therapeutic intervention with anti-CD40 therapeutic agents that modulate CD40L-mediated CD40 signaling and/or ADCC. Subjects identified in these screening methods can be further screened using the ex vivo prognostic assays described herein. The biomarkers and CD40-related factors described herein also find use in monitoring efficacy of treatment with anti-CD40 therapeutic agents that modulate CD40 signaling and/or ADCC, and in determining the basis for drug responsiveness in individual patients or subpopulations of patients having an inflammatory disease or autoimmune disease.

By "CD40 antigen," "CD40 cell surface antigen," "CD40 receptor," or "CD40" is intended a transmembrane glycoprotein that belongs to the tumor necrosis factor (TNF) receptor family (see, for example, U.S. Pat. Nos. 5,674,492 and 4,708, 871; Stamenkovic et al. (1989) *EMBO* 8:1403; Clark (1990) *Tissue Antigens* 36:33; Barclay et al. (1997) *The Leucocyte Antigen Facts Book* (2d ed.; Academic Press, San Diego)). Two isoforms of human CD40, encoded by alternatively spliced transcript variants of this gene, have been identified. The first isoform (also known as the "long isoforms" or "isoform 1") is expressed as a 277-amino-acid precursor polypeptide (SEQ ID NO:12 (first reported as GenBank Accession No. CAA43045, and identified as isoform 1 in GenBank Accession No. NP_001241), encoded by SEQ ID NO:11 (see GenBank Accession Nos. X60592 and NM_001250)), which has a signal sequence represented by the first 19 residues. The second isoform (also known as the "short isoforms" or "isoform 2") is expressed as a 203-amino-acid precursor polypeptide (SEQ ID NO:10 (GenBank Accession No. NP_690593), encoded by SEQ ID NO:9 (GenBank Accession No. NM_152854)), which also has a signal sequence represented by the first 19 residues. The precursor polypeptides of these two isoforms of human CD40 share in common their first 165 residues (i.e., residues 1-165 of SEQ ID NO:10 and SEQ ID NO:12). The precursor polypeptide of the short isoform (shown in SEQ ID NO:10) is encoded by a transcript variant (SEQ ID NO:9) that lacks a coding segment, which leads to a translation frame shift; the resulting CD40 isoform contains a shorter and distinct C-terminus (residues 166-203 of SEQ ID NO:10) from that contained in the long isoform of CD40 (C-terminus shown in residues 166-277 of SEQ ID NO:12). For purposes of the present invention, the term "CD40 antigen," "CD40 cell surface antigen," "CD40 receptor," or "CD40" encompasses both the short and long isoforms of CD40.

The CD40 antigen is displayed on the surface of a variety of cell types, as described elsewhere herein. By "displayed on the surface" and "expressed on the surface" is intended that all or a portion of the CD40 antigen is exposed to the exterior of the cell. The displayed or expressed CD40 antigen may be fully or partially glycosylated.

By "agonist activity" is intended that the substance functions as an agonist. An agonist combines with a receptor on a cell and initiates a reaction or activity that is similar to or the same as that initiated by the receptor's natural ligand. For example, an agonist of CD40 induces any or all of, but not limited to, the following responses: cell proliferation and/or differentiation; upregulation of intercellular adhesion via such molecules as ICAM-1, E-selectin, VCAM, and the like; secretion of pro-inflammatory cytokines such as VEGF, IL-1, IL-6, IL-8, IL-12, TNF, and the like; signal transduction through the CD40 receptor by such pathways as TRAF (e.g., TRAF-1, TRAF2, TRAF3), MAP kinases such as NIK (NF-κB inducing kinase), I-kappa B kinases (IKK α/β), transcription factor NF-κB, Ras and the MEK/ERK pathway, the PI3K/AKT pathway, the P38 MAPK pathway, and the like; transduction of an anti-apoptotic signal by such molecules as XIAP, Mcl-1, Bcl-x, and the like; B and/or T cell memory generation; B cell antibody production; B cell isotype switching, up-regulation of cell-surface expression of MHC Class II and CD80/86, and the like.

By "antagonist activity" is intended that the substance functions as an antagonist. For example, an antagonist of CD40 prevents or reduces induction of any of the responses induced by binding of the CD40 receptor to an agonist ligand, particularly CD40L. The antagonist may reduce induction of any one or more of the responses to agonist binding by 5%, 10%, 15%, 20%, 25%, 30%, 35%, preferably 40%, 45%, 50%, 55%, 60%, more preferably 70%, 80%, 85%, and most preferably 90%, 95%, 99%, or 100%. Methods for measuring CD40 ligand binding specificity and antagonist activity of an anti-CD40 therapeutic agent, for example, an anti-CD40 antibody, are known to one of skill in the art and include, but are not limited to, standard competitive binding assays, assays for monitoring immunoglobulin secretion by B cells, B cell proliferation assays, Banchereau-Like-B cell proliferation assays, T cell helper assays for antibody production, co-stimulation of B cell proliferation assays, and assays for up-regulation of B cell activation markers. See, for example, such assays disclosed in WO 00/75348 and U.S. Pat. No. 6,087,329. Also see, provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517, 337 , 60/525,579, and 60/565,710, respectively, and International Patent Application No. PCT/US2004/037152, also entitled "Antagonist Anti-CD40 Monoclonal Antibodies and Methods for Their Use," filed Nov. 4, 2004, and published as WO 2005/044854; the contents of each of which are herein incorporated by reference in their entirety.

By "significant" agonist activity is intended an agonist activity of at least 30%, 35%, 40%, 45%, 50%, 60%, 70%, 75%, 80%, 85%, 90%, 95%, or 100% greater than the agonist activity induced by a neutral substance or negative control as measured in an assay of a B cell response. Preferably, "significant" agonist activity is an agonist activity that is at least 2-fold greater or at least 3-fold greater than the agonist activity induced by a neutral substance or negative control as measured in an assay of a B cell response. Thus, for example, where the B cell response of interest is B cell proliferation, "significant" agonist activity would be induction of a level of B cell proliferation that is at least 2-fold greater or at least 3-fold greater than the level of B cell proliferation induced by a neutral substance or negative control. In one embodiment, a non-specific immunoglobulin, for example IgG1, that does not bind to CD40 serves as the negative control. A substance "free of significant agonist activity" would exhibit an agonist activity of not more than about 25% greater than the agonist activity induced by a neutral substance or negative control, preferably not more than about 20% greater, 15% greater, 10% greater, 5% greater, 1% greater, 0.5% greater, or even not more than about 0.1% greater than the agonist activity induced by a neutral substance or negative control as measured in a bioassay such as a B cell response assay.

In some embodiments of the invention, the anti-CD40 therapeutic agent is an antagonist anti-CD40 antibody. Such antibodies are free of significant agonist activity as noted above when bound to a CD40 antigen on a human cell. In one embodiment of the invention, the antagonist anti-CD40 antibody is free of significant agonist activity in one cellular response. In another embodiment of the invention, the antagonist anti-CD40 antibody is free of significant agonist activity in assays of more than one cellular response (e.g., proliferation and differentiation, or proliferation, differentiation, and, for B cells, antibody production). In some embodiments of the invention, the anti-CD40 therapeutic agent of interest is the fully human monoclonal antibody CHIR-12.12 or CHIR-5.9, or antigen-binding fragment thereof, as noted herein below.

Any of the assays known in the art can be used to determine whether an anti-CD40 therapeutic agent acts as an antagonist of one or more B cell responses. In some embodiments, the therapeutic agent is an anti-CD40 antibody that acts as an antagonist of at least one B cell response selected from the group consisting of B cell proliferation, B cell differentiation, antibody production, intercellular adhesion, B cell memory generation, isotype switching, up-regulation of cell-surface expression of MHC Class II and CD80/86, and secretion of pro-inflammatory cytokines such as VEGF, IL-8, IL-12, and TNF. Of particular interest are antagonist anti-CD40 antibodies that free of significant agonist activity with respect to B cell proliferation when bound to the human CD40 antigen on the surface of a human B cell.

In one such embodiment, the anti-CD40 antibody is an antagonist of B cell proliferation as measured in a B cell proliferation assay such as that described in Example 4 herein below, and the antagonist anti-CD40 antibody stimulates B cell proliferation at a level that is not more than about 25% greater than the B cell proliferation induced by a neutral substance or negative control, preferably not more than about 20% greater, 15% greater, 10% greater, 5% greater, 1% greater, 0.5% greater, or even not more than about 0.1% greater than the B cell proliferation induced by a neutral substance or negative control.

In other embodiments, the anti-CD40 antibody is an antagonist of B cell proliferation that is induced by another anti-CD40 antibody, for example, the S2C6 anti-CD40 antibody, as measured in a B cell proliferation assay such as that described in Example 4 herein below, and the level of B cell proliferation stimulated by the other anti-CD40 antibody in the presence of the antagonist anti-CD40 antibody is not more than about 25% of the B cell proliferation induced by the other anti-CD40 antibody in the absence of the antagonist anti-CD40 antibody (i.e., at least 75% inhibition), preferably not more than about 20%, 15%, 10%, 5%, 1%, 0.5%, or even not more than about 0.1% of the B cell proliferation induced by the other anti-CD40 antibody in the absence of the antagonist anti-CD40 antibody.

In yet other embodiments, the anti-CD40 antibody is an antagonist of B cell proliferation that is induced by the cell line EL4B5 as measured in the B cell activation assay described in Example 4 herein below, and the level of B cell proliferation stimulated by the EL4B5 cell line in the presence of the antagonist anti-CD40 antibody is not more than about 25% of the B cell proliferation induced by this cell line in the absence of the antagonist anti-CD40 antibody (i.e., at least 75% inhibition), preferably not more than about 20%, 15%, 10%, 5%, 1%, 0.5%, or even not more than about 0.1% of the B cell proliferation induced by this cell line in the absence of the antagonist anti-CD40 antibody.

In still other embodiments, the anti-CD40 antibody is an antagonist of human T-cell-induced antibody production by human B cells as measured in the human T-cell helper assay for antibody production by B cells described in Example 4 herein below. In this manner, the level of IgG antibody production, IgM antibody production, or both IgG and IgM antibody production by B cells stimulated by T cells in the presence of the antagonist anti-CD40 antibody is not more than about 50% of the respective antibody production by B cells stimulated by T cells in the absence of the antagonist anti-CD40 antibody (i.e., at least 75% inhibition), preferably not more than about 25%, 20%, 15%, 10%, 5%, 1%, 0.5%, or even not more than about 0.1% of the respective antibody production by B cells stimulated by T cells in the absence of the antagonist anti-CD40 antibody.

By "CD40 ligand" is intended any peptide, polypeptide, or protein that can bind to and activate one or more CD40 signaling pathways. Thus, "CD40 ligands" include, but are not limited to, full-length CD40 ligand proteins and variants and fragments thereof that retain sufficient activity to carry out the function of binding to and stimulating CD40 signaling on CD40-expressing cells. Modifications to a native CD40 ligand, for example, human CD40 ligand (CD40L; also known as CD154), include, but are not limited to, substitutions, deletions, truncations, extensions, fusion proteins, fragments, peptidomimetics, and the like. In some embodiments of the invention, the ex vivo prognostic assays include the use of soluble CD40L, for example, soluble recombinant human CD40L (Alexis Corporation, Bingham, Nottinghamshire, UK) to stimulate CD40 signaling on CD40-expressing cells of a biological sample.

By "CD40L-mediated CD40 signaling" is intended any of the biological activities that result from interaction of the cell-surface receptor CD40 with a CD40 ligand. Examples of CD40 signaling are signals that lead to proliferation and survival of CD40-expressing cells, and stimulation of one or more CD40-signaling pathways within CD40-expressing cells. A CD40 "signaling pathway" or "signal transduction pathway" is intended to mean at least one biochemical reaction, or a group of biochemical reactions, that results from interaction of the CD40 receptor with a CD40 ligand, for example, CD40L, and which generates a signal that, when transmitted through the signal pathway, leads to activation of one or more downstream molecules in the signaling cascade. Signal transduction pathways involve a number of signal transduction molecules that lead to transmission of a signal from the cell-surface CD40 receptor across the plasma membrane of a cell, and through one or more in a series of signal transduction molecules, through the cytoplasm of the cell, and in some instances, into the cell's nucleus. Of particular interest to the present invention are CD40 signal transduction pathways, including the AKT signaling pathway, which leads to activation of AKT, and ultimately activation of NF-κB via the NF-κB signaling pathway; and mitogen-activated protein kinase (MAPK) signaling pathways, including the MEK/ERK signaling pathway and the MEK/p38 signaling pathway, which lead to activation of ERK and p38, respectively. The balance between activation and blocking of these signaling pathways favors either cell survival or apoptosis as noted herein below.

The methods of the present invention are directed to ex vivo prognostic assays, and prognostic assays that utilize antibodies, either in a detection step, or as candidate anti-CD40 therapeutic agents that are being tested in these ex vivo prognostic assays. The following terms and definitions apply to such antibodies.

"Antibodies" and "immunoglobulins" (Igs) are glycoproteins having the same structural characteristics. The terms are used synonymously. In some instances the antigen specificity of the immunoglobulin may be known.

The term "antibody" is used in the broadest sense and covers fully assembled antibodies, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see, Kabat et al. (1991) *NIH Publ. No.* 91-3242, Vol. I, pages 647-669). The constant domains are not involved directly in binding an antibody to an antigen, but exhibit various effector functions, such as Fc receptor binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) *Sequences of Proteins of Immunological Interest,* 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (H3) in the heavy chain variable domain; Clothia and Lesk, (1987) *J. Mol. Biol.,* 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) *Protein Eng.* 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy chain $C_H1$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

A "host cell," as used herein, refers to a microorganism or a eukaryotic cell or cell line cultured as a unicellular entity that can be, or has been, used as a recipient for a recombinant vector or other transfer polynucleotides, and include the progeny of the original cell that has been transfected. It is understood that the progeny of a single cell may not necessarily be completely identical in morphology or in genomic or total DNA complement as the original parent, due to natural, accidental, or deliberate mutation.

"Human effector cells" are leukocytes that express one or more FcRs and perform effector functions. Preferably, the cells express at least FcγRIII and carry out antigen-dependent cell-mediated cyotoxicity (ADCC) effector function. Examples of human leukocytes that mediate ADCC include peripheral blood mononuclear cells (PBMC), natural killer (NK) cells, monocytes, macrophages, eosinophils, and neutrophils, with PBMCs and NK cells being preferred. Antibodies that have ADCC activity are typically of the IgG1 or IgG3 isotype. Note that in addition to isolating IgG1 and IgG3 antibodies, such ADCC-mediating antibodies can be made by engineering a variable region from a non-ADCC antibody or variable region fragment to an IgG1 or IgG3 isotype constant region.

The terms "Fc receptor" or "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see Daeron (1997) *Annu. Rev. Immunol.* 15:203-234). FcRs are reviewed in Ravetch and Kinet (1991) *Annu. Rev. Immunol.* 9:457-492; Capel et al. (1994) *Immunomethods* 4:25-34; and de Haas et al. (1995) *J. Lab. Clin. Med.* 126:330-341. Other FcRs, including those to be identified in the future, are encompassed by the term "FcR" herein. The term also includes the neonatal receptor, FcRn, which is responsible for the transfer of maternal IgGs to the fetus (Guyer et al. (1976) *J. Immunol.* 117:587 and Kim et al. (1994) *J. Immunol.* 24:249).

There are a number of ways to make human antibodies. For example, secreting cells can be immortalized by infection with the Epstein-Barr virus (EBV). However, EBV-infected cells are difficult to clone and usually produce only relatively low yields of immunoglobulin (James and Bell (1987) *J. Immunol. Methods* 100:5-40). In the future, the immortalization of human B cells might possibly be achieved by introducing a defined combination of transforming genes. Such a possibility is highlighted by a recent demonstration that the expression of the telomerase catalytic subunit together with the SV40 large oncoprotein and an oncogenic allele of H-ras resulted in the tumorigenic conversion of normal human epithelial and fibroblast cells (Hahn et al. (1999) *Nature* 400: 464-468). It is now possible to produce transgenic animals (e.g., mice) that are capable, upon immunization, of producing a repertoire of human antibodies in the absence of endogenous immunoglobulin production (Jakobovits et al. (1993) *Nature* 362:255-258; Lonberg and Huszar (1995) *Int. Rev. Immunol.* 13:65-93; Fishwild et al. (1996) *Nat. Biotechnol.* 14:845-851; Mendez et al. (1997) *Nat. Genet.* 15:146-156; Green (1999) *J. Immunol. Methods* 231:11-23; Tomizuka et al. (2000) *Proc. Natl. Acad. Sci. USA* 97:722-727; reviewed in Little et al. (2000) *Immunol. Today* 21:364-370). For example, it has been described that the homozygous deletion of the antibody heavy-chain joining region ($J_H$) gene in chimeric and germ-line mutant mice results in complete inhibition of endogenous antibody production (Jakobovits et al. (1993) *Proc. Natl. Acad. Sci. USA* 90:2551-2555). Transfer of the human germ-line immunoglobulin gene array in such germ-line mutant mice results in the production of human antibodies upon antigen challenge (Jakobovits et al. (1993) *Nature* 362:255-258). Mendez et al. (1997) (*Nature Genetics* 15:146-156) have generated a line of transgenic mice that, when challenged with an antigen, generates high affinity fully human antibodies. This was achieved by germ-line integration of megabase human heavy-chain and light-chain loci into mice with deletion into endogenous $J_H$ segment as described above. These mice (XenoMouse® II technology (Abgenix; Fremont, Calif.)) harbor 1,020 kb of human heavy-chain locus containing approximately 66 $V_H$ genes, complete $D_H$ and $J_H$ regions, and three different constant regions, and also harbors 800 kb of human κ locus containing 32 Vκ genes, Jκ segments, and Cκ genes. The antibodies produced in these mice closely resemble that seen in humans in all respects, including gene rearrangement, assembly, and repertoire. The human antibodies are preferentially expressed over endogenous antibodies due to deletion in endogenous segment that prevents gene rearrangement in the murine locus. Such mice may be immunized with an antigen of particular interest.

Sera from such immunized animals may be screened for antibody reactivity against the initial antigen. Lymphocytes may be isolated from lymph nodes or spleen cells and may further be selected for B cells by selecting for CD138-negative and CD19-positive cells. In one aspect, such B cell cultures (BCCs) may be fused to myeloma cells to generate hybridomas as detailed above.

In another aspect, such B cell cultures may be screened further for reactivity against the initial antigen, preferably. Such screening includes enzyme-linked immunosorbent assay (ELISA) with the target/antigen protein, a competition assay with known antibodies that bind the antigen of interest, and in vitro binding to transiently transfected CHO or other cells that express the target antigen.

Biomarkers, Cytokine Markers, CD40-Related Factors, and Clinically Useful Prognostic Markers for Use in the Prognostic Assays of the Invention In some embodiments, the methods of the present invention comprise the use of ex vivo prognostic assays to monitor changes in the expression level of one or more biomarkers of cell survival, proliferation, apoptosis, and CD40 signaling pathways. The ex vivo prognostic assays can be used alone, or in combination with other prognostic assays, for example, prognostic assays that identify candidate subjects having an inflammatory disease or autoimmune disease that would be responsive to treatment with anti-CD40 therapeutic agents based on expression of other CD40-related factors and/or based on the presence or absence of, or elevated or diminished expression of, other clinically useful prognostic markers that are indicative of poor prognosis with treatment intervention with standard therapeutic agents having a different mode of action from that exerted by anti-CD40 therapeutic agents. By "responsive to treatment with an anti-CD40 therapeutic agent" is intended the candidate subject (i.e., an individual with an inflammatory disease or autoimmune disease as noted herein below), when treated with the anti-CD40 therapeutic agent, would have a positive therapeutic response with respect to the autoimmune disease and/or inflammatory disease for which treatment is sought.

Biomarkers for Use in Ex Vivo Prognostic Assays.

Signaling pathways are characterized by protein families that facilitate signal transduction. The term "family" when referring to protein and nucleic acid molecules is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

The AKT (sometimes referred to as PKB, for protein kinase B) family of serine/threonine kinases, is integrally involved in cell growth, survival, and metabolism. PKB was originally identified as a retroviral oncogene. Currently, three variants of the AKT family, the 480-residue AKT-1, the 481-residue AKT-2, and the 479-residue AKT-3, have been characterized. For purposes of the present invention, members of the AKT family of proteins will be referred to generally as AKT proteins, though it is recognized that the methods of the present invention apply to all three forms of AKT, i.e., AKT-1, AKT-2, and AKT-3, and variants thereof.

AKT is a growth factor-regulated serine/threonine kinase that contains a PH (pleckstrin homology) domain. This PH domain interacts with lipid products of phosphatidylinositol 3-kinase (PI3K), phosphatidylinositol-3,4-biphosphate, and phosphatidylinositol-3,4,5-triphosphate, which results in translocation of AKT from a cell's cytosol to its plasma membrane. This translocation is required in order to present AKT to an upstream activation kinase, PDK1 (phosphoinositide-dependent kinase 1). A variety of survival and growth factors such as PDGF, EGF, insulin, thrombin, and NGF are known to activate the translocation of AKT. The activated (i.e., phosphorylated) form of AKT/PKB protein phosphorylates numerous substrates, including GSK-3 (glycogen synthase kinase 3), eNOS (endothelial nitric oxide synthase), FKHR 1 (forkhead transcription factor family member 1), Bad (Bcl-2 pro-apoptotic family member), and p21 CIP (inhibitor of cell cycle progression). These actions can result in diverse biological effects such as suppression of apoptosis, control of glucose metabolism, cell proliferation, transcription, translation, cell migration, and angiogenesis. Activated AKT (i.e., p-AKT) promotes cell survival through several distinct pathways that involve phosphorylation of downstream effector molecules. First, p-AKT inhibits apoptosis by phosphorylating the Bad component of the Bad/Bcl-xl complex. Phosphorylated Bad binds to 14-3-3 causing dissociation of the Bad/Bcl-xl complex and thereby freeing Bcl-xl to allow for cell survival. Second, NF-κB, which is kept inactive in the cytoplasm through association with inhibitory proteins of the I kappa-B (Iκ-B) family, can be activated by interaction with NF-κB inducing kinase (NIK) or it can be activated by the AKT signaling pathway. In this manner, activated AKT (i.e., p-AKT) activates an NF-κB inhibitory molecule of the Iκ-B family (for example, Iκ-Bα), via intermediate phosphorylation of the Iκ-B kinase multiprotein complex (IKK-α/β); activation of an Iκ-B leads to its degradation and release of previously bound NF-κB, which leads to activation of this transcription factor. The active form of NF-κB can then translocate into the nucleus and regulate the expression of hundreds of genes to oppose apoptosis. Another means by which AKT promotes cell survival and opposes apoptosis is by phosphorylation of the protease Caspase 9 or forkhead transcription factors such as FKHRL1.

In some embodiments, the methods of the present invention to identify subjects having an inflammatory disease or autoimmune disease that would benefit from treatment with an anti-CD40 therapeutic agent that blocks or interferes with CD40L-mediated CD40 signaling comprise the use of an ex vivo prognostic assay to monitor the effects of anti-CD40 therapeutic agents on CD40 signaling through the AKT and NF-κB signaling pathways. In this manner, a test biological sample collected from a candidate subject is contacted with the anti-CD40 therapeutic agent of interest for sufficient time to allow for modulation of CD40L-mediated CD40 signaling as noted herein below, and that sample is then assayed for changes in the expression level of at least one CD40 signaling biomarker selected from the group consisting of phosphorylated AKT (p-AKT), phosphorylated PI3K (p-PI3K), phosphorylated PDK1 (p-PDK1), phosphorylated IKK-α/β (p-IKK-α/β), phosphorylated Iκ-B (p-Iκ-B; for example, p-Iκ-Bα), and activated NF-κB. Detection of decreased expression levels of these phosphorylated biomarkers in a test biological sample comprising CD40L-stimulated CD40-expressing cells in response to incubation with an anti-CD40 therapeutic agent relative to that observed for a control biological sample is indicative of downregulation of CD40L-mediated CD40 signaling, and therefore indicative of a positive treatment outcome with that anti-CD40 therapeutic agent. In some embodiments, the level of expression of any given biomarker of CD40 signaling through the AKT and NF-κB signaling pathways is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the control biological sample.

CD40/CD40L interaction also leads to activation of the MAPK signaling cascades including the MEK/ERK signaling pathway, the MEK/p38 signaling pathway, and the MEKK/JNKK/JNK signaling pathway. All MAPK pathways operate through sequential phosphorylation events to phosphorylate transcription factors and regulate gene expression. They can also phosphorylate cytosolic targets to regulate intracellular events. These cascades are implicated in the regulation of cellular proliferation, differentiation, development, cell cycle, and transmission of oncogenic signals. Of particular interest to the methods of the present invention are activation of the MEK/ERK and MEK/p38 signaling pathways.

The MAP kinases (also referred to as extracellular signal-regulated protein kinases, or ERKs) are the terminal enzymes in a three-kinase cascade, where each enzyme phosphorylates and thereby activates the next member in the sequence. Each MAPK module consists of three protein kinases: a MAPK kinase kinase (or MEKK) that activates a MAPK kinase (or MEK), which in turn activates a MAPK/ERK enzyme. The MEKKs are serine/threonine-specific protein kinases that dually phosphorylate, and thereby activate, one or more of the MEK enzymes on Ser or Thr residues (Ser-X-X-X-Ser/Thr) within the catalytic core. The MEKs are Serine/Threonine/Tyrosine-specific protein kinases that activate MAPKs by phosphorylating both Thr and Tyr within the TXY consensus sequence of the MAPKs. This dual phosphorylation is required for activation. ERK1 (p44), ERK2 (p42), p38/HOG, and JNK/SAPK represent related yet distinct terminal MAPKs in parallel pathways.

In some embodiments, the methods of the invention to identify subjects having an inflammatory disease or autoimmune disease that would benefit from treatment with an anti-CD40 therapeutic agent comprise the use of an ex vivo prognostic assay to monitor the effects of anti-CD40 therapeutic agents on CD40 signaling through the MEK/ERK and MEK/p38 pathways. In this manner, a test biological sample collected from a candidate subject is contacted with the therapeutic agent of interest for sufficient time to allow for modulation of CD40L-mediated CD40 signaling as noted herein below, and that sample is then assayed for changes in the expression level of at least one CD40 signaling biomarker selected from the group consisting of phosphorylated MEK (p-MEK), for example, p-MEK1, p-MEK2, p-MEK3, and p-MEK6, phosphorylated ERK (p-ERK), for example, p-ERK1 or p-ERK2, and phosphorylated p38 (p-p38). Detection of decreased expression levels of these phosphorylated biomarkers in a test biological sample comprising CD40L-stimulated CD40-expressing cells in response to incubation with an anti-CD40 therapeutic agent relative to that observed for a control biological sample is indicative of downregulation of CD40L-mediated CD40 signaling, and therefore indicative of a positive treatment outcome with that anti-CD40 therapeutic agent. In some embodiments, the level of expression of any given biomarker of CD40 signaling through the MEK/ERK and MEK/p38 pathways is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the control biological sample.

Responsiveness of a candidate subject to therapy with an anti-CD40 therapeutic agent that blocks or interferes with CD40L-mediated CD40 signaling can also be assessed by monitoring ex vivo effects of the therapeutic agent on expression level of any of the cytokine markers of CD40L-mediated CD40 signaling. Engagement of CD40 by its natural ligand in vivo results in upregulation of a number of proinflammatory cytokines depending upon the type of CD40-expressing cell. Ex vivo CD40L stimulation of normal B cells results in upregulation of production of several cytokines, including, but not limited to, vascular endothelial growth factor (VEGF), interleukin (IL)-6, IL-8, IL-10, tumor necrosis factor-α (TNF-α), monocyte chemoattractant protein-1 (MCP-1), and macrophage inflammatory protein-1β (MIP-1β), while ex vivo CD40L stimulation of monocytes results in upregulation of production of VEGF, IL-6, IL-8, IL-10, TNF-α, MCP-1, and MIP-1β as noted herein below.

In accordance with the screening methods of the present invention, a test biological sample collected from a candidate subject is contacted with the anti-CD40 therapeutic agent of interest for sufficient time to allow for modulation of CD40L-mediated CD40 signaling as noted herein below, and that sample is then assayed for changes in the expression level of at least one cytokine marker selected from the group consisting of VEGF, IL-6, IL-8, IL-10, TNF-α, MCP-1, and MIP-1β. Level of expression of cytokines can be accomplished using any detection method known in the art as noted herein below. Detection of decreased expression levels of these cytokine markers in a test biological sample comprising CD40L-stimulated CD40-expressing cells in response to incubation with an anti-CD40 therapeutic agent relative to that observed for a control biological sample is indicative of downregulation of CD40L-mediated CD40 signaling, and therefore indicative of a positive treatment outcome with that anti-CD40 therapeutic agent. In some embodiments, the level of expression of any given cytokine is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the control biological sample.

The AKT, NF-κB, and MAPK signaling pathways are all involved in cell proliferation and survival. In the immune system, apoptosis plays an important role in selection of T cell repertoire, deletion of self-reactive T and B lymphocytes, removal of peripheral effector T cells following termination of an immune response, regulation of immunological memory, and in the cytotoxicity of target cells by CTL and NK cells. Therapeutic agents that can block CD40 survival signaling on CD40-expressing cells and promote cellular apoptotic processes can be beneficial in treating diseases having an autoimmune and/or inflammatory component that is associated with CD40L-mediated CD40 signaling.

Thus, in addition to monitoring CD40 signaling on CD40-expressing cells, the methods of the present invention to identify subjects having an inflammatory disease or autoimmune disease that would benefit from treatment with an anti-CD40 therapeutic agent comprise the use of ex vivo prognostic assays that monitor the effects of anti-CD40 therapeutic agents on expression of one or more biomarkers of apoptosis, particularly cellular pro-apoptotic proteins, including, but not limited to, cleaved caspase proteins and cleaved poly ADP-ribose polymerase (PARP). Additional biomarkers of apoptosis that can be assayed include, but are not limited to, alterations in the plasma membrane at the cell surface, for example, presence of cell surface phosphotidylserine (PS), and cleavage or fragmentation of genomic DNA. PS normally is located exclusively at the inner side of the plasma membrane, but is translocated to the external surface of the cell during the early phases of apoptotic cell death during which the cell membrane remains intact. Presence of cell surface PS and genomic DNA fragmentation can be detected, for example, by annexin V staining and TUNEL staining, respectively, as noted herein below. Detection of increased expression levels of one or more of these biomarkers of apoptosis in a test biological sample comprising CD40L-stimulated CD40-expressing cells in response to incubation with an anti-CD40 therapeutic agent relative to that observed in a control biological sample is indicative of a positive treatment outcome with that anti-CD40 therapeutic agent. In some embodiments, the level of expression of any given biomarker of apoptosis is increased by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or higher relative to that detected in the control biological sample.

Alternatively, or in combination with the ex vivo assays described above, the methods of the present invention comprise the use of ex vivo prognostic assays that monitor the effects of anti-CD40 therapeutic agents on expression of one or more proteins that are biomarkers of cell proliferation and/or cell survival, including, but not limited to, an anti-apoptotic protein that is a member of the Bcl-2 family, an IAP apoptosis inhibitor protein, and TNF receptor-associated factor-1 (TRAF-1). Detection of decreased expression levels of these biomarkers of cell proliferation and/or cell survival in a biological sample comprising CD40L-stimulated CD40-expressing cells in response to incubation with an anti-CD40 therapeutic agent relative to that observed in a control biological sample is indicative of a positive treatment outcome with that anti-CD40 therapeutic agent. In some embodiments, the level of expression of any given biomarker of cell proliferation and/or cell survival is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the control biological sample.

Members of the caspase family of proteins are major effectors of cellular apoptosis. The caspases are cysteine proteases that exist within the cell as inactive pro-forms or so-called "zymogens." The zymogens are cleaved to form active enzymes following the induction of apoptosis either via the death receptor-mediated pathway or the mitochondrial pathway of apoptosis. See, for example, Gupta et al. (2003) *Intl. J. Oncol.* 22:15-20; herein incorporated by reference in its entirety. Depending upon the apoptotic pathway, different caspases initiate the apoptotic process, with Caspase-8 and -10 initiating the death receptor pathway, and Caspase-9 initiating the mitochondrial pathway. Active initiator caspases then activate (i.e., cleave) effector caspases, for example, Caspase-3, -6, and -7, to induce apopotosis. These effector caspases cleave key cellular proteins that lead to the typical morphological changes observed in cells undergoing apoptosis.

Thus, in some embodiments, the methods of the present invention to identify subjects having an inflammatory disease or an autoimmune disease that would benefit from treatment with an anti-CD40 therapeutic agent comprise the use of ex vivo prognostic assays to monitor the proteolysis of specific cellular proteins associated with apoptosis. For example, poly (ADP-ribose) polymerase (PARP-1) is specifically cleaved during apoptosis. PARP-1 is a DNA-binding protein that catalyzes the addition of poly(ADP-ribose) chains to some nuclear proteins and is thought to play a critical role in DNA damage repair. PARP-1 is rapidly activated during cellular stresses, such as heat shock, ionizing radiation, exposure to carcinogens, and treatment with chemotherapy agents (Scovassi and Poirier (1999) *Mol. Cell. Biochem.* 199:125-137; Wyllie (1997) *Eur. J. Cell Biol.* 73:189-197). During apoptosis, activated (i.e., cleaved) caspase-3 in turn cleaves PARP-1; in fact, the resolution of the 89 kDa and 24 kDa proteolytic fragments is accepted as a hallmarks of apoptosis (Scovassi and Poirier (1999) supra; Wyllie et al. (1997) supra. The ex vivo prognostic assays described herein monitor changes in the level of one or more cleaved caspase proteins, for example, cleaved Caspase-3, cleaved Caspase-7, and cleaved Caspase-9, and optionally, the level of cleaved PARP-1, cell surface PS, and/or genomic DNA fragmentation, in a test biological sample obtained from a candidate subject in response to anti-CD40 therapeutic agents that modulate CD40L-mediated CD40 signaling and/or modulate ADCC Elevated levels of apoptotic biomarkers within a biological sample can be detected using any method known to those of skill in the art, including those described herein below.

Biomarkers of cell survival and proliferation include, but are not limited to, anti-apoptotic proteins that are members of the Bcl-2 family of proteins. The Bcl-2 family of proteins, which comprises at least 16 members, participates in the regulation of cellular apoptosis. Some of the family members are anti-apoptotic, for example, Bcl-2, Bcl-xl, Mcl-1, Bcl-w, and Al, and thus biomarkers of cell survival, and others are pro-apoptotic (for example, Bid, Bim, Bik, Bmf, Bad, Hrk, BNIP3, Bax, Bak, and Bok), and thus biomarkers of apoptotic activity. Bcl-2 family members have been suggested to act through many different mechanisms, including pore formation in the outer mitochondrial membrane, through which cytochrome c (Cyt c) and other intermembrane proteins can escape; and heterodimerization between pro- and anti-apoptotic family members.

Effects of anti-CD40 therapeutic agents on CD40 signaling and modulation of apoptosis can be assessed with the ex vivo prognostic assays described herein to monitor one or more of these biomarkers of cell survival/apoptosis. Biomarkers of cell survival that are of particular interest include, but are not limited to, the anti-apoptotic proteins Bcl-xl and Mcl-1.

The bcl-2 gene, which encodes the mitochondrial membrane protein Bcl-2, was first identified in B-cell lymphomas (Tsujimoto et al. (1984) *Science* 226:1097) where the causal genetic lesion has been characterised as a chromosomal translocation (t(14:18)) that places the bcl-2 gene under the control of the immunoglobulin promoter. The resulting overexpression of Bcl-2 retards the normal course of apoptotic cell death that otherwise maintains B-cell homeostasis, resulting in B-cell accumulation and follicular lymphoma (Adams and Cory, 1998; Cory (1994) *Philos. Trans. R. Soc. Lond. B. Biol. Sci.* 345:289). Bcl-2 can exist as a homodimer or can form a heterodimer with bax. As a homodimer, bax functions to induce apoptosis. However, the formation of a bax-Bcl-2 complex blocks apoptosis. Bcl-2 expression may also play a role in the development of drug resistance.

Several genes with homology to the bcl-2 gene have subsequently been characterized, including the following: at, which encodes the 80-amino acid Al protein that is rapidly induced in macrophages in response to GM-CSF or LPS (Lin et al. (1993) *J. Immunol.* 151: 1979-1988); mcl-1, an early response gene in myeloid cell lines that undergo macrophage differentiation (Kozopas et al. (1993) *Proc. Natl. Acad. Sci. USA* 90:3516-3520); and bak, a bcl-2 homologue that may enhance apoptosis (Chittenden et al. (1995) *Nature* 374:733; Kiefer et al. (1995) *Nature* 374:736). Other proteins which interact with and/or are structurally related to the bcl-2 gene product have also been identified, such as for example, Bcl-xl, and Bcl-xs (Boise et al. (1993) *Cell* 74:597); Ced-9 (Vaux et al. (1992) *Science* 258:1955).

The bcl-x gene product, Bcl-x, which is closely related to the Bcl-2 protein, also protects cells from apoptosis. Alternative splicing of human Bcl-x may result in at least two distinct Bcl-x mRNA species, Bcl-xl and Bcl-xs. The predominant protein product (233 amino acids) of the larger bcl-x mRNA, Bcl-xl, inhibits cell death upon growth factor withdrawal (Boise et al. (1993) *Cell* 74:597-608) and its transgenic expression alters thymocyte maturation leading to increased numbers of mature thymocytes (Chao et al. (1995) *J. Exp. Med.* 182:821-828; Grillot et al. (1995) *J. Exp. Med.* 182: 1973-1983).

The myeloid cell leukemia associated gene mcl-1 encodes a protein, Mcl-1, that is expressed early during the programming of differentiation in myeloid cell leukemia (see, for example, U.S. Patent Application Publication No. 20020086321). The carboxyl portion of Mcl-1 shares homology to Bcl-2. Like other members of the Bcl-2 family, Mcl-1 is characterized by an association with the programming of transitions in cell fate, such as from viability to death or from proliferation to differentiation.

In addition to members of the Bcl-2 family, cell survival biomarkers for use in the methods of the present invention include members of the gene family of inhibitors of apoptosis related to the baculovirus IAP gene (Bimbaum et al. (1994) *J. Virol.* 68:2521-2528; Clem et al. (1994) *Mol. Cell Biol.* 14:5212-5222; Duckett et al. (1996) *EMBO J.* (1996) 15:2685-2694; Hay et al. (1995) *Cell* 83:1253-1262; Liston et al. (1996) *Nature* 379:349-353; Rothe et al. (1995) *Cell* 83:1243-1252; Roy et al. (1995) *Cell* 80:167-178). At least eight human IAPs have been identified (Salvesen and Duckett (2002) *Nat. Rev. Mol. Cell. Biol.* 3:401-410).

The IAPs are highly conserved evolutionarily; they share a similar architecture organized in one to three approximately 70 amino acid amino terminus Cys/His baculovirus IAP repeats (BIR) and by a carboxy terminus zinc-binding domain, designated RING finger. The IAP family proteins are recognized as having potentially important roles in the regulation of apoptosis and tumorigenesis (Deveraux and Reed (1999) *Genes Dev.* 13:239-252; Tamm et al. (2000) *Clin. Cancer Res.* 6:1796-1803).

The IAPs suppress cell death by inhibiting upstream and terminal caspases (see, for example, Thompson (1995) *Science* 267:1456). The active (i.e., cleaved) forms of Caspase-3 and -7 are directly inhibited by XIAP, c-IAP1, and c-IAP2 (see, for example, Roy et al. (1997), supra), which can also prevent the proteolytic processing of pro-Caspase-3, -6, and -7 by blocking the cytochrome c-induced activation of pro-Caspase-9 (Deveraux et al. (1998) *EMBO J.* 17:2215-2223). Therapeutic and diagnostic uses of nucleic acids that encode various inhibitors of apoptosis relating to a member of the IAP family have been described in the patent literature. See, for example, International Patent Applications No. WO 97/06255, WO 97/26331, and WO 97/32601. Examples of IAP proteins that can be used as biomarkers of cell survival include, but are not limited to, XIAP, cIAP1, cIAP2, and survivin.

XIAP is the most widely expressed and most potent inhibitor of caspases (see, for example, Takahasi et al. (1998) *J. Biol. Chem.* 273:7787; Reed (1994) *J. Cell Biol.* 124: 1). Survivin is an approximately 16.5 kDa cytoplasmic protein (see, for example, U.S. Patent Application Publication No. 20030100525) containing a single BIR, and a highly charged carboxyl-terminus coiled-coil region instead of a RING finger, which inhibits apoptosis induced by growth factor (IL-3) withdrawal when transferred in B cell precursors (Ambrosini et al. (1997) *Nature Med.* 3:917-921). Overexpression of exogenous survivin protein rescues cells from p53-induced apoptosis in a dose-dependent manner, suggesting that loss of survivin mediates, at least, in part the p53-dependent apoptotic pathway (Mirza et al. (2002) *Oncogene* 21:2613-2622).

Another representative biomarker of cell survival for use in the methods of the invention is TRAF-1. The TRAF family members bind to the cytoplasmic domain of CD40 and mediate activation of multiple signaling pathways that regulate B-cell survival, proliferation, differentiation, isotype switching, development of the germinal center, and the humoral memory response (see, for example, Pullen et al. (1999) *J. Biol. Chem.* 274:14246-14254). It has been reported that activation of the CD40 receptor can result in transcription of the TRAF-1 gene (Schwenzer et al. (1999) *J. Biol. Chem.* 274(27):19368-19374) and strong upregulation of TRAF-1 expression in human monocytes (Pearson et al. (2001) *Internat. Immunol.* 13(3):273-283). Changes in TRAF-1 gene expression in response to CD40 receptor activation may be predictive of drug efficacy, thereby providing a suitable biomarker for assessing and/or monitoring the effects of anti-CD40 therapeutics on CD40L-mediated CD40 signaling and modulation of cell survival/apoptosis. Changes in TRAF-1 expression can be easily detected at either the mRNA level by techniques such as Northern blot or quantitative RT-PCR or the protein level, for example, by Western blot, as noted herein below.

The foregoing biomarkers of cell survival can be monitored in the ex vivo prognostic assays described herein in any combination, including one or all of these biomarkers, as well as in combination with other biomarkers of cellular proliferation. Thus in one embodiment, the ex vivo prognostic assays described herein are also used to monitor in a test biological sample from a candidate subject the expression of the cell proliferation biomarker Ki67.

Ki67 is a cell cycle related nuclear protein that is present in the nuclei of cells in the G1, S, M and G2 phases of dividing cells, but not in the G0 phase of quiescent cells (Gerdes et al. (1984) *J. Immunol.* 133, 1710-1715). For these reason, it is used as a cell proliferation marker.

Thus the biomarkers that are to be monitored in the ex vivo prognostic assays of the present invention include the cell survival and apoptotic proteins described above, and proteins involved in the CD40 signaling pathways as noted herein above. Monitoring can be at the protein or nucleic acid level. Thus, the biomarkers include these proteins and the genes encoding these proteins. Where detection is at the protein level, the biomarker protein comprises the full-length polypeptide or any detectable fragment thereof, and can include variants of these protein sequences. Similarly, where detection is at the nucleotide level, the biomarker nucleic acid includes DNA comprising the full-length coding sequence, a fragment of the full-length coding sequence, variants of these sequences, for example naturally occurring variants or splice-variants, or the complement of such a sequence. Biomarker nucleic acids also include RNA, for example, mRNA, comprising the full-length sequence encoding the biomarker protein of interest, a fragment of the full-length RNA sequence of interest, or variants of these sequences. Biomarker proteins and biomarker nucleic acids also include variants of these sequences. By "fragment" is intended a portion of the polynucleotide or a portion of the amino acid sequence and hence protein encoded thereby. Polynucleotides that are fragments of a biomarker nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs known in the art. The protein and corresponding coding sequence for each of these markers is known in the art. See Table 6 in Example 3 herein below.

CD40-Related Factors and Clinically Useful Prognostic Markers for Use in Other Prognostic Assays.

In accordance with the methods of the present invention, individuals or subpopulations of patients having an inflammatory disease or autoimmune disease that would benefit from treatment with anti-CD40 therapeutic agents can also be identified using prognostic assays that look for the presence or absence of, or elevated or diminished levels of, one or more CD40-related factors Subjects identified as being responsive to treatment with an anti-CD40 therapeutic agent on the basis of these CD40-related factors can be treated with the anti-CD40 therapeutic agent. Alternatively, they can be further screened for potential benefit from treatment with anti-CD40 therapeutic agents using the ex vivo prognostic assays described herein, for example, to identify whether the inflammatory disease or autoimmune disease would be more responsive to treatment with an anti-CD40 therapeutic agent that blocks CD40L-mediated CD40 signaling or which modulates ADCC activity, or which has both of these modes of action.

CD40-related factors of interest include, but are not limited to, expression level of cell surface CD40 antigen, expression level of cell surface CD40L, circulating levels of soluble CD40 (sCD40), and circulating levels of soluble CD40L (sCD40L). In this manner, a biological sample collected from a candidate subject is analyzed for expression level of at least one of these CD40-related factors. The expression level of these CD40-related factors may be used as prognostic markers for autoimmune diseases and/or inflammatory diseases. They may be useful as diagnostics of subjects who would or would not respond to anti-CD40 therapeutic agents.

Any method known in the art can be used for analysis of these markers. Circulating levels of sCD40 or sCD40L, for example, in a blood sample obtained from a candidate subject, can be measured, for example, by ELISA, radioimmunoassay (RIA), electrochemiluminescence (ECL), Western blot, multiplexing technologies, or other similar methods. Cell surface expression of CD40 or CD40L can be measured, for example, by flow cytometry, immunohistochemistry, Western Blot, immunoprecipitation, magnetic bead selection, and quantification of cells expressing either of these cell surface markers. CD40 and CD40L RNA expression levels could be measured by RT-PCR, Qt-PCR, microarray, Northern blot, or other similar technologies. The sequences for the CD40 antigen, CD40L, and soluble CD40L are known in the art. See, for example, Table 7 in Example 3 herein below. In some embodiments, the sCD40 is isolated and sequenced to ascertain a distinction between sCD40 that is secreted by the CD40-expressing cells versus sCD40 that is proteolytically cleaved from the surface of these cells. Expression level of secreted sCD40 and/or proteolytically cleaved sCD40 can be correlated to disease state and/or to responsiveness of the disease to treatment with an anti-CD40 therapeutic agent of interest.

In other embodiments of the invention, subpopulations of patients having an inflammatory disease or autoimmune disease that would benefit from treatment with an anti-CD40 therapeutic agent are identified by screening candidate subjects for one or more clinically useful prognostic markers known in the art. Examples of clinically useful markers include, but are not limited to, serum interleukin (IL)-18, the levels of which relate to the severity of primary biliary cirrhosis (Yamano et al. (2000) *Clin. Exp. Immunol.* 122:227-231); soluble intercellular adhesion molecule-1 (ICAM-1), the expression of which is greater in late primary biliary cirrhosis than in early disease, and which correlates with histological progression (Lim et al. (1994) *Hepatology* 20:882-888); the cellular expression of cell adhesion molecules like ICAM-1 and CD40, which serve to predict the outcome of lupus nephritis (Daniel et al. (2001) *Kidney Int.* 60:2215-2221); serum soluble IL-2 receptor (sIL-2R) levels, which appear to be an excellent monitor of clinical disease activity in rheumatoid arthritis (RA) (Wood et al. (1988) *J. Autoimmun.* 1:353-361); intestinal multidrug resistance protein (MDR1), the level of which is a powerful prognostic indicator for the outcome of living-donor liver transplant (Hashida et al. (2001) *Clin. Pharmacol. Ther.* 69:308-316); serum leucine aminopeptidase, increased levels of which may be an activity indicator for systemic lupus erythematosus (Inokuma et al. (1999) *Rheumatology* (Oxford) 38:705-708); C-reactive protein, which is a general indicator of inflammation; and alpha 1-antitrypsin, which is an indicator of disease activity in Crohn's disease, colitis and ileitis (Meyers et al. (1985) *Gastroenterology* 89:13-18); the references of which are herein incorporated by reference in their entirety.

Thus, subpopulations of patients with autoimmune and/or inflammatory diseases that are less responsive to existing therapeutics can be readily identified by currently used assay methods, including prognostic assays disclosed herein that utilize one or more of these clinically useful prognostic markers. Having identified a subject that falls within one of these subpopulations based on these clinically useful prognostic markers, the subject can be further screened using one or more of the ex vivo prognostic assays identified herein above to assess the benefit of treating this subject with an anti-CD40 therapeutic that modulates CD40L-mediated CD40 signaling and/or ADCC activity.

Prognostic Assays

In some embodiments of the present invention, potential therapeutic benefit with an anti-CD40 therapeutic agent that modulates CD40L-mediated CD40 signaling, modulates ADCC, or both is assessed using ex vivo prognostic assays that monitor changes in the expression level of one or more of the aforementioned biomarkers of cell proliferation and survival, cellular apoptosis, and CD40 signaling pathways in a biological sample that is collected from a candidate subject that is in need of therapeutic intervention for an autoimmune disease and/or inflammatory disease that is mediated by stimulation of CD40 signaling on CD40-expressing cells. By "CD40-expressing cell" is intended cells expressing CD40 antigen. Methods for detecting CD40 expression in cells are well known in the art and include, but are not limited to, PCR techniques, immunohistochemistry, flow cytometry, Western blot, ELISA, and the like. Where the ex vivo assays generate a favorable change in the expression level of one or more biomarkers of interest within the biological sample, treatment intervention with the anti-CD40 therapeutic agent is warranted. Furthermore, the biomarkers, cytokine markers, and CD40-related factors discussed herein can be used to monitor treatment efficacy of an anti-CD40 therapeutic agent in a subject, who may or may not have been screened using the ex vivo prognostic assays disclosed herein, and thus determine whether further treatment with the same anti-CD40 therapeutic agent is warranted, or whether alternative treatment protocols are necessary or desirable. Where treatment with an anti-CD40 therapeutic agent is warranted as determined by the methods of the present invention, the therapeutic agent can be administered by any suitable route of administration.

The candidate subject who is being considered for treatment intervention with an anti-CD40 therapeutic agent that modulates CD40L-mediated CD40 signaling, modulates ADCC, or both can be afflicted with, or at risk of developing or relapsing with, any inflammatory or autoimmune disease that is mediated by CD40 signaling on CD40-expressing cells. Inflammatory diseases are characterized by inflammation and tissue destruction, or a combination thereof. "Inflammatory disease" includes any inflammatory immune-mediated process where the initiating event or target of the immune response involves non-self antigen(s), including, for example, alloantigens, xenoantigens, viral antigens, bacterial antigens, unknown antigens, or allergens.

Further, for purposes of the present invention, the term "inflammatory disease(s)" includes "autoimmune disease(s)." As used herein, the term "autoimmunity" is generally understood to encompass inflammatory immune-mediated processes involving "self" antigens. In autoimmune diseases, self antigen(s) trigger host immune responses.

Also, the methods of the present invention can be used to assess the efficacy of an anti-CD40 therapeutic agent for treatment of inflammation associated with tissue transplant rejection. "Transplant rejection" or "graft rejection" refers to any host-mounted immune response against a graft including but not limited to HLA antigens, blood group antigens, and the like.

The invention can also be used to assess the efficacy of an anti-CD40 therapeutic agent for treatment of graft versus host disease, such as that associated with bone marrow transplantation, for example. In such graft versus host disease, the donor bone marrow includes lymphocytes and cells that mature into lymphocytes. The donor's lymphocytes recognize the recipient's antigens as non-self and mount an inflammatory immune response. Hence, as used herein, "graft versus host disease" or "graft versus host reaction" refers to any T cell mediated immune response in which donor lymphocytes react to the host's antigens.

Examples of autoimmune and/or inflammatory disorders include, but are not limited to, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1, 2, 3, and 4 delayed-type hypersensitivity, allergy or allergic disorders, unwanted/unintended immune responses to therapeutic proteins (see for example, U.S. Patent Application No. US 2002/0119151 and Koren, et al. (2002) Curr. Pharm. Biotechnol. 3:349-60), asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like. In some other embodiments, the methods of the present invention are used to identify individuals who would benefit from treatment with an anti-CD40 therapeutic agent for pulmonary inflammation, including, but not limited to, lung graft rejection, asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, bronchiolitis obliterans due to bone marrow and/or lung transplantation or other causes, graft atherosclerosis/graft phlebosclerosis, as well as pulmonary fibrosis resulting from collagen, vascular, and autoimmune diseases such as rheumatoid arthritis and lupus erythematosus.

In other embodiments, the methods of the invention are useful for identifying and treating autoimmune diseases and inflammatory diseases that are initially resistant to, or which develop resistance to other known therapeutic treatments whose mode of action is other than through modulation of CD40L-mediated CD40 signaling, modulation of ADCC, or both. The ex vivo prognostic assays can be used to identify subpopulations of patients for whom treatment intervention with one or more anti-CD40 therapeutic agents that modulates CD40L-mediated CD40 signaling, modulates ADCC, or both is desirable.

The term "prognosis" is recognized in the art and encompasses predictions about the likely course of response to therapeutic intervention, and the likely course of disease or disease progression, particularly with respect to likelihood of disease remission, disease relapse, and death. The ex vivo prognostic assays of the present invention can be used to predict the response of a candidate subject to a particular anti-CD40 therapeutic agent, or class of anti-CD40 therapeutic agents, that modulates CD40L-mediated CD40 signaling, modulates ADCC, or both. By "predicting the response of a candidate subject" is intended assessing the likelihood that a subject in question will experience a positive or negative outcome with a particular anti-CD40 therapeutic agent. For purposes of the present invention, "indicative of a positive treatment outcome" in the context of the ex vivo prognostic assays of the present invention is intended to mean an increased likelihood that the candidate subject will experience beneficial results in response to treatment with the anti-CD40 therapeutic agent under consideration, and thus treatment intervention with that anti-CD40 therapeutic agent would be warranted. In contrast, "indicative of a negative treatment outcome" is intended to mean an increased likelihood that the patient will not benefit from treatment intervention with the anti-CD40 therapeutic agent under consideration, and thus treatment intervention with that anti-CD400 therapeutic agent would not be warranted.

Beneficial results that can be achieved with treatment intervention with anti-CD40 therapeutic agents that modulate CD40L-mediated CD40 signaling include any positive therapeutic response. By "positive therapeutic response" with respect to an autoimmune disease and/or inflammatory disease is intended an improvement in the disease in association with the anti-inflammatory activity of these antibodies or antigen-binding fragments thereof, and/or an improvement in the symptoms associated with the disease. That is, an anti-proliferative effect, the prevention of further proliferation of the CD40-expressing cell, a reduction in the inflammatory response including but not limited to reduced secretion of inflammatory cytokines, adhesion molecules, proteases, immunoglobulins (in instances where the CD40 bearing cell is a B cell), combinations thereof, and the like, increased production of anti-inflammatory proteins, a reduction in the number of autoreactive cells, an increase in immune tolerance, inhibition of autoreactive cell survival, and/or a decrease in one or more symptoms mediated by stimulation of CD40-expressing cells can be observed. Such positive therapeutic responses are not limited to the route of administration and may comprise administration to the donor, the donor tissue (such as for example organ perfusion), the host, any combination thereof, and the like.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-CD40 therapeutic agent may experience the beneficial effect of an improvement in the symptoms associated with the disease.

In some embodiments, the ex vivo prognostic assays for use in the methods of the present invention comprise providing a test biological sample and a control biological sample from a candidate subject in need of prognosis for treatment intervention with an anti-CD40 therapeutic agent as noted herein, where the test and control biological samples comprise CD40-expressing cells that have been stimulated with a CD40 ligand, either in vivo or ex vivo; contacting the test biological sample with an effective amount of the anti-CD40 therapeutic agent of interest; detecting the level of at least one biomarker in this test biological sample, where the biomarker is selected from the group consisting of a biomarker of cellular apoptosis, a biomarker of a CD40L-mediated CD40 signaling pathway, and a biomarker of cell survival, depending upon the mode of action of the anti-CD40 therapeutic agent of interest; and comparing the level of the biomarker(s) in the test biological sample to the level of the biomarker(s) in the control biological sample, which has not been contacted with the anti-CD40 therapeutic agent. Where the anti-CD40 therapeutic agent is an antagonist that blocks or interferes with CD40L-mediated CD40 signaling, or blocks or interferes with this signaling and also modulates ADCC, the ex vivo prognostic assays disclosed herein for any or all of these biomarkers of cell proliferation and survival, apoptosis, and CD40L-mediated CD40 signaling, can be used to assess the potential beneficial effect of the therapeutic agent, alone or in combination with assays for cytokine markers that are upregulated by CD40L-mediated CD40 signaling, and/or assays for one or more of the CD40-related factors described herein, in order to identify a subject having an inflammatory disease or autoimmune disease that would be responsive to treatment with that anti-CD40 therapeutic agent. Where the anti-CD40 therapeutic agent has its mode of action via modulating ADCC activity, for example, an anti-CD40 antibody, the ex vivo prognostic assay for one or more markers of apoptosis can be used to assess the potential beneficial effect of the therapeutic agent, alone or in combination with assays for one or more of the CD40-related factors described herein, in order to identify a subject having an inflammatory disease or autoimmune disease that would be responsive to treatment with that anti-CD40 therapeutic agent.

In accordance with the ex vivo prognostic assays of the invention, expression level of one or more biomarkers, and optionally one or more cytokine markers, in a test biological sample that is contacted with the anti-CD40 therapeutic agent of interest is compared to expression level for the biomarker(s), and optionally cytokine marker(s) in a control biological sample. By "test biological sample" is intended a biological sample comprising CD40-expressing cells obtained from the candidate subject, and which will be contacted with the anti-CD40 therapeutic agent under consideration for treatment of the candidate subject. By "control biological sample" is intended a biological sample that is comparable to the test biological sample in that it also comprises approximately the same number and kind of CD40-expressing cells and has been obtained from the candidate subject in the same timeframe and in a manner equivalent to that used to obtain the test biological sample, and which will be subjected to the same experimental conditions as the test sample, but which will not be contacted with the anti-CD40 therapeutic agent of interest. The test biological sample and control biological sample can be provided from a single biological sample that has been obtained from the subject and divided into subsamples, one of which is designated the test biological sample and another of which is designated the control biological sample. Alternatively, the test biological sample and control biological sample can be provided from two or more biological samples, which can be pooled and then subdivided into subsamples as above, or which can individually represent the test and control biological samples.

While it is recognized that the CD40-expressing cells obtained from the candidate subject may have been constitutively stimulated by CD40L in vivo prior to the collection of a biological sample, it is preferable to stimulate the CD40-expressing cells of the test and control biological samples ex vivo so that antagonistic effects of an anti-CD40 therapeutic agent on CD40-related activities, for example, stimulation of cell proliferation and CD40 signaling, can effectively be assessed.

In this manner, prior to contacting the test biological sample of CD40-expressing cells with the anti-CD40 therapeutic agent of interest, the CD40-expressing cells within any given biological sample collected from the candidate subject can be stimulated, for example, with CD40L, to ensure upregulation of CD40 signaling on the CD40-expressing cells of the test and control biological samples to be used in the ex vivo prognostic assay. Any source of CD40L can be used, including, but not limited to, soluble CD40L. Other suitable CD40-stimulatory molecules can include, for example, agonist antibodies that bind specifically to the extracellular domain of CD40. Thus, in some embodiments, suitable CD40-stimulatory molecules include, but are not limited to, membrane-bound CD40L (for example, CD40L bound to the plasma membrane of a cell, for example, formaldehyde-fixed CHO cells transfectant-expressing CD40L; or CD40L incorporated into a synthetic lipid-based substrate such as a liposome or micelle), soluble CD40L, an agonist anti-CD40 antibody, for example, the anti-human CD40 antibody G28-5 (Bristol-Myers Squibb, Seattle, Wash.), and mixtures thereof. An effective amount of a stimulatory molecule to be contacted with cells of a collected biological sample or subsample thereof in order to stimulate one or more CD40 signaling pathways will depend upon factors such as the type of ligand used (e.g., monomeric or multimeric; solubility and permeability, and the like) and the abundance of the CD40 receptor on the CD40-expressing cells. Preferably, between about 1.0 nM and about 1 mM of CD40L or soluble CD40L is used to stimulate CD40 signaling.

In some embodiments, CD40-expressing cells within the biological sample or subsample thereof are stimulated with soluble recombinant human CD40L (Alexis Corporation, Bingham, Nottinghamshire, UK) prior to the contacting step by incubating the biological sample or subsample thereof with soluble CD40L for a time sufficient to stimulate CD40 signaling. In some embodiments, the incubation time is about 10 minutes to about 4 hours. The amount of soluble CD40L present during the incubation period is readily determined by titration. In one embodiment, the amount of soluble CD40L is about 1 µg/ml. Any acceptable protocol to contact the test biological sample with an anti-CD40 therapeutic agent of interest can be used in the ex vivo prognostic assays of the invention. Factors to be considered include, but are not limited to, the number of cells to be contacted within a container comprising the biological sample or subsample thereof; the concentration of the anti-CD40 therapeutic agent to be contacted with the test biological sample; the incubation time of the anti-CD40 therapeutic agent with the cells in the test biological sample; where applicable, the concentration of a stimulatory molecule, for example, CD40L, soluble CD40L, or stimulatory fragment or variant thereof, to be contacted with the test biological sample; and, where applicable, the incubation time of the stimulatory molecule with the cells in the test biological sample. Determination of such factors can be accomplished by those skilled in the art based on variables such as the type of biological sample being tested, size of the holding container, the volume of liquid in the container, and the chemical composition of the anti-CD40 therapeutic agent (i.e., size, charge, and the like) being tested.

In one embodiment, a test biological sample or subsample thereof comprising a suitable number of CD40-expressing cells is added to a 96-well tissue culture dish. The suitable number of cells is a number of cells that enables one to detect a change in one or more of the CD40-mediated activities (i.e., cell proliferation and cell survival, level of apoptosis, CD40 signaling pathways) using one or more of the detection methods described elsewhere herein. In some embodiments, the suitable number of cells is between about 1 and about $1 \times 10^6$ cells per well of a 96-well tissue culture dish. Following addition of the cells to the tissue culture dish, the cells can be preincubated between about 0 to about 96 hours before contacting the cells with the anti-CD40 therapeutic agent. In some embodiments, the cells are preincubated with a CD40-stimulatory molecule as noted herein above.

An effective amount of an anti-CD40 therapeutic agent is added to the cells of the test biological sample to provide for regulation of a CD40-mediated activity of interest (i.e., CD40L-mediated CD40 signaling, ADCC activity of an agent that binds to CD40, or both) such that the regulation is detectable using one or more detection methods disclosed elsewhere herein. The effective amount will of course be dependent upon the anti-CD40 therapeutic agent being tested. Generally, an effective amount of an anti-CD40 therapeutic agent is between about 1 nM to about 10 mM of the agent per well of a 96-well plate. In one embodiment, the anti-CD40 therapeutic agent is an antagonist anti-CD40 antibody, for example, the CHIR-12.12 or CHIR-5.9 fully human monoclonal antibody, or antigen-binding fragment thereof, and the effective amount is about 0.01 µg/ml to about 30 µg/ml, including about 0.01 µg/ml, 0.1 µg/ml, 0.5 µg/ml, 1 µg/ml, 5 µg/ml, 10 µ/ml, 20 µg/ml, and 30 µg/ml, and other such values between about 0.01 µg/ml and about 30 µg/ml. The cells within the test biological sample or subsample thereof are allowed to incubate for a suitable length of time to allow the anti-CD40 therapeutic agent to interact with the cells and generate one or more biological responses. In some embodiments, the preferred incubation time between the anti-CD40 therapeutic agent and the cells of the test biological sample or subsample thereof is between about 1 minute to about 48 hours. In other embodiments, the incubation time is about 20 minutes, about 30 minutes, about 1 hour, about 4 hours, about 12 hours, about 22 hours, or about 24 hours.

The biological sample(s) that serve(s) as the test and control biological samples can be any collection of cells, tissue, or bodily fluid that comprises cells expressing the CD40 antigen. Examples of such biological samples include, but are not limited to, blood, lymph, tissue samples, smears, and the like. Biological samples can be collected from a candidate subject using any acceptable procedure in the art, for example, by needle aspiration of bodily fluids, removal of a tissue sample, and the like. Where a biological sample must be stored prior to assay, the biological sample can be transferred to a glass slide or may be frozen for later preparation or immediately placed in a fixative solution.

As previously noted, detection of the biomarker of interest at the protein or nucleotide level can be accomplished using any detection method known to those of skill in the art. By "detecting expression" or "detecting the level of" is intended determining the quantity or presence of a biomarker protein or gene in the biological sample. Thus, "detecting expression" encompasses instances where a biomarker is determined not to be expressed, not to be detectably expressed, expressed at a low level, expressed at a normal level, or overexpressed. In order to determine the effect of an anti-CD40 therapeutic agent on CD40L-mediated CD40 signaling, a test biological sample comprising CD40-expressing cells that have been stimulated with a CD40 ligand (either in vivo or ex vivo) is contacted with the anti-CD40 therapeutic agent for a sufficient time to allow the therapeutic agent to exert a cellular response, and then expression level of one or more biomarkers of interest in that test biological sample is compared to the expression level in the control biological sample that has not been contacted with the anti-CD40 therapeutic agent. In some embodiments, the control biological sample of cells is contacted with a neutral substance or negative control that does not interfere with CD40L-mediated CD40 signaling. For example, in one embodiment, a non-specific immunoglobulin, for example IgG1, that does not bind to CD40 serves as the negative control. Detection can occur over a time course to allow for monitoring of changes in biomarkers over time. Detection can also occur with exposure to different concentrations of the anti-CD40 therapeutic agent to generate a "dose-response" curve for any given biomarker of interest.

Methods for detecting expression of the biomarkers of the invention, and optionally cytokine markers, within the test and control biological samples comprise any methods that determine the quantity or the presence of the markers either at the nucleic acid or protein level. Such methods are well known in the art and include but are not limited to western blots, northern blots, ELISA, immunoprecipitation, immunofluorescence, flow cytometry, immunohistochemistry, nucleic acid hybridization techniques, nucleic acid reverse transcription methods, and nucleic acid amplification methods. In particular embodiments, expression of a biomarker is detected on a protein level using, for example, antibodies that are directed against specific biomarker proteins. These antibodies can be used in various methods such as Western blot, ELISA, multiplexing technologies, immunoprecipitation, or immunohistochemistry techniques. In some embodiments, detection of cytokine markers is accomplished by electrochemiluminescence (ECL). Any of these detection methods for biomarkers and optionally cytokine markers can be combined with assessment of clinical information, conventional prognostic methods, expression of other CD40-related factors, particularly expression of cell-surface CD40 and/or CD40L and circulating levels of soluble CD40 and/or CD40L, and expression of, or presence of, clinically useful prognostic markers known in the art, including, but not limited to, those noted herein above. In this manner, the disclosed methods may permit the more accurate determination of candidate subjects whose autoimmune disease or inflammatory disease would benefit from therapeutic intervention with an anti-CD40 therapeutic agent described herein.

Thus, in some embodiments, a candidate subject having an inflammatory or autoimmune disease that is associated with CD40-expressing cells is tested for responsiveness to an anti-CD40 therapeutic agent of interest using the ex vivo prognostic assays described herein, wherein effects of the therapeutic agent on one or more CD40-mediated activities is assessed. Where further refinement of the ex vivo prognostic assay is desirable, the candidate subject can be examined for the level of expression of, or absence of expression of, one or more CD40-related factors identified herein above, one or more clinically useful prognostic markers, including those identified herein above, or both. In this manner, a biological sample comprising CD40-expressing cells can be collected from a candidate subject and assessed for the level of expression of, or absence of expression of, the CD40-related factor(s) and/or clinically useful prognostic marker(s) of interest. Any biological sample comprising CD40-expressing cells as noted herein above can be collected for these prognostic assays. Further, any detection method known to those of skill in the art can be used to detect the level of expression, or absence of expression, of the CD40-related factor(s) and/or clinically useful prognostic marker(s) of interest, as noted elsewhere herein.

Where the expression level of one or more CD40-related factors is to be assessed in order to identify a subject having an inflammatory disease or autoimmune disease that will be responsive to treatment with an anti-CD40 therapeutic agent, a biological sample is collected from the subject, and the level of expression in that sample is compared to the level of expression of that factor (or factors) in a control or reference standard. For expression level of cell-surface CD40 and/or cell-surface CD40L, any biological sample comprising CD40-expressing and/or CD40L-expressing cells can be used as noted herein above. For circulating levels of sCD40 and/or sCD40L, a blood sample or sample comprising a blood component such as plasma or serum can be obtained from the candidate subject. By "control" or "reference standard" is intended a standard that is of the same biological source (i.e., tissue or bodily fluid) and which distinguishes subjects having the inflammatory or autoimmune disease from healthy subjects that are not afflicted with the disease. A skilled artisan can provide a reference standard by taking a measurement of expression levels of these CD40-related factors (i.e., cell-surface CD40, cell-surface CD40L, sCD40, sCD40L) in healthy subjects that do not have the disease and subjects that do have the disease, controlling for age, sex, race, and the like, and comparing the expression levels to determine the standard level of expression to be expected in a healthy subject. In some embodiments, the expression level in the candidate subject having the inflammatory or autoimmune disease is at least 20%, 30%, 40%, 50%, 60%, 70%, 80%, 100%, 150%, 200%, 250%, 300% greater than the expression level in the reference standard. It is recognized that the applicability of treatment with an anti-CD40 therapeutic agent can be assessed by detecting the level of expression of one or more of these CD40-related factors, wherein an increased level of expression in a biological sample relative to the reference standard is sufficient to establish that the subject has an inflammatory or autoimmune disease that will be responsive to treatment with the anti-CD40 therapeutic agent of interest without having to do additional screening for ex vivo effects of the anti-CD40 therapeutic agent on CD40-mediated activities such as cell survival and proliferation, and/or ADCC activity.

The present invention also encompasses kits for carrying out the ex vivo prognostic assays of the present invention. For example, the kit can comprise a labeled compound or agent capable of detecting a biomarker described herein, e.g., a biomarker of apoptosis, cellular proliferation or survival, or a CD40L-mediated CD40 signaling pathway, either at the protein or nucleic acid level, in a biological sample and means for determining the amount of the biomarker in the sample (for example, an antibody or an oligonucleotide probe that binds to RNA encoding a biomarker of interest) following incubation of the sample with an anti-CD40 therapeutic agent of interest. Kits can be packaged to allow for detection of multiple biomarkers of interest by including individual labeled compounds or agents capable of detecting each individual biomarker of interest and means for determining the amount of each biomarker in the sample. Kits can also include instructions for treating a subject when the ex vivo prognostic assay generates a result that is indicative of a positive treatment outcome with the anti-CD40 therapeutic agent.

For antibody-based kits, the kit can comprise, for example: (1) a first antibody (e.g., attached to a solid support) that binds to a biomarker of interest; and, optionally, (2) a second, different antibody that binds to the biomarker or the first antibody and is conjugated to a detectable agent. For oligonucleotide-based kits, the kit can comprise, for example: (1) an oligonucleotide, e.g., a detectably labeled oligonucleotide, that hybridizes to a nucleic acid sequence encoding the biomarker or (2) a pair of primers useful for amplifying a nucleic acid molecule encoding the biomarker of interest. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is a candidate for treatment with the anti-CD40 therapeutic agent.

Detection Methods

Any means for specifically identifying and quantifying a biomarker, cytokine marker, or CD40-related factor protein of interest (for example, a biomarker of cell survival or proliferation, a biomarker of apoptosis, a biomarker of a CD40L-mediated CD40 signaling pathway, circulating soluble CD40 or CD40L, cell-surface CD40 or CD40L, or a clinically useful prognostic marker) in the biological sample of a candidate subject is contemplated. Thus, in some embodiments, expression level of a biomarker protein of interest in a biological sample is detected by means of a binding protein capable of interacting specifically with that biomarker protein or a biologically active variant thereof. Preferably, labeled antibodies, binding portions thereof, or other binding partners may be used. The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. The antibodies for detection of a biomarker protein may be monoclonal or polyclonal in origin, or may be synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols can be found in numerous texts in the art (see, for example, Ausubel et al., eds. (1995) *Current Protocols in Molecular Biology*) (Greene Publishing and Wiley-Interscience, NY)); Coligan et al., eds. (1994) *Current Protocols in Immunology* (John Wiley & Sons, Inc., New York, N.Y.).

A variety of assays are available for detecting proteins with labeled antibodies. In a one-step assay, the target protein of interest to be detected, if it is present, is immobilized and incubated with a labeled antibody. The labeled antibody binds to the immobilized target protein molecule. After washing to remove unbound molecules, the sample is assayed for the presence of the label. In a standard format, a single protein is assayed per sample. Using newer multiplex technologies, multiple proteins can be assayed in a single sample by using different labels for each detecting antibody.

In a two-step assay, the immobilized target protein molecule of interest is incubated with an unlabeled antibody. The target protein-unlabeled antibody complex, if present, is then bound to a second, labeled antibody that is specific for the unlabeled antibody. The sample is washed and assayed for the presence of the label.

The choice of marker used to label the antibodies will vary depending upon the application. However, the choice of the marker is readily determinable to one skilled in the art. These labeled antibodies may be used in immunoassays as well as in histological applications to detect the presence of any biomarker or protein of interest. The labeled antibodies may be polyclonal or monoclonal. Further, the antibodies for use in detecting a protein of interest may be labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that can serve as detectable labels include, for example, I-131, I-123, I-125, Y-90, Re-188, Re-186, At-211, Cu-67, Bi-212, and Pd-109. Examples of enzymes that can serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Examples of suitable ligand-receptor pairs are biotin-avidin or biotin-streptavidin, and antibody-antigen.

In some embodiments, the present invention contemplates the use of a sandwich technique for detecting one or more biomarkers, or other proteins of interest as noted herein above, in serum and other biological fluids. As described in International Publication No. WO 93/09437, such a technique uses two antibodies capable of binding the protein of interest: e.g., one of which is free in solution but labeled with a detectable chemical compound, the other of which is immobilized onto a solid support. Examples of chemical labels that may be used for the second antibody include but are not limited to radioisotopes, fluorescent compounds, and enzymes or other molecules that generate colored or electrochemically active products when exposed to a reactant or enzyme substrate. When samples containing the biomarker or other protein of interest are placed in this system, the biomarker or other protein of interest binds to both the immobilized antibody and the labeled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used.

Biological samples can be screened individually; alternatively, numerous samples of biological fluids can be screened at the same time, for example, using the conventional 96-well microtiter format, which is widely used and easily automatable. There are also several commercially available spectrometers ("plate readers") for calorimetrically analyzing 96-well plates. Further, biological samples can be screened for one biomarker, or multiple markers, for example, a panel of biomarkers, using methods well known in the art.

In preferred embodiments, expression of one or more biomarkers or other proteins of interest within a biological sample, for example, a sample of bodily fluid, is detected by radioimmunoassays or enzyme-linked immunoassays (ELISAs), competitive binding enzyme-linked immunoassays, dot blot (see, for example, *Promega Protocols and Applications Guide* (2$^{nd}$ ed.; Promega Corporation (1991), Western blot (see, for example, Sambrook et al. (1989) *Molecular Cloning, A Laboratory Manual*, Vol. 3, Chapter 18 (Cold Spring Harbor Laboratory Press, Plainview, N.Y.), chromatography, preferably high performance liquid chromatography (HPLC), or other assays known in the art. Thus, the detection assays can involve steps such as, but not limited to, immunoblotting, immunodiffusion, immunoelectrophoresis, or immunoprecipitation.

For any given protein detection assay, the biological sample, or a subsample thereof comprising CD40-expressing cells, is contacted with the binding partner, for example, the antibody, or detectably labeled antibody, for the biomarker or other protein of interest, for a time sufficient to permit the formation of antibody-antigen complexes, and then antibody binding is detected, for example, by any means noted herein above. Antibodies and detectably labeled antibodies to the biomarkers, CD40-related factors, and clinically useful prognostic markers described herein are well known in the art and commercially available. See, for example, antibodies specific to biomarkers of apoptosis, cell survival, and CD40 signaling pathways, as well as clinically useful prognostic markers, available, for example, from Cell Signaling Technology, Beverly, Mass.; DAKO, Copenhagen, Denmark; and the like. Alternatively, antibodies, or detectably labeled forms of these antibodies, can be generated using antibody production methods well known in the art, and further described herein below.

A number of assay kits for biomarkers of caspases are commercially available. For example, the Homogeneous Caspases Assay (Roche Applied Sciences, Indianapolis, Ind.), is a fluorimetric assay for the quantitative in vitro determination of caspase activity in microplates. The assay is particularly useful for high-throughput screening, allowing, for example, for 100 tests on 96-well plates, and 400 tests on 384-well plates (Cat. No. 3 005 372). This assay allows for detection of several caspases, including Caspase-2, Caspase-3, Caspase-7, and to a lesser extent, Caspase-6, Caspase-8, Caspase-9, and Caspase-10, in biological samples, including, for example, serum or plasma. The Cell Death Detection ELISA$^{PLUS}$ assay (Cat. No. 1 774 425; Roche Applied Sciences, Indianapolis, Ind.) is based on a quantitative sandwich-enzyme-immunoassay principle, using mouse monoclonal antibodies directed against DNA and histones, respectively. This assay allows the specific detection and quantitation of mono- and oligonucleosomes that are released into the cytoplasm of cells that die from apoptosis. It can be used for a variety of samples, including cell lysates, serum, culture supernatant, and the like.

Cell surface PS can be detected using any of the commercially available Annexin V staining reagents, which are based on the high affinity of annexin V for PS. See, for example, the Annexin V staining reagents commercially available from Roche Applied Science. By conjugating FITC to Annexin V it is possible to identify and quantitate apoptotic cells on a single-cell basis by flow cytometry. Staining cells simultaneously with FITC-Annexin V (green fluorescence) and the non-vital dye propidium iodide (red fluorescence) can provide for the discrimination of intact cells (FITC−PI−), early apoptotic (FITC+PI−), and late apoptotic or necrotic cells (FITC+PI+).

Further, elevated apoptosis within a biological sample can be confirmed with nucleic acid-based methods that detect the DNA fragmentation that is characteristic of apoptosis. When resolved using electrophoresis on agarose gels, apoptotic DNA initially has a characteristic "ladder" pattern, as opposed to a smear of nucleic acids that is observed, for example, in necrosis or other non-specific DNA degradation. A common histochemical technique to detect DNA fragmentation uses end-labeled DNA. Kits for such are commercially available, such as the APOLERT™ DNA fragmentation kit (Clontech Laboratories, Inc., Palo Alto, Calif.). This assay is based on terminal deoxynucleotidyltransferase (Tdt)-mediated dUTP nick-end labeling (TUNEL), where Tdt catalyzes the incorporation of fluorescein-dUTP at the free 3'-hydroxyl ends of fragmented DNA in cells undergoing apoptosis.

Any method known in the art can be used to detect production of cytokine markers. Standard assays comprise an ELISA format, where one cytokine is measured per sample. Alternatively, a more sensitive technology is electrochemiluminescence (ECL). In one embodiment, cytokine production is assayed using ECL, for example, using a multi-array system such as the commercially available Meso Scale Discovery® system for high performance cytokine assays (Meso Scale Discovery, Gaithersburg, Md.). Other formats that allow for measuring multiple cytokines (or other analytes) at once within a sample include the multiplex technologies. One such product is the Luminex® bead technology (Luminex Corporation, Austin, Tex.), in which up to 100 color-coded microspheres coated with reagents specific to a particular bioassay (such as an antibody to a cytokine) can be mixed together and analyzed using lasar technology.

The presence of one or more of the biomarkers, cytokines, CD40-related factors, and clinically useful prognostic markers described herein within a biological sample obtained from a candidate subject may also be determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA can be utilized for the purification of RNA (see, e.g., Ausubel et al., ed. (1987-1999) *Current Protocols in Molecular Biology* (John Wiley & Sons, New York). Additionally, large numbers of tissue samples can readily be processed using techniques well known to those of skill in the art, such as, for example, the single-step RNA isolation process disclosed in U.S. Pat. No. 4,843,155.

Thus, in some embodiments, the detection of a biomarker or other protein of interest is assayed at the nucleic acid level using nucleic acid probes. The term "nucleic acid probe" refers to any molecule that is capable of selectively binding to a specifically intended target nucleic acid molecule, for example, a nucleotide transcript. Probes can be synthesized by one of skill in the art, or derived from appropriate biological preparations. Probes may be specifically designed to be labeled, for example, with a radioactive label, a fluorescent label, an enzyme, a chemiluminescent tag, a calorimetric tag, or other labels or tags that are discussed above or that are known in the art. Examples of molecules that can be utilized as probes include, but are not limited to, RNA and DNA.

For example, isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, CD40-related factor, or clinically useful prognostic marker described herein above. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan can readily adapt known mRNA detection methods for use in detecting the level of mRNA encoding the biomarkers or other proteins of interest.

An alternative method for determining the level of a mRNA of interest in a sample involves the process of nucleic acid amplification, e.g., by RT-PCR (see, for example, U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression, or expression of a CD40-related factor or other clinically useful prognostic marker, is assessed by quantitative fluorogenic RT-PCR (i.e., the TaqMan® System).

Expression levels of an RNA of interest may be monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression may also comprise using nucleic acid probes in solution.

In one embodiment of the invention, microarrays are used to detect expression of one or more biomarkers, CD40-related factors, and/or clinically useful prognostic markers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation of an all-inclusive device. See, for example, U.S. Pat. Nos. 5,856,174 and 5,922,591, herein incorporated by reference.

In one approach, total mRNA isolated from the sample is converted to labeled cRNA and then hybridized to an oligonucleotide array. Each sample is hybridized to a separate array. Relative transcript levels may be calculated by reference to appropriate controls present on the array and in the sample.

Anti-CD40 Therapeutic Agents

The ex vivo prognostic assays described herein can be used to identify subjects having an inflammatory disease and/or autoimmune disease associated with CD40-expressing cells who would benefit from treatment with any anti-CD40 therapeutic agent of interest. Of particular interest are anti-CD40 therapeutic agents that modulate CD40L-mediated CD40 signaling and/or modulate ADCC. Such anti-CD40 therapeutic agents include, but are not limited to, antagonist anti-CD40 antibodies that block or interfere with CD40L-mediated signaling and/or modulate ADCC activity when bound to CD40, CD40L antagonists, including anti-CD40L antibodies, mutated forms of CD40L that can bind to CD40 but which do not trigger CD40 signaling, soluble CD40, soluble forms of fusion proteins comprising CD40, and pharmacologic agents that disrupt or interfere with CD40L-CD40 interaction and/or interfere with CD40 signaling, for example, the CD40:CD40L binding interruptor compounds disclosed in U.S. Patent Application Publication No. 20040067982, herein incorporated by reference in its entirety. Of particular interest are antagonist anti-CD40 therapeutic agents, for example, antagonist anti-CD40 antibodies and antagonist anti-CD40L antibodies, or antigen-binding fragments thereof that serve to block CD40L-mediated CD40 signaling, and anti-CD40 therapeutic agents that modulate ADCC, for example, anti-CD40 antibodies and antigen-binding fragments thereof.

Anti-CD40 Antibodies.

Monoclonal antibodies to CD40 are known in the art. See, for example, the sections dedicated to B-cell antigen in McMichael, ed. (1987; 1989) *Leukocyte Typing III and IV* (Oxford University Press, New York); U.S. Pat. Nos. 5,674,492; 5,874,082; 5,677,165; 6,056,959; WO 00/63395; International Publication Nos. WO 02/28905 and WO 02/28904; Gordon et al. (1988) *J. Immunol.* 140:1425; Valle et al. (1989) *Eur. J. Immunol.* 19:1463; Clark et al. (1986) *PNAS* 83:4494; Paulie et al. (1989) *J. Immunol.* 142:590; Gordon et al. (1987) *Eur. J. Immunol.* 17:1535; Jabara et al. (1990) *J. Exp. Med.* 172:1861; Zhang et al. (1991) *J. Immunol.* 146:1836; Gascan et al. (1991) *J. Immunol.* 147:8; Banchereau et al. (1991) *Clin. Immunol. Spectrum* 3:8; and Banchereau et al. (1991) *Science* 251:70; all of which are herein incorporated by reference. Other anti-CD40 monoclonal antibodies include, but are not limited to, humanized anti-CD40 antibodies, such as SGN-40 (Tai et al. (2004) *Cancer Res.* 64:2846-52; U.S. Pat. No. 6,838,261), which is the humanized form of the murine anti-CD40 antibody SGN-14 (Francisco et al. (2000) *Cancer Res.* 60:3225-31), and the agonist and antagonist antibodies disclosed in U.S. Patent Application Publication No. 2004/0120948; herein incorporated by reference in their entirety.

In one embodiment, the ex vivo prognostic assays are used to examine suitability or efficacy of treatment with antagonist anti-CD40 antibodies. Antagonist anti-CD40 antibodies for use in the methods of the invention include monoclonal antibodies or antigen-binding fragments thereof that are capable of specifically binding to human CD40 antigen expressed on the surface of a human cell. In some embodiments, antagonist anti-CD40 antibodies for use in the methods of the present invention exhibit a strong single-site binding affinity for the CD40 cell-surface antigen. Such monoclonal antibodies exhibit a dissociation equilibrium constant ($K_D$) for CD40 of at least $10^{-5}$ M, at least $3 \times 10^{-5}$ M, preferably at least $10^{-6}$ M to $10^{-7}$ M, more preferably at least $10^{-8}$ M to about $10^{-12}$ M, measured using a standard assay such as Biacore™. Biacore analysis is known in the art and details are provided in the "BIAapplications handbook." Methods described in WO 01/27160 can be used to modulate the binding affinity.

Of particular interest are antagonist anti-CD40 antibodies that are free of significant agonist activity as defined herein above but exhibit antagonist activity when bound to CD40 antigen on human cells. In one embodiment of the invention, the antagonist anti-CD40 antibody is free of significant agonist activity in one B cell response. In another embodiment of the invention, the antagonist anti-CD40 antibody is free of significant agonist activity in assays of more than one B cell response (e.g., proliferation and differentiation, or proliferation, differentiation, and antibody production). Suitable monoclonal anti-CD40 antibodies have human constant regions; preferably they also have wholly or partially humanized framework regions; and most preferably are fully human antibodies or antigen-binding fragments thereof. Examples of such monoclonal antibodies are the antibodies designated herein as CHIR-5.9 and CHIR-12.12.

The monoclonal antibodies CHIR-5.9 and CHIR-12.12 represent antagonist anti-CD40 antibodies for use in the methods of the present invention. The CHIR-5.9 and CHIR-12.12 antibodies are fully human anti-CD40 monoclonal antibodies of the $IgG_1$ isotype produced from the hybridoma cell lines 131.2F8.5.9 (referred to herein as the cell line 5.9) and 153.8E2.D10.D6.12.12 (referred to herein as the cell line 12.12). These cell lines were created using splenocytes from immunized xenotypic mice containing the human $IgG_1$ heavy chain locus and the human κ chain locus (XenoMouse® technology; Abgenix; Fremont, Calif.). The spleen cells were fused with the mouse myeloma SP2/0 cells (Sierra BioSource). The resulting hybridomas were sub-cloned several times to create the stable monoclonal cell lines 5.9 and 12.12. Other antibodies of the invention may be prepared similarly using mice transgenic for human immunoglobulin loci or by other methods known in the art and/or described herein.

The nucleotide and amino acid sequences of the variable regions of the CHIR-12.12 antibody, and the amino acid sequences of the variable regions of the CHIR-5.9 antibody, are disclosed. More particularly, the amino acid sequences for the leader, variable, and constant regions for the light chain and heavy chain for mAb CHIR-12.12 are set forth in SEQ ID NO:2 (complete sequence for the light chain of mAb CHIR-12.12), SEQ ID NO:4 (complete sequence for the heavy chain for mAb CHIR-12.12), and SEQ ID NO:5 (complete sequence for a variant of the heavy chain for mAb CHIR-12.12 set forth in SEQ ID NO:4, where the variant comprises a serine substitution for the alanine residue at position 153 of SEQ ID NO:4). The nucleotide sequences encoding the light chain and heavy chain for mAb CHIR-12.12 are set forth in SEQ ID NO:1 (coding sequence for the light chain for mAb CHIR-12.12) and SEQ ID NO:3 (coding sequence for the heavy chain for mAb CHIR-12.12). The amino acid sequences for the leader, variable, and constant regions for the light chain and heavy chain of the CHIR-5.9 mAb are set forth in SEQ ID NO:6 (complete sequence for the light chain of mAb CHIR-5.9), SEQ ID NO:7 (complete sequence for the heavy chain of mAb CHIR-5.9), and SEQ ID NO:8 (complete sequence for a variant of the heavy chain of mAb CHIR-5.9 set forth in SEQ ID NO:7, where the variant comprises a serine substitution for the alanine residue at position 158 of SEQ ID NO:7). Further, hybridomas expressing CHIR-5.9 and CHIR-12.12 antibodies have been deposited with the ATCC with a patent deposit designation of PTA-5542 and PTA-5543, respectively.

In addition to antagonist activity, anti-CD40 antibodies for use in the methods of the present invention can have another mechanism of action against a tumor cell. For example, native CHIR-5.9 and CHIR-12.12 antibodies have ADCC activity. Alternatively, the variable regions of the CHIR-5.9 and CHIR-12.12 antibodies can be expressed on another antibody isotype that has ADCC activity. It is also possible to conjugate native forms, recombinant forms, or antigen-binding fragments of CHIR-5.9 or CHIR-12.12 to a cytotoxin, a therapeutic agent, or a radioactive metal ion or radioisotope, as noted herein below.

The CHIR-5.9 and CHIR-12.12 monoclonal antibodies bind soluble CD40 in ELISA-type assays, prevent the binding of CD40-ligand to cell-surface CD40, and displace the pre-bound CD40-ligand, as determined by flow cytometric assays. Antibodies CHIR-5.9 and CHIR-12.12 compete with each other for binding to CD40 but not with 15B8, the anti-CD40 monoclonal antibody described in U.S. Provisional Application Ser. No. 60/237,556, titled "Human Anti-CD40 Antibodies," filed Oct. 2, 2000, and PCT International Application No. PCT/US01/30857, also titled "Human Anti-CD40 Antibodies," filed Oct. 2, 2001, both of which are herein incorporated by reference in their entirety. When tested in vitro for effects on proliferation of B cells from normal human subjects, CHIR-5.9 and CHIR-12.12 act as antagonist anti-CD40 antibodies. Furthermore, CHIR-5.9 and CHIR-12.12 do not induce strong proliferation of human lymphocytes from normal subjects. These antibodies are able to kill CD40-expressing target cells by antibody dependent cellular cytotoxicity (ADCC). The binding affinity of CHIR-5.9 for human CD40 is $1.2 \times 10^{-8}$ M and the binding affinity of CHIR-12.12 is $5 \times 10^{-10}$ M, as determined by the Biacore™ assay.

Other antagonist anti-CD40 antibodies that share the binding characteristics of the monoclonal antibodies CHIR-5.9 and CHIR-12.12 described above include, but are not limited to the following: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen.

Those skilled in the art recognize that the antibodies and antigen-binding fragments of these antibodies described herein include antibodies and antigen-binding fragments thereof that are produced recombinantly using methods well known in the art and described herein below, and include, for example, monoclonal antibodies CHIR-5.9 and CHIR-12.12 that have been recombinantly produced.

Additional antagonist anti-CD40 antibodies include the monoclonal antibodies referred to as 5D12, 3A8 and 3C6, which are secreted by a hybridoma having ATCC accession numbers HB 11339, HB 12024 and HB 11340, respectively. See, for example, U.S. Pat. No. 6,315,998, herein incorporated by reference in its entirety.

Other antagonist anti-CD40 antibodies are known in the art. See, for example, the human anti-CD40 antibody produced by the hybridoma designated F4-465 disclosed in U.S. Patent Application Publication Nos. 20020142358 and 20030059427; herein incorporated by reference in their entirety. F4-465 was obtained from the HAC mouse (Kuroiwa et al. (2000) *Nature Biotech.* 10:1086 (2000)) and therefore expresses the human lambda light chain.

Antagonist Anti-CD40L Antibodies.

Antibodies that bind to CD40L and thereby interfere with CD40/CD40L interaction or CD40L-mediated CD40 signaling are known in the art. Examples include, but are not limited to, those disclosed in International Patent Publication WO 95/06666, the content of which is herein by reference in its entirety. Specific examples include, but are not limited to antagonist anti-CD40L antibodies designated 89-76 and 24-31, which are produced by the 89-76 and 24-31 hybridomas, respectively, deposited with the American Type Culture Collection (ATCC), 10801 University Blvd., Manassas, Va. 20110-2209, and assigned ATCC Accession Number HB11713 and HB11712, respectively.

Production of Antibodies

The antibodies for use in the methods of the present invention, for example, the antagonist anti-CD40 antibodies disclosed herein and any antibody that specifically binds to a biomarker or other clinically useful prognostic marker of interest, can be produced using any antibody production method known to those of skill in the art. Thus, polyclonal sera may be prepared by conventional methods. In general, a solution containing the antigen of interest, for example, the CD40 antigen or CD40L antigen, is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies.

Polyclonal sera can be prepared in a transgenic animal, preferably a mouse bearing human immunoglobulin loci. In a preferred embodiment, Sf9 cells expressing the protein of interest, for example, CD40 or CD40L, are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Production of the Sf 9 (*Spodoptera frugiperda*) cells is disclosed in U.S. Pat. No. 6,004,552, incorporated herein by reference. In the case of CD40, briefly, sequences encoding human CD40 were recombined into a baculovirus using transfer vectors. The plasmids were co-transfected with wild-type baculovirus DNA into Sf 9 cells. Recombinant baculovirus-infected Sf 9 cells were identified and clonally purified.

Preferably the antibody is monoclonal in nature. By "monoclonal antibody" is intended an antibody obtained from a population of substantially homogeneous antibodies, i.e., the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site; for example, in the case of anti-CD40 antibodies or anti-CD40L antibodies, the CD40 cell surface antigen or CD40L cell surface antigen, respectively. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222: 581-597; and U.S. Pat. No. 5,514,548.

By "epitope" is intended the part of an antigenic molecule to which an antibody is produced and to which the antibody will bind. Epitopes can comprise linear amino acid residues (i.e., residues within the epitope are arranged sequentially one after another in a linear fashion), nonlinear amino acid residues (referred to herein as "nonlinear epitopes"; these epitopes are not arranged sequentially), or both linear and nonlinear amino acid residues.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

Where antibodies for use in the methods of the invention, for example, antagonist anti-CD40 antibodies or antagonist anti-CD40L antibodies, are to be prepared using recombinant DNA methods, the DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al. (1993) *Curr. Opinion in Immunol.* 5:256 and Phickthun (1992) *Immunol. Revs.* 130:151. Alternatively, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

In some embodiments, the antagonist anti-CD40 antibody, for example, the CHIR-12.12 or CHIR-5.9 antibody, or antigen-binding fragment thereof is produced in CHO cells using the GS gene expression system (Lonza Biologics, Portsmouth, N.H.), which uses glutamine synthetase as a marker. See, also U.S. Pat. Nos. 5,122,464; 5,591,639; 5,658,759; 5,770,359; 5,827,739; 5,879,936; 5,891,693; and 5,981,216; the contents of which are herein incorporated by reference in their entirety.

Additionally, antibodies for use in the methods of the invention can be chimeric antibodies that have the desired binding characteristics. Thus, for example, chimeric anti-CD40 antibodies for use in the methods of the invention could have the binding characteristics of the CHIR-5.9 and CHIR-12.12 monoclonal antibodies described herein. By "chimeric" antibodies is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the antigen of interest, for example, CD40 or CD40L antigen. The non-human source can be any vertebrate source that can be used to generate antibodies to a human antigen or material comprising a human CD40 antigen. Such non-human sources include, but are not limited to, rodents (e.g., rabbit, rat, mouse, etc.; see, for example, U.S. Pat. No. 4,816,567, herein incorporated by reference) and non-human primates (e.g., Old World Monkey, Ape, etc.; see, for example, U.S. Pat. Nos. 5,750,105 and 5,756,096; herein incorporated by reference). As used herein, the phrase "immunologically active" when used in reference, for example, to chimeric anti-CD40 antibodies or chimeric anti-CD40L antibodies, means a chimeric antibody that binds human CD40 or human CD40L, respectively.

By "humanized" is intended forms of antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. The phrase "complementarity determining region" refers to amino acid sequences which together define the binding affinity and specificity of the natural Fv region of a native immunoglobulin binding site. See, e.g., Chothia et al (1987) *J. Mol. Biol.* 196:901-917; Kabat et al (1991) U.S. Dept. of Health and Human Services, NIH Publication No. 91-3242). The phrase "constant region" refers to the portion of the antibody molecule that confers effector functions. In previous work directed towards producing non-immunogenic antibodies for use in therapy of human disease, mouse constant regions were substituted by human constant regions. The constant regions of the subject humanized antibodies were derived from human immunoglobulins. However, these humanized antibodies still elicited an unwanted and potentially dangerous immune response in humans and there was a loss of affinity. Humanized antibodies, for example, humanized anti-CD40 antibodies, for use in the methods of the present invention have binding characteristics similar to those exhibited by the parent antibody of interest, for example, the CHIR-5.9 and CHIR-12.12 monoclonal antibodies described herein.

Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) *Nature* 331:522-525; Riechmann et al. (1988) *Nature* 332:323-329; and Presta (1992) *Curr. Op. Struct. Biol.* 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

The present invention can also be practiced using xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598, herein incorporated by reference.

In some embodiments, fully human antibodies to CD40, for example, are obtained by immunizing transgenic mice. One such mouse is obtained using XenoMouse® technology (Abgenix; Fremont, Calif.), and is disclosed in U.S. Pat. Nos. 6,075,181, 6,091,001, and 6,114,598, all of which are incorporated herein by reference. To produce the antibodies disclosed herein, mice transgenic for the human Ig $G_1$ heavy chain locus and the human κ light chain locus were immunized with Sf 9 cells expressing human CD40. Mice can also be transgenic for other isotypes. Fully human anti-CD40 antibodies useful in the methods of the present invention are characterized by binding properties similar to those exhibited by the CHIR-5.9 and CHIR-12.12 monoclonal antibodies disclosed herein.

Fragments of a particular antibody of interest, for example, an anti-CD40 antibody or anti-CD40L antibody, are suitable for use in the methods of the invention so long as they retain the desired affinity of the full-length antibody. Thus, for example, a fragment of an anti-CD40 antibody will retain the ability to bind to the CD40 B cell surface antigen. Such fragments are characterized by properties similar to the corresponding full-length antibody. Thus, for example, a fragment of a full-length antagonist anti-CD40 antibody will specifically bind a human CD40 antigen expressed on the surface of a human cell, and is free of significant agonist activity but exhibits antagonist activity when bound to a CD40 antigen on a human CD40-expressing cell. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By F(ab')$_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal*

*Antibodies*, Vol. 113, ed. Rosenburg and Moore (Springer-Verlag, New York), pp. 269-315. Antigen-binding fragments of the antagonist anti-CD40 antibodies disclosed herein can also be conjugated to a cytotoxin to effect killing of the target cells, as described herein below.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

Antagonist anti-CD40 antibodies for use in the methods of the present invention include the CHIR-5.9 and CHIR-12.12 monoclonal antibodies disclosed herein as well as antibodies differing from this antibody but retaining the CDRs; and antibodies with one or more amino acid addition(s), deletion(s), or substitution(s), wherein the antagonist activity is measured by inhibition of B-cell proliferation and/or differentiation. The invention also encompasses de-immunized antibodies, particularly de-immunized antagonist anti-CD40 antibodies, which can be produced as described in, for example, International Publication Nos. WO 98/52976 and WO 0034317; herein incorporated by reference. In this manner, residues within the antagonist anti-CD40 antibodies of the invention are modified so as to render the antibodies non- or less immunogenic to humans while retaining their antagonist activity toward human CD40-expressing cells, wherein such activity is measured by assays noted elsewhere herein. Also included within the scope of the present invention are fusion proteins comprising an antibody of interest, for example, an antagonist anti-CD40 antibody or an antagonist anti-CD40L antibody, or a fragment thereof, which fusion proteins can be synthesized or expressed from corresponding polynucleotide vectors, as is known in the art. Such fusion proteins are described with reference to conjugation of antibodies as noted elsewhere herein.

Any known antibody having the binding specificity of interest can have sequence variations produced using methods described in, for example, Patent Publication Nos. EP 0 983 303 A1, WO 00/34317, and WO 98/52976, incorporated herein by reference. For example, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Any such conservative or non-conservative substitutions can be made using art-recognized methods, such as those noted elsewhere herein, and the resulting antibodies can also be used in the methods of the present invention. The variant antibodies can be routinely tested for the particular activity, for example, antagonist activity, affinity, and specificity using methods described herein.

Where the anti-CD40 therapeutic agent is an antagonist anti-CD40 antibody, the antagonist anti-CD40 antibody produced by any of the methods described above, or any other method not disclosed herein, can be used in a manner similar to the CHIR-12.12 or CHIR-5.9 antibody where it possesses at least one of the following biological activities: in vitro and/or in vivo: inhibition of immunoglobulin secretion by normal human peripheral B cells stimulated by T cells; inhibition of survival and/or proliferation of normal human peripheral B cells stimulated by CD40L-expressing cells or soluble CD40 ligand (sCD40L); inhibition of survival and/or proliferation of normal human peripheral B cells stimulated by Jurkat T cells; inhibition of "survival" anti-apoptotic intracellular signals in any cell stimulated by sCD40L or solid-phase CD40L; and, inhibition of CD40 signal transduction in any cell upon ligation with sCD40L or solid-phase CD40L, deletion, anergy and/or tolerance induction of CD40-bearing target cells or cells bearing cognate ligands to CD40 including, but not limited to, T cells and B cells, induction of expansion or activation of CD4$^+$CD25$^+$ regulatory T cells (see for example, donor alloantigen-specific tissue rejection via CD40-CD40L interference, van Maurik et al. (2002) *J. Immunol.* 169:5401-5404), cytotoxicity via any mechanism (including, but not limited to, antibody-dependent cell-mediated cytotoxicity (ADCC), complement-dependent cytotoxicity (CDC), down-regulation of proliferation, and/or apoptosis in target cells), modulation of target cell cytokine secretion and/or cell surface molecule expression, and combinations thereof. Assays for such biological activities can be performed as described herein and in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337 , 60/525,579, and 60/565,710, respectively, and International Patent Application No. PCT/US2004/037152, also entitled "Antagonist Anti-CD40 Monoclonal Antibodies and Methods for Their Use," filed Nov. 4, 2004; the contents of each of which are herein incorporated by reference in their entirety. See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

A representative assay to detect antagonist anti-CD40 antibodies specific to the CD40-antigen epitopes identified herein is a "competitive binding assay." Competitive binding assays are serological assays in which unknowns are detected and quantitated by their ability to inhibit the binding of a labeled known ligand to its specific antibody. This is also referred to as a competitive inhibition assay. In a representative competitive binding assay, labeled CD40 polypeptide is precipitated by candidate antibodies in a sample, for example, in combination with monoclonal antibodies raised against one or more epitopes of the monoclonal antibodies of the invention. Anti-CD40 antibodies that specifically react with an epitope of interest can be identified by screening a series of antibodies prepared against a CD40 protein or fragment of the protein comprising the particular epitope of the CD40 protein of interest. For example, for human CD40, epitopes of interest include epitopes comprising linear and/or nonlinear amino acid residues of the short isoform of human CD40 (see GenBank Accession No. NP_690593) set forth in SEQ ID NO:10, encoded by the sequence set forth SEQ ID NO:9; see also GenBank Accession No. NM_152854), or of the long isoform of human CD40 (see GenBank Accession Nos. CAA43045 and NP_001241, set forth in SEQ ID NO:12, encoded by the sequence set forth in SEQ ID NO:11; see GenBank Accession Nos. X60592 and NM_001250). Alternatively, competitive binding assays with previously identified suitable antagonist anti-CD40 antibodies could be used to select monoclonal antibodies comparable to the previously identified antibodies.

Antibodies employed in such immunoassays may be labeled or unlabeled. Unlabeled antibodies may be employed in agglutination; labeled antibodies may be employed in a wide variety of assays, employing a wide variety of labels. Detection of the formation of an antibody-antigen complex between an anti-CD40 antibody and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}I$, $^{131}I$, $^{35}S$, or $^{3}H$. Such labeled reagents may be used in a variety of well-known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Any of the previously described antibodies, for example, antagonist anti-CD40 antibodies or antibody fragments thereof, may be conjugated prior to use in the methods of the present invention. Methods for producing conjugated antibodies are known in the art. Thus, the antibody may be labeled using an indirect labeling or indirect labeling approach. By "indirect labeling" or "indirect labeling approach" is intended that a chelating agent is covalently attached to an antibody and at least one radionuclide is inserted into the chelating agent. See, for example, the chelating agents and radionuclides described in Srivagtava and Mease (1991) *Nucl. Med. Bio.* 18:589-603, herein incorporated by reference. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefore. Other specific binding partners include biotin and avidin or streptavidin, Ig G and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a mAb. Further, one may combine various labels for desired effect. For example, mAbs and avidin also require labels in the practice of this invention: thus, one might label a mAb with biotin, and detect its presence with avidin labeled with $^{125}I$, or with an anti-biotin mAb labeled with HRP. Other permutations and possibilities will be readily apparent to those of ordinary skill in the art, and are considered as equivalents within the scope of the instant invention.

Alternatively, an antibody of interest, for example, an anti-CD40 antibody, may be labeled using "direct labeling" or a "direct labeling approach," where a radionuclide is covalently attached directly to an antibody (typically via an amino acid residue). Preferred radionuclides are provided in Srivagtava and Mease (1991) supra. The indirect labeling approach is particularly preferred. See also, for example, International Publication Nos. WO 00/52031 and WO 00/52473, where a linker is used to attach a radioactive label to antibodies; and the labeled forms of anti-CD40 antibodies described in U.S. Pat. No. 6,015,542; herein incorporated by reference.

Variants of Antibodies

The methods of the present invention can be carried out using variants of an antibody known in the art. Such variants will retain the desired binding properties of the parent antibody. Thus, for example, where the anti-CD40 therapeutic agent to be tested is an antagonist anti-CD40 antibody, the variant antibody will retain the binding properties of the parent antagonist anti-CD40 antibody, for example, the CHIR-12.12 or CHIR-5.9 antibody. Methods for making antibody variants are generally available in the art. Though the following discussion refers to variants of an antagonist anti-CD40 antibody, the methods are generally applicable to any antibody of interest, for example, an antibody that specifically binds to a biomarker or clinically useful prognostic marker disclosed herein.

For example, amino acid sequence variants of an antagonist anti-CD40 antibody, for example, the CHIR-5.9 or CHIR-12.12 monoclonal antibody described herein, can be prepared by mutations in the cloned DNA sequence encoding the antibody of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of an antibody of interest, for example, an antagonist anti-CD40 antibody polypeptide of interest, modifications are made such that variants continue to possess the desired activity, i.e., similar binding affinity and, in the case of antagonist anti-CD40 antibodies, are capable of specifically binding to a human CD40 antigen expressed on the surface of a human cell, and being free of significant agonist activity but exhibiting antagonist activity when bound to a CD40 antigen on a human CD40-expressing cell. Obviously, any mutations made in the DNA encoding the variant polypeptide must not place the sequence out of reading frame and preferably will not create complementary regions that could produce secondary mRNA structure. See EP Patent Application Publication No. 75,444.

In addition, the constant region of an antibody, for example, an antagonist anti-CD40 antibody, can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Preferably, variants of a reference antibody, for example, an antagonist anti-CD40 antibody, have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody, for example, an antagonist anti-CD40 antibody molecule, for example, the CHIR-5.9 or CHIR-12.12 monoclonal antibody described herein, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antibody, for example, an antagonist anti-CD40 antibody, by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

Methods of Therapy

The ex vivo prognostic assays described herein can also be used in methods of therapy for a subject in need of treatment for an inflammatory disease and/or autoimmune disease that is associated with CD40-expressing cells. Thus, in some embodiments, the ex vivo prognostic assay is carried out on a candidate subject, and, where results of the assay predict a favorable response with treatment with the anti-CD40 therapeutic agent, the subject is then treated with that anti-CD40 therapeutic agent. As noted herein above, the information obtained from the ex vivo prognostic assay can be used alone to render a decision with regard to benefit of treatment with the anti-CD40 therapeutic agent. Alternatively, the ex vivo prognostic assay can be used in combination with prognostic assays that screen for level of expression, or presence or absence of expression, of one or more of the CD40-related factors identified herein; prognostic assays that screen for level of expression, or presence or absence of expression, of one or more clinically useful prognostic markers for the particular inflammatory or autoimmune disease, for example, a clinically useful prognostic marker such as identified herein, or both.

In this manner, a subject identified using the ex vivo prognostic assays of the present invention, alone or in combination with other prognostic assays described herein, can be further treated with one or more therapeutically effective doses of the anti-CD40 therapeutic agent that has been identified in the screening process as being beneficial for treatment of the disease in the candidate subject. "Treatment" is herein defined as the application or administration of an anti-CD40 therapeutic agent to a subject, or application or administration of an anti-CD40 therapeutic agent to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to cure, heal, alleviate, relieve, alter, remedy, ameliorate, improve, or affect the autoimmune disease and/or inflammatory disease, any associated symptoms of the autoimmune disease and/or inflammatory disease, or the predisposition toward the development of the autoimmune disease and/or inflammatory disease. By "treatment" is also intended the application or administration of a pharmaceutical composition comprising an anti-CD40 therapeutic agent to a subject, or application or administration of a pharmaceutical composition comprising an antagonist anti-CD40 therapeutic agent to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to cure, heal, alleviate, relieve, alter, remedy, ameliorate, improve, or affect the autoimmune disease and/or inflammatory disease, any associated symptoms of the autoimmune disease and/or inflammatory disease, or the predisposition toward the development of the autoimmune disease and/or inflammatory disease.

By "anti-inflammatory activity" is intended a reduction or prevention of inflammation. Therapy with at least one anti-CD40 therapeutic agent as defined elsewhere herein causes a physiological response that is beneficial with respect to treatment of an autoimmune disease and/or inflammatory disease, where the disease involves cells expressing the CD40 antigen. It is recognized that the methods of the invention may be useful in preventing phenotypic change in cells such as proliferation, activation, and the like.

By "therapeutically effective dose or amount" or "effective amount" is intended an amount of the anti-CD40 therapeutic agent that, when administered brings about a positive therapeutic response with respect to treatment of a patient with an autoimmune disease and/or inflammatory disease. In some embodiments of the invention, the anti-CD40 therapeutic agent is an antagonist anti-CD40 antibody, an antagonist anti-CD40L antibody, or antigen-binding fragment thereof, and the therapeutically effective dose of the anti-CD40 antibody, anti-CD40L antibody, or fragment thereof, is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the anti-CD40 therapeutic agent, for example, an antagonist anti-CD40 antibody, antagonist anti-CD40L antibody, or antigen-binding fragment thereof.

In some embodiments, the ex vivo prognostic assays of the invention can be used to ascertain the physiological basis for responsiveness, or lack of responsiveness, to treatment with a particular anti-CD40 therapeutic agent. Thus, where an inflammatory or autoimmune disease in a subject is initially responsive to therapy with an anti-CD40 therapeutic agent, and CD40-expressing cells of the disease develop resistance to this line of therapy, the ex vivo prognostic assays can be used to define which CD40L-CD40 interaction(s) contribute to the resistant nature of these CD40-expressing cells.

The biomarkers of CD40L-mediated CD40 signaling, i.e., biomarkers of apoptosis, cell proliferation and survival, cytokine markers of CD40L-mediated CD40 signaling, and CD40-related factors described herein can also be used, alone or in any combination thereof, to monitor efficacy of treatment with an anti-CD40 therapeutic agent. In this manner, a subject who is undergoing treatment with an anti-CD40 therapeutic agent, who may or may not have been previously screened for suitability of treatment with the anti-CD40 therapeutic agent using a prognostic assay described above, is monitored for in vivo changes in the expression of at least one biomarker of cellular apoptosis, cell proliferation and survival, and/or one or more CD40 signaling pathways, wherein cytokine production is optionally monitored (depending upon the mode of action of the anti-CD40 therapeutic agent) following treatment with the anti-CD40 therapeutic agent. Alternatively, or additionally, the subject can be monitored for in vivo changes in the expression level of one or more CD40-related factors selected from the group consisting of cell-surface CD40 antigen on cells, cell-surface CD40L on cells, circulating level of sCD40, and circulating level of sCD40L following treatment with the anti-CD40 therapeutic agent.

In this manner, a first biological sample is obtained from the subject prior to treatment with the anti-CD40 therapeutic agent of interest and assayed for the expression level of one or more of these biomarkers and/or CD40-related factors to obtain a baseline level of expression for each factor assayed. This first biological sample is referred to as the "baseline biological sample." One or more subsequent biological samples, of the same tissue type or bodily fluid, is obtained from the subject and assayed for the same biomarker(s) and/or CD40-related factor(s), where the subsequent biological sample is obtained following the administration of at least one dose of the anti-CD40 therapeutic agent of interest. Monitoring can occur at a single point in time, or at multiple points in time to ascertain efficacy of any given treatment protocol wherein the anti-CD40 therapeutic agent is administered to the subject. Depending upon the biomarker being assayed, a decrease or increase in the level of the biomarker between any two time points can be indicative of efficacy of the anti-CD40 therapeutic agent in treatment of the inflammatory or autoimmune disease. Where monitoring reveals a decrease in the expression level of one or more of the CD40-related factors, such a result can be indicative of efficacy of the anti-CD40 therapeutic agent in treatment of the inflammatory or autoimmune disease.

Thus, in some embodiments, efficacy of treatment of a subject with an anti-CD40 therapeutic agent that blocks or interferes with CD40L-mediated CD40 signaling is monitored by obtaining a baseline biological sample from the subject and detecting the level of expression of one or more biomarkers of cell survival and/or a CD40L-mediated CD40 signaling pathway described herein above; administering at least one dose of the therapeutic agent, for example, an antagonist anti-CD40 antibody such as CHIR-12.12 or CHIR-5.9 or antigen-binding fragment thereof, to the subject; obtaining a subsequent biological sample from the subject, for example, within about 30 minutes to about 24 hours, including about 30 minutes to about 12 hours, about 30 minutes to about 6 hours, about 30 minutes to about 4 hours, and about 1 hour to about 4 hours; and detecting the level of expression of the biomarker(s) of cell survival and/or CD40L-mediated CD40 signaling pathway in the subsequent biological sample; wherein a reduction in the level of expression in the subsequent biological sample compared to the level of expression in the baseline biological sample is indicative of efficacy of treatment with the anti-CD40 therapeutic agent. Detection can be accomplished using any method known in the art including those methods disclosed elsewhere herein. In some embodiments, the level of expression is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the baseline biological sample. A percent change from baseline of at least 25% (i.e., at least a 25% reduction relative to the baseline biological sample) is indicative of efficacy of the anti-CD40 therapeutic agent, with intermediate responsiveness indicated by a percent change of at least 30% or at least 40%. Preferably, the percent change from baseline is at least 50% (i.e., at least a 50% reduction relative to the baseline biological sample) or higher.

In some embodiments, efficacy of treatment of a subject with an anti-CD40 therapeutic agent that blocks or interferes with CD40L-mediated CD40 signaling is monitored by obtaining a baseline biological sample from the subject and detecting the level of expression of cytokine markers of CD40L-mediated CD40 signaling described herein above; administering at least one dose of the therapeutic agent, for example, an antagonist anti-CD40 antibody such as CHIR-12.12 or CHIR-5.9 or antigen-binding fragment thereof, to the subject; obtaining a subsequent biological sample from the subject, for example, within about 24 hours to about 3 weeks, including about 48 hours, about 72 hours, about 1 week, or about 2 weeks, after dosing; and detecting the level of expression of the biomarker(s) of cell survival and/or CD40L-mediated CD40 signaling pathway in the subsequent biological sample; wherein a reduction in the level of expression in the subsequent biological sample compared to the level of expression in the baseline biological sample is indicative of efficacy of treatment with the anti-CD40 therapeutic agent. Detection can be accomplished using any method known in the art including those methods disclosed elsewhere herein. Further, cytokines that are not affected by CD40L-mediated CD40 signaling (for example, IL-1b, GM-CSF, and IL-12; see the Experimental section herein below) can be used as a control to normalize data. In some embodiments, the level of expression is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the baseline biological sample. A percent change from baseline of at least 20% (i.e., at least a 20% reduction relative to the baseline biological sample) or higher is indicative of efficacy of the anti-CD40 therapeutic agent. In some embodiments, baseline biological samples comprising serum or serum extract are frozen for subsequent analysis of cytokine markers.

In other embodiments, efficacy of treatment of a subject with an anti-CD40 therapeutic agent that blocks or interferes with CD40L-mediated CD40 signaling, or which has ADCC as its mode of action, is monitored by obtaining a baseline biological sample from the subject and detecting the level of expression of one or more biomarkers of apoptosis described herein above; administering at least one dose of the therapeutic agent, for example, an antagonist anti-CD40 antibody such as CHIR-12.12 or CHIR-5.9 or antigen-binding fragment thereof, to the subject; obtaining a subsequent biological sample from the subject, for example, within about 8 hours, 12 hours, 24 hours, 36 hours, 48 hours, or 72 hours after dosing, and optionally again about 1 week, about 2 weeks, or about 3 weeks after dosing; and detecting the level of expression of the biomarker(s) of apoptosis in the subsequent biological sample(s); wherein an increase in the level of expression in the subsequent biological sample(s) compared to the level of expression in the baseline biological sample is indicative of efficacy of treatment with the anti-CD40 therapeutic agent. Detection can be accomplished using any method known in the art including those methods disclosed elsewhere herein. In some embodiments, the level of expression is increased by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or higher relative to that detected in the baseline biological sample. A percent change from baseline of at least 20% (i.e., at least a 20% increase relative to the baseline biological sample) or higher is indicative of efficacy of the anti-therapeutic agent.

In yet other embodiments, efficacy of treatment of a subject with an anti-CD40 therapeutic agent that blocks or interferes with CD40L-mediated CD40 signaling, modulates ADCC, or both, is monitored by obtaining a baseline biological sample from the subject and detecting the level of expression of one or more CD40-related factors described herein above (i.e., cell-surface CD40 and/or CD40L on cells, and/or circulating levels of sCD40 and/or sCD40L); administering at least one dose of the therapeutic agent, for example, an antagonist anti-CD40 antibody such as CHIR-12.12 or CHIR-5.9 or antigen-binding fragment thereof, to the subject; obtaining a subsequent biological sample from the subject, for example, within about 1 day (i.e., 24 hours), 2 days, 3 days, 4 days, or 1 week; and detecting the level of expression of the CD40-related factor; wherein a reduction in the level of expression in the subsequent biological sample compared to the level of expression in the baseline biological sample is indicative of efficacy of treatment with the anti-CD40 therapeutic agent. In some embodiments, the level of expression is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the baseline biological sample.

It is recognized that any one or a combination of these assays can be carried out to monitor efficacy of treatment of a subject with an inflammatory or autoimmune disease with an anti-CD40 therapeutic agent of interest, depending upon its mode of action. Where efficacy is demonstrated, subsequent doses of the anti-CD40 therapeutic agent can be administered according to the recommended dosing regimen, for example, daily, every other day, thrice weekly, twice weekly, once a week, bi-weekly, monthly, and the like. Alternatively, the in vivo level of expression of the marker(s) of interest (i.e., biomarker(s) of cell proliferation and survival, biomarker(s) of CD40L-mediated CD40 signaling pathways, cytokine marker(s), CD40-related factor(s), and any combination thereof can serve as a guide to dosing frequency, and can also serve as an indication as to therapeutically effective dose to be administered. In this manner, where subsequent biological samples continue to show an acceptable reduction or increase in the expression level of the respective marker(s) of interest, further dosing with the anti-CD40 therapeutic agent can be delayed until such time as the expression level of the respective marker(s) approaches that observed in the baseline biological sample. As some biomarkers may fluctuate independently of the effects of the therapeutic agent, which also will vary in half-life and residence times, preferably at least two consecutive measurements (for example, within a 24-48 hour period) are taken into consideration when using the expression level of the marker (i.e., biomarker of apoptosis, cell survival, CD40-signaling pathway, cytokine marker, and/or CD40-related factor) as a guide to dosing frequency.

Where results of these assays continue to show desired downregulation of CD40L-mediated CD40 signaling with respect to a decline in expression of one or more of the biomarkers of cell survival, one or more of the biomarkers of a CD40 signaling pathway, and/or one or more of the CD40-related factors, and an increase in expression of one or more of the markers of cell apoptosis, further treatment with the anti-CD40 therapeutic agent is warranted. Biological samples can be collected at various time intervals over the course of a treatment period as noted herein above to allow for monitoring of treatment efficacy over time, and to determine whether treatment should be continued or withdrawn.

The following examples are offered by way of illustration and not by way of limitation.

EXPERIMENTAL

Introduction

The antagonist anti-CD40 antibodies used in the examples below are CHIR-5.9 and CHIR-12.12. The CHIR-5.9 and CHIR-12.12 anti-CD40 antibodies are human IgG, subtype anti-human CD40 monoclonal antibodies (mAbs) generated by immunization of transgenic mice bearing the human IgG$_1$ heavy chain locus and the human κ light chain locus (XenoMouse® technology (Abgenix; Fremont, Calif.)). SF9 insect cells expressing CD40 extracellular domain were used as immunogen.

Briefly, splenocytes from immunized mice were fused with SP 2/0 or P 3×63Ag8.653 murine myeloma cells at a ratio of 10:1 using 50% polyethylene glycol as previously described by de Boer et al. (1988) *J. Immunol. Meth.* 113:143. The fused cells were resuspended in complete IMDM medium supplemented with hypoxanthine (0.1 mM), aminopterin (0.01 mM), thymidine (0.016 mM), and 0.5 ng/ml hIL-6 (Genzyme, Cambridge, Mass.). The fused cells were then distributed between the wells of 96-well tissue culture plates, so that each well contained 1 growing hybridoma on average.

After 10-14 days, the supernatants of the hybridoma populations were screened for specific antibody production. For the screening of specific antibody production by the hybridoma clones, the supernatants from each well were pooled and tested for anti-CD40 activity specificity by ELISA first. The positives were then used for fluorescent cell staining of EBV-transformed B cells using a standard FACS assay. Positive hybridoma cells were cloned twice by limiting dilution in IMDM/FBS containing 0.5 ng/ml hIL-6.

A total of 31 mice spleens were fused with the mouse myeloma SP2/0 cells to generate 895 antibodies that recognize recombinant CD40 in ELISA. On average approximately 10% of hybridomas produced using Abgenix XenoMouse® technology (Abgenix; Fremont, Calif.) may contain mouse lambda light chain instead of human kappa chain. The antibodies containing mouse light lambda chain were selected out. A subset of 260 antibodies that also showed binding to cell-surface CD40 were selected for further analysis. Stable hybridomas selected during a series of subcloning procedures were used for further characterization in binding and functional assays. For further details of the selection process, see copending provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and International Patent Application No. PCT/US2004/037152, also entitled "Antagonist Anti-CD40 Monoclonal Antibodies and Methods for Their Use," filed Nov. 4, 2004, and published as WO 2005/044854; the contents of each of which are herein incorporated by reference in their entirety.

Clones from 7 other hybridomas were identified as having antagonistic activity. Based on their relative antagonistic potency and ADCC activities, two hybridoma clones were selected for further evaluation (Table 1 below). They are named 131.2F8.5.9 (5.9) and 153.8E2.D10.D6.12.12 (12.12).

ligand binding. Both mAbs can compete off CD40-ligand pre-bound to cell surface CD40. The binding affinity of CHIR-5.9 to human CD40 is $1.2 \times 10^{-8}$ M and the binding affinity of CHIR-12.12 to human CD40 is $5 \times 10^{-10}$ M.

The CHIR-12.12 and CHIR-5.9 monoclonal antibodies are strong antagonists and inhibit in vitro CD40 ligand-mediated proliferation of normal B cells, as well as inhibiting in vitro CD40 ligand-mediated proliferation of cancer cells from NHL and CLL patients. The CHIR-12.12 monoclonal antibody directly inhibits survival and signaling pathways mediated by CD40 ligand (CD40L) in normal human B-lymphocytes. In vitro, both antibodies kill primary cancer cells from NHL patients by ADCC. Dose-dependent anti-tumor activity was seen in a xenograft human lymphoma model. For a more detailed description of these results, and the assays used to obtain them, see provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and International Patent Application No. PCT/US2004/037152, also entitled "Antagonist Anti-CD40 Monoclonal Antibodies and Meth-

TABLE 1

Summary of initial set of data with anti-CD40 IgG1 antibodies CHIR-5.9 and CHIR-12.12.

| Mother Hybridoma | Hybridoma clones | Cell surface binding | Antagonist | ADCC | CDC | CMCC# | V-region DNA sequence |
|---|---|---|---|---|---|---|---|
| 131.2F5 | 131.2F5.8.5.9 | +++ | +++ | ++ | − | 12047 | Yes |
| 153.8E2 | 153.8E2D10D6.12.12 | +++ | +++ | ++++ | − | 12056 | Yes |

Mouse hybridoma line 131.2F8.5.9 (CMCC#12047) and hybridoma line 153.8E2.D10.D6.12.12 (CMCC#12056) have been deposited with the American Type Culture Collection (ATCC; 10801 University Blvd., Manassas, Va. 20110-2209 (USA)) on Sep. 17, 2003, under Patent Deposit Number PTA-5542 and PTA-5543, respectively.

The cDNAs encoding the variable regions of the candidate antibodies were amplified by PCR, cloned, and sequenced. The amino acid sequences for the light chain and heavy chain of the CHIR-12.12 antibody are set forth in SEQ ID NO:2 (light chain for mAb CHIR-12.12) and SEQ ID NO:4 (heavy chain for mAb CHIR-12.12). A variant of the heavy chain for mAb CHIR-12.12 is shown in SEQ ID NO:5, which differs from SEQ ID NO:4 in having a serine residue substituted for the alanine residue at position 153 of SEQ ID NO:4. The nucleotide sequences encoding the light chain and heavy chain of the CHIR-12.12 antibody are set forth in SEQ ID NO:1 (coding sequence for light chain for mAb CHIR-12.12) and SEQ ID NO:3 (coding sequence for heavy chain for mAb CHIR-12.12). The amino acid sequences for the light chain and heavy chain of the CHIR-5.9 antibody are set forth in SEQ ID NO:6 (light chain for mAb CHIR-5.9) and SEQ ID NO:7 (heavy chain for mAb CHIR-5.9). A variant of the heavy chain for mAb CHIR-5.9 is shown in SEQ ID NO:8, which differs from SEQ ID NO:7 in having a serine residue substituted for the alanine residue at position 158 of SEQ ID NO:7.

As expected for antibodies derived from independent hybridomas, there is substantial variation in the nucleotide sequences in the complementarity determining regions (CDRs). The diversity in the CDR3 region of $V_H$ is believed to most significantly determine antibody specificity.

As shown by FACS analysis, CHIR-5.9 and CHIR-12.12 bind specifically to human CD40 and can prevent CD40- ods for Their Use," filed Nov. 4, 2004; the contents of each of which are herein incorporated by reference in their entirety.

Example 1

CHIR-12.12 Blocks CD40L-Mediated Cell Signaling

Soluble CD40 ligand (CD40L) activates B cells and induces various aspects of functional responses, including enhancement of survival and proliferation, and activation of NF-κB, ERK/MAPK, PI3K/AKT, and p38 signaling pathways. In addition, CD40L-mediated CD40 stimulation provides survival signals by reduction of cleaved PARP and induction of the anti-apoptotic proteins, XIAP and Mcl-1, in normal B cells. CD40L-mediated CD40 stimulation also recruits TRAF2 and TRAF3 to bind CD40 cytoplasmic domain.

The following studies demonstrate that CHIR-12.12 directly inhibited all of these stimulation effects on normal human B cells. For example, CHIR-12.12 treatment resulted in increased cleavage of Caspase-9, Caspase-3, and PARP as well as reduction of XIAP and Mcl-1 in a time- and dose-dependent manner, restoring B cell apoptosis. Treatment with CHIR-12.12 also inhibited phosphorylation of IκB kinase (IKK) α and β (NF-κB pathway), ERK, AKT, and p38 in response to CD40L-mediated CD40 stimulation. Further, it was found that CHIR-12.12 did not trigger these apoptotic effects without initial CD40L-mediated CD40 stimulation.

CHIR-12.12 Inhibited Survival Mediated by CD40 Ligand by Inducing Cleavage of PARP.

In these experiments, $0.6 \times 10^6$ normal human B cells from healthy donors (percent purity between 85-95%) were stimulated with 1 μg/ml sCD40L (Alexis Corporation, Bingham, Nottinghamshire, UK). CHIR-12.12 (10 μg/ml) and control IgG were then added. Cells were collected at 0, 20 minutes, 2 hours, 6 hours, 18 hours, and 26 hours. Cleaved Caspase-9, cleaved Caspase-3, cleaved PARP, and β-actin controls were detected in cell lysates by Western blot.

Briefly, it was observed that CD40L-mediated CD40 stimulation provided survival signals as it did not result in increases of cleaved Caspase-9, cleaved Caspase-3, or cleaved PARP over time, indicating that the cells were not undergoing apoptosis. However, treatment with CHIR-12.12 resulted in an increase of these cleavage products, indicating that CHIR-12.12 treatment abrogated the effects of CD40L binding on survival signaling in sCD40L-stimulated normal B cells, restoring B cell apoptosis (data not shown).

CHIR-12.12 Inhibited Expression of "Survival" Anti-Apoptotic Proteins.

In these experiments, $0.6 \times 10^6$ normal human B cells from healthy donors (percent purity between 85-95%) were stimulated with 1 μg/ml sCD40L (Alexis Corporation, Bingham, Nottinghamshire, UK). CHIR-12.12 (10 μg/ml) and control IgG were then added. Cells were collected at 0, 20 minutes, 2 hours, 6 hours, 18 hours, and 26 hours. Mcl-1, XIAP, CD40, and β-actin controls were detected in cell lysates by Western blot. Briefly, sCD40L stimulation resulted in sustained expression of Mcl-1 and XIAP over time. However, treatment of the sCD40L-stimulated cells with CHIR 12.12 resulted in a decrease in expression of these proteins overtime (data not shown). Since Mcl-1 and XIAP are "survival" signals capable of blocking the apoptotic pathway, these results demonstrate that CHIR-12.12 treatment removes the blockade against apoptosis in sCD40L-stimulated normal B cells.

CHIR-12.12 Treatment Inhibited Phosphorylation of IKKα (Ser180) and IKKβ (Ser 181) in Normal B Cells.

In these experiments, $1.0 \times 10^6$ normal human B cells from healthy donors (percent purity between 85-95%) were stimulated with 1 μg/ml sCD40L (Alexis Corporation, Bingham, Nottinghamshire, UK). CHIR-12.12 (10 μg/ml) and control IgG were then added. Cells were collected at 0 and 20 minutes. Phosphorylated IKKα (Ser180) and IKKβ (Ser 181) and total IKKβ controls were detected in cell lysates by Western blot.

Briefly, stimulation by sCD40L resulted in phosphorylation of IKKα (Ser180) and IKKβ (Ser 181) over time; however, treatment with CHIR-12.12 abrogated this response to sCD40L stimulation in normal B cells (data not shown).

CHIR-12.12 Treatment Inhibited Survival Mediated by CD40 Ligand in a Dose-Dependent Manner.

In these experiments, $0.6 \times 10^6$ normal human B cells from healthy donors percent purity between 85-95%) were stimulated with 1 μg/ml sCD40L (Alexis Corporation, Bingham, Nottinghamshire, UK). CHIR-12.12 (0.01, 0.1, 0.2, 0.5, 1.0 μg/ml) and control IgG were then added. Cells were collected at 24 hours. Cleaved PARP, and β-actin controls were detected in cell lysates by Western blot.

Briefly, CHIR-12.12 treatment resulted in increase of PARP cleavage in sCD40L stimulated cells in a dose-dependent manner and therefore abrogated the survival signaling pathway in sCD40L-stimulated normal B cells (data not shown).

CHIR-12.12 Inhibited Expression of "Survival" Anti-Apoptotic Proteins in a Dose-Dependent Manner.

In these experiments, $0.6 \times 10^6$ normal human B cells from healthy donors (percent purity between 85-95%) were stimulated with 1 μg/ml sCD40L (Alexis Corporation, Bingham, Nottinghamshire, UK). CHIR-12.12 (0.5, 2, and 10 μg/ml) and control IgG were then added. Cells were collected at 22 hours. Mcl-1, XIAP, cleaved PARP, and β-actin controls were detected in cell lysates by Western blot.

Briefly, CHIR-12.12 treatment reduced Mcl-1 and XIAP expression and increased cleaved PARP expression in sCD40L-stimulated cells in a dose-dependent manner, and thus abrogated these blockades to the apoptotic pathway in sCD40L-stimulated normal B cells (data not shown).

CHIR-12.12 Did not Affect Expression of Anti-Apoptotic Proteins, Cleaved-PARP, and XIAP, in the Absence of Soluble CD40L Signaling.

In these experiments, $1.0 \times 10^6$ normal human B cells from healthy donors (percent purity between 85-95%) were treated with CHIR-12.12 (10 μg/ml) and control IgG only (i.e., cells were not pre-stimulated with sCD40L before adding antibody). Cells were collected at 0, 4, 14, and 16 hours. XIAP, cleaved PARP, and β-actin controls were detected in cell lysates by Western blot.

Briefly, the results show that without sCD40L stimulation, the cells expressed increased concentrations of cleaved PARP, while expression of XIAP remained constant, in both IgG treated control cells and CHIR-12.12 cells (data not shown). These data indicate that CHIR-12.12 does not trigger apoptosis in normal human B cells without CD40L stimulation.

CHIR-12.12 inhibits phosphorylation of IKKα (Ser180) and IKKβ (Ser181), AKT, ERK, and p38 in normal B cells.

In these experiments, $1.0 \times 10^6$ normal human B cells from healthy donors (percent purity between 85-95%) were serum starved in 1% FBS-containing media and stimulated with 1 μg/ml sCD40L (Alexis Corporation, Bingham, Nottinghamshire, UK). The cultures were treated with CHIR-12.12 (1 and 10 μg/ml) and control IgG. Cells were collected at 0 and 20 minutes. Phospho-IKKα, phospho-IKKβ, total IKKβ, phospho-ERK, total ERK, phospho-AKT, total AKT, phospho-p38, and total p38 were detected in cell lysates by Western blot.

Briefly, sCD40L stimulation resulted in increases in IKKα/β phosphorylation, ERK phosphorylation, AKT phosphorylation, and p38 phosphorylation, thus leading to survival and or proliferation of the cells. Treatment of the cells with CHIR-12.12 abrogated the effects of sCD40L stimulation on these signaling pathways in normal B cells (data not shown).

CHIR 12.12 Inhibits Multiple Signaling Pathways Such as PI3K and MEK/ERK in the CD40 Signaling Cascade.

In these experiments, $1.0 \times 10^6$ normal human B cells from healthy donors (percent purity between 85-95%) were serum starved in 1% FBS-containing media and stimulated with 1 μg/ml sCD40L (Alexis Corporation, Bingham, Nottinghamshire, UK). The cultures were also treated with CHIR-12.12 (1 and 10 μg/ml), Wortmanin, (a PI3K/AKT inhibitor; 1 and 10 μM), LY 294002 (a PI3K/AKT inhibitor; 10 and 30 μM), and PD98095 (a MEK inhibitor; 10 and 30 μg/ml). Cells were collected at 0 and 20 minutes. Phospho-ERK, phospho-AKT, total AKT, phospho-IKKα/β, and total were detected in cell lysates by Western blot.

Briefly, the results show that CHIR-12.12 abrogated the phosphorylation of all of these signal transduction molecules, whereas the signal transduction inhibitors showed only specific abrogation of signaling, indicating that CHIR-12.12 likely inhibits upstream of these signal transduction molecules mediated by CD40L stimulation (data not shown).

CHIR-12.12 Inhibits the Binding of Signaling Molecules TRAF2 and TRAF3 to the Cytoplasmic Domain of CD40 in Normal B Cells.

In these experiments, $4.0 \times 10^6$ normal human B cells from healthy donors (percent purity between 85-95%) were serum starved for four hours in 1% FBS-containing media and stimulated with 1 µg/ml sCD40L (Alexis Corporation, Bingham, Nottinghamshire, UK) for 20 minutes. Cells were collected at 0 and 20 minutes. CD40 was immunoprecipitated using polyclonal anti-CD40 (Santa Cruz Biotechnology, CA), and was probed in a Western blot with anti-TRAF2 mAb (Santa Cruz Biotechnology, CA), anti-TRAF3 mAb (Santa Cruz Biotechnology, CA), and anti-CD40 mAb (Santa Cruz Biotechnology, CA).

Briefly, the results show that TRAF2 and TRAF3 co-precipitated with CD40 after sCD40L stimulation. In contrast, treatment with CHIR-12.12 abrogated formation of the CD40-TRAF2/3 signaling complex in sCD40L-stimulated normal B cells. There were no changes in CD40 expression (data not shown).

Without being bound by theory, the results of these experiments, and the results in the examples outlined above, indicate that the CHIR-12.12 antibody is a dual action antagonist anti-CD40 monoclonal antibody having a unique combination of attributes. This fully human monoclonal antibody blocks CD40L-mediated CD40 signaling pathways for survival and proliferation of B cells; this antagonism leads to ultimate cell death. CHIR-12.12 also mediates recognition and binding by effector cells, initiating antibody dependent cellular cytotoxicity (ADCC). Once CHIR-12.12 is bound to effector cells, cytolytic enzymes are released, leading to B-cell apoptosis and lysis. CHIR-12.12 is a more potent anti-tumor antibody than is rituximab when compared in pre-clinical tumor models.

Example 2

Evaluation of CD40 Ligand-Induced Cytokine Secretion in CD40+ Cells

Stimulation of CD40 by its ligand provides survival and proliferative signals for normal B cells. The antagonist anti-CD40 antibody CHIR-12.12 does not induce the proliferation of human peripheral blood lymphocytes but inhibits CD40L-induced lymphocyte proliferation. CD40 signaling also induces cells to produce a variety of cytokines. In this example, the ability of CHIR-12.12 to modulate cytokine production by normal B cells and monocytes was investigated.

Cells ($1 \times 10^5$ cells per well) were cultured in a 96-well plate in the presence or absence of CD40L (CD40 transfected, formaldehyde fixed CHO cells, $2 \times 10^5$ per well). Cells were incubated with huIgG1 (control) or CHIR-12.12 at 10 µg/ml at 37 C for 24 hours, and supernatants were harvested. Production of hIL-6, hIL-8, hIL-10, hTNF-α; hGM-CSF, hIL-1b, hIL-12p70, MCP-1, and MIP-1β beta was measured by Meso Scale Discovery® multi-array system (Meso Scale Discovery, Gaithersburg, Md.).

Cells cultured with CHIR-12.12 alone in the absence of CD40L did not produce any of the cytokines above background levels suggesting that CHIR-12.12 does not have an agonistic activity for cytokine production. In contrast CD40L-induced production of hIL-10, hTNF-α; hIL-8, hIL-6, MCP-1, and MIP-1β in normal B cells (n=3) (Table 2). Addition of CHIR-12.12 to these cultures inhibited production of all cytokines (see Table 3).

TABLE 2

CD40L-induced cytokine secretions from normal B cells (values are folds of induction over background).

| Cytokine | Donor 1 | Donor 2 | Donor 3 |
|---|---|---|---|
| hIL-1b | no induction | no induction | no induction |
| hIL-12p70 | no induction | ND | no induction |
| hIL-10 | 3.6 | ND | 3.6 |
| hGM-CSF | no induction | ND | no induction |
| hTNF-α | 3.7 | 4.8 | 22.8 |
| hIL-8 | 7.7 | 14.7 | 49.3 |
| hIL-6 | 5.7 | 3.8 | 20.5 |
| MCP-1 | 5.5 | not tested | 1.7 |
| MIP-1β | 2.2 | 2.6 | 17.8 |

TABLE 3

CHIR-12.12 inhibits secretion from normal B cells of all cytokines induced by CD40L (values are % inhibition).

| Cytokine | Donor 1 | Donor 2 | Donor 3 |
|---|---|---|---|
| hIL-1b | no induction | no induction | no induction |
| hIL-12p70 | no induction | ND | no induction |
| hIL-10 | 90.5 | ND | 94.4 |
| hGM-CSF | no induction | ND | no induction |
| hTNF-α | 92.8 | 97.4 | 98.5 |
| hIL-8 | 98.2 | 84.7 | 99.5 |
| hIL-6 | 92.2 | 99.9 | 99.3 |
| MCP-1 | 55.3 | not tested | 25.7 |
| MIP-1β | 54.4 | 92 | 92.5 |

CHIR-12.12 inhibited CD40L-induced monocyte production of hIL-10, hTNF-α, hIL-8, hIL-6, MCP-1, and MIP-1β (n=1) (Table 4 versus Table 5).

TABLE 4

CD40L-induced cytokine secretions from monocytes (values are folds of induction over background).

| Cytokine | Donor 1 |
|---|---|
| hIL1-b | no induction |
| hIL-12p70 | no induction |
| hIL-10 | 4.2 |
| hGM-CSF | no induction |
| hTNF-α | 13.8 |
| hIL8 | 123.5 |
| hIL6 | 77.9 |
| MCP-1 | 289.9 |
| MIP-1β | 161.9 |

TABLE 5

CHIR-12.12 inhibits secretion of all cytokines from monocytes induced by CD40L (values are % inhibition).

| Cytokine | Donor 1 |
|---|---|
| hIL-1b | no induction |
| hIL-12p70 | no induction |
| hIL-10 | 58.5 |
| hGM-CSF | no induction |
| hTNF-α | 60.1 |
| hIL-8 | 43.7 |
| hIL-6 | 64.9 |
| MCP-1 | 92.6 |
| MIP-1β | 32.4 |

Together, these data show that CHIR-12.12 is a potent antagonist for CD40-ligand mediated survival, proliferation, and cytokine production.

CD40 ligation can also induce the expression of VEGF in normal endothelial cells and monocytes (Melter et al. (2000) *Blood* 96(12):3801-3808; Flaxenburg et al. (2004) *J. Immunol.* 172:7503-7509) as well as rheumatoid synovial fibroblasts (Cho et al. (2000) *J. Immuno.* 164:5055-5061. It is believed that CD40L-mediated CD40 signaling at inflammatory sites stimulates fibroblasts and tissue monocytes/macrophage production of VEGF, leading to angiogenesis, which promotes and maintains the chronic inflammatory process (see, for example, Monaco et al. (2004) *Curr. Drug Targets Inflamm. Allergy* 3(1):35-42). As such, changes in VEGF levels may provide a useful cytokine marker of CD40L-mediated CD40 signaling. Because VEGF is a secreted protein, changes in VEGF protein expression can be easily detected in cell culture supernatants or in plasma obtained from patient blood samples using techniques such as Western blot or ELISA. Alternatively it can be detected from the mRNA obtained from cell/tissue samples, using any of a number of techniques such as Northern blot or quantitative-RT-PCR.

In another experiment, CD40L-induced production of VEGF in monocytes is examined in a manner similar to that described above. Addition of CHIR-12.12 to these cell cultures is found to inhibit CD40L-induced production of VEGF.

Example 3

Biomarkers and Prognostic Markers

The ex vivo prognostic assays and additional prognostic assays to be used in the methods of the present invention require screening biological samples for the level of expression of biomarkers whose mature protein sequences and nucleotide sequences are known in the art. See for example, the information shown in Tables 2 and 3 below. It is recognized that probes for detecting these biomarkers, either at the protein (for example, antibody probes) or nucleic acid level (for example, PCR probes), can be designed based on this sequence information, and that probes can be designed to detect variants of the sequences disclosed herein.

TABLE 6

Amino Acid and Nucleotide Sequences for Biomarkers.

| Biomarker Name | Accession No. | Accession No. |
|---|---|---|
| AKT-1 | NM_005163 | NP_005154 |
| AKT-2 | NM_001626 | NP_001617 |
| AKT-3 | AF135794 | AAD24196 |
| PI3K | Y13892 | CAA74194 |

TABLE 6-continued

Amino Acid and Nucleotide Sequences for Biomarkers.

| Biomarker Name | Accession No. | Accession No. |
|---|---|---|
| PDK1 | BC006339 | AAH06339 |
| IKKα | AF012890 | AAC51662 |
| IKKβ | AF031416 | AAC64675 |
| IκB | BT006743 | Q15653 |
| NF-κB | NM_003998 | NP_003989 |
| MEK1 | L11284 | NP_002746 |
|  | NM_002755 |  |
| MEK2 | L11285 | NP_109587 |
|  | NM_030662 |  |
| MEK3 | NM_002746 | NP_002737 |
| MEK6 | U49732 | AAB05035 |
| ERK1 | NM_002746 | NP_002737 |
| ERK2 | NM_002745 | NP_002736 |
| p38 | L35253 | AAA74301 |
| Caspase 3 | NM_004346 | NP_004337 |
| Caspase 7 | BT006683 | AAP35329 |
| Caspase 9 | BT006911 | AAP35557 |
| PARP | NM_001618 | NP_001609 |
| Bcl-2 | M14745 | AAA35591 |
| Bcl-xl | Z23115 | CAA80661 |
| Mcl-1 | AF118124 | AAD13299 |
| XIAP | U45880 | AAC50373 |
| cIAP1 | U45879 | AAC50372 |
| survivin | U75285 | AAC51660 |
| TRAF-1 | NM_005658 | NP_005649 |
| Ki67 | X65550 | CAA46519 |

TABLE 7

Amino Acid and Nucleotide Sequences for CD40 and CD40L.

| | Nucleotide Sequence | | Amino Acid Sequence | |
|---|---|---|---|---|
| Name | Accession No. | Sequence Identifier | Accession No. | Sequence Identifier |
| CD40 short isoform | NM_152854 | SEQ ID NO: 9 | NP_690593 | SEQ ID NO: 10 |
| CD40 long isoform | X60592 | SEQ ID NO: 11 | CAA43045 | SEQ ID NO: 12 |
| CD40L | NM_000074 | SEQ ID NO: 13 | NP_000065 | SEQ ID NO: 14 |
| Soluble CD40L | NM_000074 | SEQ ID NO: 15 (nucleotides 139-786 of SEQ ID NO: 13) | NP_000065 | SEQ ID NO: 16 (residues 47-261 of SEQ ID NO: 14) |

Example 4

Assays for Antagonist Activity of Anti-CD40 Therapeutic Agents

The following assays can be used to assess the antagonist activity of an anti-CD40 antibody. Human B cells for these assays can be obtained, for example, by isolation from tonsils obtained from individuals undergoing tonsillectomies, essentially as described in De Groot et al. (1990) *Lymphokine Research* (1990) 9:321. Briefly, the tissue is dispersed with scalpel blades, phagocytic and NK cells are depleted by treatment with 5 mM L-leucine methyl ester and T cells are removed by one cycle of rosetting with sheep erythrocytes (SRBC) treated with 2-aminoethyl isothiouronium bromide.

The purity of the resulting B lymphocyte preparations can be checked by indirect immunofluorescent labelling with anti-(CD20) mAb B1 (Coulter Clone, Hialeah, FA) or anti-(CD3) mAb OKT3 (Ortho, Raritan, N.J.) and a FITC-conjugated F(ab')$_2$ fragment of rabbit anti-(mouse Ig) (Zymed, San Francisco, Calif.), and FACS analysis.

B-Cell Proliferation Assay.

B cells ($4 \times 10^4$ per well) are cultured in 200 µl IMDM supplemented with 10% fetal calf serum in flat bottom 96-well microtiter plates. B cells are stimulated by addition of immobilized anti-(IgM) antibodies (Immunobeads; 5 µg/ml; BioRad, Richmond, Calif.). Where desired, 100 U/ml recombinant IL-2 is added. Varying concentrations of test monoclonal antibodies (mAbs) are added at the onset of the microcultures and proliferation is assessed at day 3 by measurement of the incorporation of ($^3$H)-thymidine after 18 hour pulsing.

An antagonist anti-CD40 antibody does not significantly costimulate human B-cell proliferation in the presence of immobilized anti-IgM or in the presence of immobilized anti-IgM and IL-2.

Banchereau-Like B-Cell Proliferation Assay.

For testing the ability of anti-CD40 monoclonal antibodies to stimulate B-cell proliferation in a culture system analogous to that described by Banchereau et al. (1991) *Science* (1991) 251:70, mouse 3T6 transfectant cells expressing the HR allelic form of human FcγRII are used. B cells ($2 \times 10^4$ per well) are cultured in flat-bottom microwells in the presence of $1 \times 10^4$ transfectant cells (irradiated with 5000 Rad) in 200 µl IMDM supplemented with 10% fetal calf serum and 100 U/ml recombinant IL-4. Before addition of the B cells, the 3T6 cells are allowed to adhere to the culture plastic for at least 5 hours. Anti-CD40 mAbs are added at concentrations varying from 15 ng/ml to 2000 ng/ml and proliferation of B cells is assessed by measurement of thymidine incorporation at day 7, upon 18 hour pulsing with [$^3$H] thymidine.

Inhibition of S2C6-Stimulated B-Cell Proliferation Using Antagonist Anti-CD40 mAbs.

Antagonist anti-CD40 monoclonal antibodies (mAbs) can also be characterized by their ability to inhibit stimulation of B-cell proliferation by an anti-CD40 antibody such as S2C6 (also known as SGN-14, which is reportedly an agonist of CD40 stimulation of proliferation of normal B cells; Francisco et al. (2000) *Cancer Res*. 60:3225-3231) using the B-cell Proliferation Assay described above. Human tonsillar B cells ($4 \times 10^4$ per well) are cultured in 200 µl in microwells in the presence of anti-IgM coupled to Sepharose beads (5 µg/ml) and anti-CD40 mAb S2C6 (1.25 µg/ml). Varying concentrations of an anti-CD40 mAb of interest are added and [$^3$H]-thymidine incorporation is assessed after 3 days. As a control anti-(glucocerebrosidase) mAb 8E4 can be added in similar concentrations. Barneveld et al. (1983) *Eur. J. Biochem*. 134:585. An antagonist anti-CD40 antibody can inhibit the costimulation of anti-IgM induced human B-cell proliferation by mAb S2C6, for example, by at least 75% or more (i.e., S2C6-stimulated proliferation in the presence of an antagonist anti-CD40 antibody is no more than 25% of that observed in the absence of the antagonist anti-CD40 antibody). In contrast, no significant inhibition would be seen with equivalent amounts of non-relevant mAb 8E4, directed to β-glucocerebrosidase. Barneveld et al., supra. Such a result would indicate that the anti-CD40 mAbs does not deliver stimulatory signals for the proliferation of human B cells, but, conversely, can inhibit stimulatory signals exerted by triggering CD40 with another mAb.

B-Cell Activation Assay with EL4B5 Cells.

Zubler et al. (1985) *J. Immunol*. (1985) 134:3662 observed that a mutant subclone of the mouse thymoma EL-4 line, known as EL4B5, could strongly stimulate B cells of both murine and human origin to proliferate and differentiate into immunoglobulin-secreting plasma cells in vitro. This activation was found to be antigen-independent and not MHC restricted. For optimal stimulation of human B cells, the presence of supernatant from activated human T cells was needed but a B-cell response also occurred when EL4B5 cells were preactivated with phorbol-12-myristate 13-acetate (PMA) or IL-1. Zubler et al. (1987) *Immunological Reviews* 99:281; and Zhang et al. (1990) *J. Immunol*. 144:2955. B-cell activation in this culture system is efficient—limiting dilution experiments have shown that the majority of human B cells can be activated to proliferate and differentiate into antibody-secreting cells. Wen et al. (1987) *Eur. J. Immunol*. 17:887.

B cells (1000 per well) are cultured together with irradiated (5000 Rad) EL4B5 cells ($5 \times 10^4$ per well) in flat bottom microtiter plates in 200 µl IMDM supplemented with 10% heat-inactivated fetal calf serum, 5 ng/ml phorbol-12-myristate 13-acetate (Sigma) and 5% human T-cell supernatant. mAbs are added at varying concentrations at the onset of the cultures and thymidine incorporation is assessed at day 6 after 18 hour pulsing with [$^3$H]-thymidine. For the preparation of T-cell supernatant, purified T cells are cultured at a density of $10^6$/ml for 36 hours in the presence of 1 µg/ml PHA and 10 ng/ml PMA. Wen et al. (1987) *Eur. J. Immunol*. (1987) 17:887. T-cell supernatant is obtained by centrifugation of the cells and stored at −20° C. The effectiveness of T-cell supernatants in enhancing proliferation of human B cells in EL4B5-B cell cultures is tested and the most effective supernatants are pooled for use in experiments. When assessing the effect of an anti-CD40 antibody on EL4B5-induced human B-cell proliferation, a monoclonal antibody such as MOPC-141 (IgG2b) can be added as a control.

An antagonist anti-CD40 antibody can inhibit B-cell proliferation stimulated by the EL4B5 cell line, for example, by at least 75% or more (i.e., EL4B5-induced B cell proliferation in the presence of an antagonist anti-CD40 antibody is no more than 25% of that observed in the absence of the antagonist anti-CD40 antibody). In contrast, a control antibody such as MOPC-141 would have no significant effect on EL4B5-induced B cell proliferation.

Human T Cell Helper Assay for Antibody Production by B Cells.

An antagonist anti-CD40 antibody can function as an antagonist of immunoglobulin production by B cells. An anti-CD40 antibody can be tested for this type of antagonist activity by assessing the antibody's ability to inhibit immunoglobulin production by B cells that have been stimulated in a contact-dependent manner with activated T cells in a T cell helper assay. In this manner, 96-well tissue culture plates are coated with a 1:500 dilution of ascites fluid of anti-CD3 mAb CLB-T3/3 (CLB, Amsterdam, The Netherlands). As indicated costimulatory mAbs are added: anti CD2 mAbs CLB-T11.1/1 and CLB-T11.2/1 (CLB, Amsterdam, The Netherlands), both ascites 1:1000 and anti-CD28 mAb CLB-28/1 (CLB, Amsterdam, The Netherlands). Subsequently, tonsillar T cells (irradiated, 3000 Rad; $10^5$ per well), tonsillar B cells ($10^4$ per well), and rIL-2 (20 U/ml) are added. The final volume of each cell culture is 200 µl. After 8 days, cells are spun down, and cell-free supernatant is harvested. The concentrations of human IgM and IgG in (diluted) samples is estimated by ELISA as described below.

In one embodiment, human tonsillar B cells (104/well) are cultured together with irradiated purified T cells (3000 rad, $10^5$/well) in 96-well plates, coated with anti-CD3 mAb and with or without different mAbs to costimulate the T cells. After 8 days of culture the supernatants are harvested for the determination of immunoglobulin production by the B cells. Immunoglobulin production by the B cells is assessed by the ELISA assay described below. The anti-CD40 antibody of interest is added in varying concentrations from the onset of the cultures. As a control, mAb MOPC-141 can be added.

An antagonist anti-CD40 antibody can inhibit IgG and IgM antibody production of B cells stimulated by human T cells by at least 50% or more (i.e., T cell-induced antibody production by B cells in the presence of an antagonist anti-CD40 antibody is no more than 50% of that observed in the absence of the antagonist anti-CD40 antibody). In contrast, a control antibody such as MOPC-141 would have no significant effect on T cell-induced antibody production by B cells.

ELISA Assay for Immunoglobulin Quantification.

The concentrations of human IgM and IgG are estimated by ELISA. 96-well ELISA plates are coated with 4 µg/ml mouse anti-human IgG mAb MH 16-01 (CLB, Amsterdam, The Netherlands) or with 1.2 µg/ml mouse anti-human IgM mAb 4102 (Tago, Burlingame, Calif.) in 0.05 M carbonate buffer (pH=9.6), by incubation for 16 h at 4° C. Plates are washed 3 times with PBS-0.05% Tween-20 (PBS-Tween) and saturated with BSA for 1 hour. After 2 washes the plates are incubated for 1 h at 37° C. with different dilutions of the test samples. After 3 washes, bound Ig is detected by incubation for 1 h at 37° C. with 1 µg/ml peroxidase-labeled mouse anti-human IgG mAb MH 16-01 (CLB) or mouse anti-human IgM mAb MH 15-01 (CLB). Plates are washed 4 times and bound peroxidase activity is revealed by the addition of O-phenylenediamine as a substrate. Human standard serum (H00, CLB) is used to establish a standard curve for each assay.

Example 5

CHIR-12.12 Treatment Blocks CD40 Ligand-Mediated CD40 Survival and Signaling Pathways in Normal Human B Cells The activation of CD40 by CD40 ligand (CD40L) can regulate the survival, proliferation, and differentiation of normal B lymphocytes. In B cells, ligation of CD40 leads to its binding with tumor necrosis factor receptor-associated factors (TRAFs) and the subsequent activation of multiple downstream signaling pathways involved in cellular proliferation and survival. The activation of this pathway can be demonstrated ex vivo, where addition of CD40L to cultured normal B cells promotes their survival and proliferation. The additional study described below was undertaken to further characterize the effects of the CHIR-12.12 monoclonal antibody on CD40L-mediated CD40 survival and signaling pathways in normal human B cells.

Normal human B cells were purified from peripheral blood by negative selection using the MACS B cell isolation kit II (Miltenyi Biotech INC, Auburn, Calif.) and cultured for 24 hr with or without 2 µg/ml of recombinant human soluble CD40L (rhsCD40L) in the presence of 10 µg/ml of CHIR-12.12 or isotype control hIgG1. Cells were lysed and whole cell lysates resolved by SDS-PAGE and Western blotting using antibodies specific to human cPARP, Mcl-1, Bcl-xl, p-Akt, and p-p38 MAPK. All membranes were stripped and re-probed for either β-actin or total Akt or p38 MAPK protein, as appropriate. Results are shown in FIG. 1.

CD40L stimulation of normal human B cells decreased the levels of the apoptotic marker (cPARP) and increased expression of anti-apoptotic markers (Mcl-1, Bcl-xl), thus inducing proliferation/survival of these cells. Additionally, CD40L-induced B-cell survival was associated with the phosphorylation of Akt and p38 MAPK. In contrast, CHIR-12.12 treatment of CD40L-stimulated normal B cells ex vivo inhibited the expression of the anti-apoptotic proteins Mcl-1 and Bcl-xl, as well as inhibiting the phosphorylation of the downstream signaling proteins, ultimately leading to B-cell apoptosis.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A method for identifying a subject having an inflammatory disease or autoimmune disease that is responsive to treatment with an anti-CD40 therapeutic agent, said method comprising:
   a) providing a test biological sample obtained from said subject and a control biological sample obtained from said subject, wherein said test biological sample and said control biological sample comprise CD40-expressing cells that have been stimulated with a CD40 ligand;
   b) contacting said test biological sample with an effective amount of said anti-CD40 therapeutic agent;
   c) detecting the level of at least one biomarker in said test biological sample, wherein said biomarker is selected from the group consisting of:
      (i) a biomarker of cellular apoptosis, wherein said biomarker of apoptosis is selected from the group consisting of a cleaved Caspase protein, cleaved poly ADP-ribose polymerase (PARP), cell surface expression of phosphotidylserine (PS), genomic DNA fragmentation, and any combinations thereof;
      (ii) a biomarker of a CD40L-mediated CD40 signaling pathway, wherein said biomarker of said CD40L-mediated CD40 signaling pathway is selected from the group consisting of phospho-PI3K, phospho-PDK1, phospho-AKT, phospho-MEK, phospho-ERK, phospho-p38, phospho-IKKa/β, phospho-IKB protein, and activated NF-KB;
      (iii) and a biomarker of cell survival, wherein said biomarker of cell survival is selected from the group consisting of an anti-apoptotic protein that is a Bcl-2 family member, an IAP apoptosis inhibitor protein, and TNF receptor-associated factor-1 (TRAF-1); and
   d) comparing the level of said at least one biomarker in said test biological sample to the level of said at least one biomarker detected in said control biological sample, wherein said control biological sample has not been contacted with said anti-CD40 therapeutic agent, wherein
      (i) at least a 20% increase in the level of at least one of said biomarkers of apoptosis, and/or
      (ii) at least a 25% reduction in the level of at least one of said biomarkers of at least one of said CD40L-mediated CD40 signaling pathways, and/or
      (iii) at least a 25% reduction in the level of at least one of said biomarkers of cell survival
   in said test biological sample relative to said control biological sample is indicative of a subject who would benefit from treatment with said anti-CD40 therapeutic agent;

wherein said anti-CD40 therapeutic agent is an antagonist anti-CD40 monoclonal antibody that is capable of specifically binding to a human CD40 antigen expressed on the surface of a human B cell, said monoclonal antibody being free of significant agonist activity when bound to the CD40 antigen expressed on the surface of said B cell, wherein said anti-CD40 monoclonal antibody is selected from the group consisting of:
  a) a monoclonal antibody comprising a light chain variable domain containing the complementarity determining region (CDR) residues of SEQ ID NO:2 and a heavy chain variable domain containing the CDR residues of SEQ ID NO:4;
  b) a monoclonal antibody comprising a light chain variable domain containing the CDR residues of SEQ ID NO:2 and a heavy chain variable domain containing the CDR residues of SEQ ID NO:5;
  c) a monoclonal antibody comprising a light chain variable domain containing the CDR residues of SEQ ID NO:6 and a heavy chain variable domain containing the CDR residues of SEQ ID NO:7;
  d) a monoclonal antibody comprising a light chain variable domain containing the CDR residues of SEQ ID NO:6 and a heavy chain variable domain containing the CDR residues of SEQ ID NO:8; and
  e) a monoclonal antibody that is an antigen-binding fragment of a monoclonal antibody of any one of preceding items a)-j), wherein said fragment retains the capability of specifically binding to said human CD40 antigen.

2. The method of claim 1, wherein said CD40-expressing cells were stimulated ex vivo with a ligand of CD40 prior to said contacting step.

3. The method of claim 2, wherein said ligand of CD40 is selected from the group consisting of soluble CD40L and membrane-bound CD40L.

4. The method of claim 1, wherein said fragment is selected from the group consisting of a Fab fragment, an F(ab')$_2$ fragment, an Fv fragment, and a single-chain Fv fragment.

5. The method of claim 1, wherein said cleaved Caspase protein is selected from the group consisting of cleaved Caspase-3, cleaved Caspase-7, and cleaved Caspase-9.

6. The method of claim 1, wherein cell surface PS is detected by annexin V staining and wherein genomic DNA fragmentation is detected by TUNEL staining.

7. The method of claim 1, wherein said Bcl-2 family member is selected from the group consisting of Bcl-xl and Mcl-1.

8. The method of claim 1, wherein said IAP apoptosis inhibitor protein is selected from the group consisting of survivin, XIAP, and cIAP1.

9. The method of claim 1, further comprising detecting in said test biological sample and said control biological sample the level of at least one cytokine marker of CD40 signaling.

10. The method of claim 9, wherein said cytokine marker is selected from the group consisting of vascular endothelial growth factor (VEGF), interleukin (IL)-6, IL-8, IL-10, granulocyte monocyte colony-stimulating factor (GM-CSF), tumor necrosis factor-α (TNF-α), monocyte chemoattractant protein-1 (MCP-1), and macrophage inflammatory protein-1β (MIP-1β).

11. The method of claim 9, wherein a reduction in the level of at least one of said cytokine markers in said test biological sample relative to said control biological sample is indicative of a subject who would benefit from treatment with said anti-CD40 therapeutic agent.

12. The method of claim 1, wherein said anti-CD40 therapeutic agent is an anti-CD40 monoclonal antibody that specifically binds to a human CD40 antigen expressed on the surface of a CD40-expressing cell, thereby modulating antibody-dependent cell-mediated cytotoxicity (ADCC) activity, and wherein said biomarker is said biomarker of apoptosis.

13. The method of claim 12, wherein said cleaved caspase protein is selected from the group consisting of cleaved Caspase-3, cleaved Caspase-7, and cleaved Caspase-9.

14. The method of claim 12, wherein cell surface PS is detected by annexin V staining and wherein genomic DNA fragmentation is detected by TUNEL staining.

15. The method of claim 1, wherein said inflammatory disease or autoimmune disease is selected from the group consisting of systemic lupus erythematosus (SLE), discoid lupus, lupus nephritis, sarcoidosis, juvenile arthritis, rheumatoid arthritis, psoriatic arthritis, Reiter's syndrome, ankylosing spondylitis, gouty arthritis, rejection of an organ or tissue transplant, graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hashimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, sarcoidosis, Type I and Type II diabetes mellitus, type 1, 2, 3, and 4 delayed-type hypersensitivity, allergy or allergic disorders, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, and chronic inflammatory demyelinating polyneuropathy.

16. The method of claim 1, further comprising detecting in a biological sample of said subject the level of expression of cell-surface CD40, the level of expression of cell-surface CD40L, or both, on CD40-expressing cells within said biological sample.

17. The method of claim 1, further comprising detecting the level of circulating soluble CD40 or circulating soluble CD40L in a biological sample collected from subject.

18. The method of claim 1, wherein detecting the level of said biomarker comprises using an antibody to detect biomarker protein expression.

19. The method of claim 1, wherein detecting the level of said biomarker comprises nucleic acid hybridization.

20. The method of claim 1, wherein detecting the level of said biomarker comprises performing quantitative RT-PCR.

21. A method of treating a subject having an inflammatory disease or autoimmune disease that is associated with CD40-expressing cells, said method comprising screening said patient with a method according to claim 1, and then treating said subject with said anti-CD40 therapeutic agent when said method according to any one of claims 1 through 35 generates a result that is indicative of a positive treatment outcome with said anti-CD40 therapeutic agent.

22. A method for monitoring efficacy of an anti-CD40 therapeutic agent in treatment of a subject for an inflammatory disease or autoimmune disease that is associated with CD40-expressing cells, said method comprising:
  a) obtaining a baseline biological sample from said subject prior to administering a dose of said anti-CD40 therapeutic agent, wherein said baseline biological sample comprises CD40-expressing cells;

b) detecting the level of at least one biomarker in said baseline biological sample, wherein said biomarker is selected from the group consisting of:
  (i) a biomarker of cellular apoptosis, wherein said biomarker of apoptosis is selected from the group consisting of a cleaved Caspase protein, cleaved poly ADP-ribose polymerase (PARP), cell surface expression of phosphotidylserine (PS), genomic DNA fragmentation, and any combinations thereof;
  (ii) a biomarker of a CD40L-mediated CD40 signaling pathway, wherein said biomarker of said CD40L-mediated CD40 signaling pathway is selected from the group consisting of phospho-PI3K, phospho-PDK1, phospho-AKT, phospho-MEK, phospho-ERK, phospho-p38, phospho-IKKα/β, phospho-IKB protein, and activated NF-κB;
  (iii) and a biomarker of cell survival, wherein said biomarker of cell survival is selected from the group consisting of an anti-apoptotic protein that is a Bcl-2 family member, an IAP apoptosis inhibitor protein, and TNF receptor-associated factor-1 (TRAF-1);
c) administering said anti-CD40 therapeutic agent to said subject;
d) obtaining from said subject at least one subsequent biological sample;
e) detecting the level of said at least one biomarker in said at least one subsequent sample; and
f) comparing the level of said at least one biomarker in said at least one subsequent sample with the level of said at least one biomarker in said baseline biological sample wherein
  (i) at least a 20% increase in the level of at least one of said biomarkers of apopotosis, and/or
  (ii) at least a 25% reduction in the level of at least one of said biomarkers of at least one of said CD40L-mediated CD40 signaling pathways, and/or
  (iii) at least a 25% reduction in the level of at least one of said biomarkers of cell survival
within said subsequent biological sample relative to said baseline biological sample is indicative of efficacy of treatment with said anti-CD40 therapeutic agent;
  wherein said anti-CD40 therapeutic agent is an antagonist anti-CD40 monoclonal antibody that is capable of specifically binding to a human CD40 antigen expressed on the surface of a human B cell, said monoclonal antibody being free of significant agonist activity when bound to the CD40 antigen expressed on the surface of said B cell, wherein said anti-CD40 monoclonal antibody is selected from the group consisting of:
  a) a monoclonal antibody comprising a light chain variable domain containing the complementarity determining region (CDR) residues of SEQ ID NO:2 and a heavy chain variable domain containing the CDR residues of SEQ ID NO:4;
  b) a monoclonal antibody comprising a light chain variable domain containing the CDR residues of SEQ ID NO:2 and a heavy chain variable domain containing the CDR residues of SEQ ID NO:5;
  c) a monoclonal antibody comprising a light chain variable domain containing the CDR residues of SEQ ID NO:6 and a heavy chain variable domain containing the CDR residues of SEQ ID NO:7;
  d) a monoclonal antibody comprising a light chain variable domain containing the CDR residues of SEQ ID NO:6 and a heavy chain variable domain containing the CDR residues of SEQ ID NO:8; and
  e) a monoclonal antibody that is an antigen-binding fragment of a monoclonal antibody of any one of preceding items a)-j), wherein said fragment retains the capability of specifically binding to said human CD40 antigen.

23. The method of claim 22, wherein a single dose of said anti-CD40 therapeutic agent is administered to said subject.

24. The method of claim 22, wherein multiple doses of said anti-CD40 therapeutic agent are administered to said subject.

25. The method of claim 22, wherein said fragment is selected from the group consisting of a Fab fragment, an F(ab')$_2$ fragment, an Fv fragment, and a single-chain Fv fragment.

26. The method of claim 22, wherein said cleaved Caspase protein is selected from the group consisting of cleaved Caspase-3, cleaved Caspase-7, and cleaved Caspase-9.

27. The method of claim 22, wherein cell surface PS is detected by annexin V staining and wherein genomic DNA fragmentation is detected by TUNEL staining.

28. The method of claim 22, wherein said Bcl-2 family member is selected from the group consisting of Bcl-xl and Mcl-1.

29. The method of claim 22, wherein said IAP apoptosis inhibitor protein is selected from the group consisting of survivin, XIAP, and cIAP1.

30. The method of claim 22, further comprising detecting in said subsequent biological sample and said baseline biological sample the level of at least one cytokine marker of CD40 signaling.

31. The method of claim 30, wherein said cytokine marker is selected from the group consisting of vascular endothelial growth factor (VEGF), interleukin (IL)-6, IL-8, IL-10, granulocyte monocyte colony-stimulating factor (GM-CSF), tumor necrosis factor-α (TNF-a), monocyte chemoattractant protein-1 (MCP-1), and macrophage inflammatory protein-1β (MIP-1β).

32. The method of claim 30, wherein a reduction in the level of at least one of said cytokine markers in said subsequent biological sample relative to said baseline biological sample is indicative of efficacy of treatment with said anti-CD40 therapeutic agent.

33. The method of claim 22, wherein said anti-CD40 therapeutic agent is an anti-CD40 monoclonal antibody that specifically binds to a human CD40 antigen expressed on the surface of a CD40-expressing cell, thereby modulating antibody-dependent cell-mediated cytotoxity (ADCC), and wherein said biomarker is said biomarker of apoptosis.

34. The method of claim 33, wherein said biomarker of apoptosis is selected from the group consisting of a cleaved caspase protein, cleaved poly ADP-ribose polymerase (PARP), cell surface expression of phosphotidylserine (PS), genomic DNA fragmentation, and any combinations thereof.

35. The method of claim 34, wherein said cleaved caspase protein is selected from the group consisting of cleaved Caspase-3, cleaved Caspase-7, and cleaved Caspase-9.

36. The method of claim 34, wherein cell surface PS is detected by annexin V staining and wherein genomic DNA fragmentation is detected by TUNEL staining.

37. The method of claim 22, wherein said inflammatory disease or autoimmune disease is selected from the group consisting of systemic lupus erythematosus (SLE), discoid lupus, lupus nephritis, sarcoidosis, juvenile arthritis, rheumatoid arthritis, psoriatic arthritis, Reiter's syndrome, ankylosing spondylitis, gouty arthritis, rejection of an organ or tissue transplant, graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hashimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, sarcoidosis, Type I and Type II diabetes mellitus, type 1, 2, 3, and 4 delayed-type hypersensitivity, allergy or allergic disorders, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, and chronic inflammatory demyelinating polyneuropathy.

38. The method of claim 22, further comprising detecting in said subsequent biological sample and said baseline biological sample the level of expression of at least one CD40-related factor selected from the group consisting of cell-surface CD40, cell-surface CD40L, and both cell-surface CD40 and cell-surface CD40L on CD40-expressing cells within said subsequent and baseline biological samples, wherein a reduction in the level of expression of at least one of said CD40-related factors within said subsequent biological sample relative to said baseline biological sample is indicative of efficacy of treatment with said anti-CD40 therapeutic agent.

39. The method of claim 22, further comprising collecting from said subject a baseline sample of blood or a blood component and a subsequent sample of blood or said blood component, and detecting the level of circulating soluble CD40 or circulating soluble CD40L in said baseline sample and said subsequent sample, wherein a reduction in the level of expression of at least one of said circulating soluble CD40 or circulating soluble CD40L within said subsequent sample relative to said baseline sample is indicative of efficacy of treatment with said anti-CD40 therapeutic agent.

40. The method of claim 1, wherein said antagonist anti-CD40 monoclonal antibody is a monoclonal antibody comprising an amino acid sequence selected from the group consisting of:
  (i) SEQ ID NO:2;
  (ii) SEQ ID NO:4;
  (iii) SEQ ID NO:5;
  (iv) SEQ ID NO:2 and SEQ ID NO:4; and
  (v) SEQ ID NO:2 and SEQ ID NO:5
  (vi) SEQ ID NO:6;
  (vii) SEQ ID NO:7;
  (viii) SEQ ID NO:8;
  (ix) SEQ ID NO:6 and SEQ ID NO:7; and
  (x) SEQ ID NO:6 and SEQ ID NO:8.

41. The method of claim 1, wherein said antagonist anti-CD40 antibody is selected from the group consisting of:
  (i) a monoclonal antibody comprising the variable and constant region sequences shown in SEQ ID NO:2;
  (ii) a monoclonal antibody comprising the variable and constant region sequences shown in SEQ ID NO:4;
  (iii) a monoclonal antibody comprising the variable and constant region sequences shown in SEQ ID NO:5;
  (iv) a monoclonal antibody comprising the variable and constant region sequences shown in SEQ ID NO:2 and the variable and constant region sequences shown SEQ ID NO:4;
  (v) a monoclonal antibody comprising the variable and constant region sequences shown in SEQ ID NO:2 and the variable and constant region sequences shown SEQ ID NO:5;
  (vi) a monoclonal antibody comprising the variable and constant region sequences shown in SEQ ID NO:6;
  (vii) a monoclonal antibody comprising the variable and constant region sequences shown in SEQ ID NO:7;
  (viii) a monoclonal antibody comprising the variable and constant region sequences shown in SEQ ID NO:8;
  (ix) a monoclonal antibody comprising the variable and constant region sequences shown in SEQ ID NO:6 and the variable and constant region sequences shown SEQ ID NO:7; and
  (x) a monoclonal antibody comprising the variable and constant region sequences shown in SEQ ID NO:6 and the variable and constant region sequences shown SEQ ID NO:8.

42. The method of claim 1, wherein said antagonist anti-CD40 antibody is selected from the group consisting of the antibody CHIR-5.9 produced by the hybridoma cell line deposited with the ATCC as Patent Deposit No. PTA-5542 and the antibody CHIR-12.12 produced by the hybridoma cell line deposited with the ATCC as Patent Deposit No. PTA-5543.

43. The method of claim 12, wherein said antagonist anti-CD40 monoclonal antibody is a monoclonal antibody comprising an amino acid sequence selected from the group consisting of:
  (i) SEQ ID NO:2;
  (ii) SEQ ID NO:4;
  (iii) SEQ ID NO:5;
  (iv) SEQ ID NO:2 and SEQ ID NO:4; and
  (vi) SEQ ID NO:2 and SEQ ID NO:5
  (vi) SEQ ID NO:6;
  (vii) SEQ ID NO:7;
  (viii) SEQ ID NO:8;
  (ix) SEQ ID NO:6 and SEQ ID NO:7; and
  (x) SEQ ID NO:6 and SEQ ID NO:8.

44. The method of claim 12, wherein said antagonist anti-CD40 antibody is selected from the group consisting of:
  (i) a monoclonal antibody comprising the variable and constant region sequences shown in SEQ ID NO:2;
  (ii) a monoclonal antibody comprising the variable and constant region sequences shown in SEQ ID NO:4;
  (iii) a monoclonal antibody comprising the variable and constant region sequences shown in SEQ ID NO:5;
  (iv) a monoclonal antibody comprising the variable and constant region sequences shown in SEQ ID NO:2 and the variable and constant region sequences shown SEQ ID NO:4; and
  (v) a monoclonal antibody comprising the variable and constant region sequences shown in SEQ ID NO:2 and the variable and constant region sequences shown SEQ ID NO:5;
  (vi) a monoclonal antibody comprising the variable and constant region sequences shown in SEQ ID NO:6;
  (vii) a monoclonal antibody comprising the variable and constant region sequences shown in SEQ ID NO:7;
  (viii) a monoclonal antibody comprising the variable and constant region sequences shown in SEQ ID NO:8;
  (ix) a monoclonal antibody comprising the variable and constant region sequences shown in SEQ ID NO:6 and the variable and constant region sequences shown SEQ ID NO:7; and (x) a monoclonal antibody comprising the variable and constant region sequences shown in SEQ ID NO:6 and the variable and constant region sequences shown SEQ ID NO:8.

45. The method of claim 12, wherein said antagonist anti-CD40 antibody is selected from the group consisting of the antibody CHIR-5.9 produced by the hybridoma cell line deposited with the ATCC as Patent Deposit No. PTA-5542 and the antibody CHIR-12.12 produced by the hybridoma cell line deposited with the ATCC as Patent Deposit No. PTA-5543.

46. The method of claim 22, wherein said antagonist anti-CD40 monoclonal antibody is a monoclonal antibody comprising an amino acid sequence selected from the group consisting of:
  (i) SEQ ID NO:2;
  (ii) SEQ ID NO:4;
  (iii) SEQ ID NO:5;
  (iv) SEQ ID NO:2 and SEQ ID NO:4; and
  (vii) SEQ ID NO:2 and SEQ ID NO:5
  (vi) SEQ ID NO:6;
  (vii) SEQ ID NO:7;
  (viii) SEQ ID NO:8;
  (ix) SEQ ID NO:6 and SEQ ID NO:7; and
  (x) SEQ ID NO:6 and SEQ ID NO:8.

47. The method of claim 22, wherein said antagonist anti-CD40 antibody is selected from the group consisting of:
  (i) a monoclonal antibody comprising the variable and constant region sequences shown in SEQ ID NO:2;
  (ii) a monoclonal antibody comprising the variable and constant region sequences shown in SEQ ID NO:4;
  (iii) a monoclonal antibody comprising the variable and constant region sequences shown in SEQ ID NO:5;
  (iv) a monoclonal antibody comprising the variable and constant region sequences shown in SEQ ID NO:2 and the variable and constant region sequences shown SEQ ID NO:4;
  (v) a monoclonal antibody comprising the variable and constant region sequences shown in SEQ ID NO:2 and the variable and constant region sequences shown SEQ ID NO:5.
  (vi) a monoclonal antibody comprising the variable and constant region sequences shown in SEQ ID NO:6;
  (vii) a monoclonal antibody comprising the variable and constant region sequences shown in SEQ ID NO:7;
  (viii) a monoclonal antibody comprising the variable and constant region sequences shown in SEQ ID NO:8;
  (ix) a monoclonal antibody comprising the variable and constant region sequences shown in SEQ ID NO:6 and the variable and constant region sequences shown SEQ ID NO:7; and
  (x) a monoclonal antibody comprising the variable and constant region sequences shown in SEQ ID NO:6 and the variable and constant region sequences shown SEQ ID NO:8.

48. The method of claim 22, wherein said antagonist anti-CD40 antibody is selected from the group consisting of the antibody CHIR-5.9 produced by the hybridoma cell line deposited with the ATCC as Patent Deposit No. PTA-5542 and the antibody CHIR-12.12 produced by the hybridoma cell line deposited with the ATCC as Patent Deposit No. PTA-5543.

49. The method of claim 33, wherein said antagonist anti-CD40 monoclonal antibody is a monoclonal antibody comprising an amino acid sequence selected from the group consisting of:
  (i) SEQ ID NO:2;
  (ii) SEQ ID NO:4;
  (iii) SEQ ID NO:5;
  (iv) SEQ ID NO:2 and SEQ ID NO:4; and
  (viii) SEQ ID NO:2 and SEQ ID NO:5
  (vi) SEQ ID NO:6;
  (vii) SEQ ID NO:7;
  (viii) SEQ ID NO:8;
  (ix) SEQ ID NO:6 and SEQ ID NO:7; and
  (x) SEQ ID NO:6 and SEQ ID NO:8.

50. The method of claim 33, wherein said antagonist anti-CD40 antibody is selected from the group consisting of:
  (i) a monoclonal antibody comprising the variable and constant region sequences shown in SEQ ID NO:2;
  (ii) a monoclonal antibody comprising the variable and constant region sequences shown in SEQ ID NO:4;
  (iii) a monoclonal antibody comprising the variable and constant region sequences shown in SEQ ID NO:5;
  (iv) a monoclonal antibody comprising the variable and constant region sequences shown in SEQ ID NO:2 and the variable and constant region sequences shown SEQ ID NO:4;
  (v) a monoclonal antibody comprising the variable and constant region sequences shown in SEQ ID NO:2 and the variable and constant region sequences shown SEQ ID NO:5;
  (vi) a monoclonal antibody comprising the variable and constant region sequences shown in SEQ ID NO:6;
  (vii) a monoclonal antibody comprising the variable and constant region sequences shown in SEQ ID NO:7;
  (viii) a monoclonal antibody comprising the variable and constant region sequences shown in SEQ ID NO:8;
  (ix) a monoclonal antibody comprising the variable and constant region sequences shown in SEQ ID NO:6 and the variable and constant region sequences shown SEQ ID NO:7; and
  (x) a monoclonal antibody comprising the variable and constant region sequences shown in SEQ ID NO:6 and the variable and constant region sequences shown SEQ ID NO:8.

51. The method of claim 33, wherein said antagonist anti-CD40 antibody is selected from the group consisting of the antibody CHIR-5.9 produced by the hybridoma cell line deposited with the ATCC as Patent Deposit No. PTA-5542 and the antibody CHIR-12.12 produced by the hybridoma cell line deposited with the ATCC as Patent Deposit No. PTA-5543.

* * * * *

UNITED STATES PATENT AND TRADEMARK OFFICE
CERTIFICATE OF CORRECTION

PATENT NO. : 8,333,970 B2
APPLICATION NO. : 11/914710
DATED : December 18, 2012
INVENTOR(S) : Aukerman et al.

It is certified that error appears in the above-identified patent and that said Letters Patent is hereby corrected as shown below:

IN THE SPECIFICATION
Column 20, line 17, delete "at," and insert --al,-- therefor.
Column 35, line 44, delete "calorimetric" and insert --colorimetric-- therefor.

IN THE CLAIMS
In Claim 21, at Column 98, line 57, delete "any one of claims 1 through 35" and insert --claim 1-- therefor.
In Claim 40, at Column 101, line 48, at the end of item (iv), delete "and."
In Claim 40, at Column 101, line 49, at the end of item (v), insert --;--.
In Claim 43, at Column 102, line 35, at the end of item (iv), delete "and".
In Claim 43, at Column 102, line 36, delete "(vi)" and insert --(v)-- therefor.
In Claim 43, at Column 102, at the end of line 36, insert --;--.
In Claim 44, at Column 102, line 53, at the end of item (iv), delete "and".
In Claim 46, at Column 103, line 19, at the end of item (iv), delete "and".
In Claim 46, at Column 103, line 20, delete "(vii)" and insert --(v)-- therefor.
In Claim 46, at Column 103, at the end of line 20, insert --;--.
In Claim 47, at Column 103, line 41, at the end of item (v), insert --;--.
In Claim 49, at Column 104, line 13, at the end of item (iv), delete "and".
In Claim 49, at Column 104, line 14, delete "(viii)" and insert --(v)-- therefor.
In Claim 49, at Column 104, at the end of line 14, insert --;--.

Signed and Sealed this
Twenty-third Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO.         : 8,333,970 B2
APPLICATION NO.    : 11/914710
DATED              : December 18, 2012
INVENTOR(S)        : Schoenenberger Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1042 days.

Signed and Sealed this
Twenty-second Day of October, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,333,970 B2 | Page 1 of 1 |
| APPLICATION NO. | : 11/914710 | |
| DATED | : December 18, 2012 | |
| INVENTOR(S) | : Aukerman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1042 days.

This certificate supersedes the Certificate of Correction issued October 22, 2013.

Signed and Sealed this
Twenty-fifth Day of March, 2014

Michelle K. Lee
*Deputy Director of the United States Patent and Trademark Office*

SEQUENCE LISTING

```
<160> NUMBER OF SEQ ID NOS: 16

<210> SEQ ID NO 1
<211> LENGTH: 720
<212> TYPE: DNA
<213> ORGANISM: Artificial Sequence
<220> FEATURE:
<223> OTHER INFORMATION: Coding sequence for light chain of 12.12 human
      anti-CD40 antibody
<221> NAME/KEY: CDS
<222> LOCATION: (1)...(720)

<400> SEQUENCE: 1 atg gcg ctc cct gct cag ctc ctg ggg ctg cta atg ctc tgg gtc tct      48
Met Ala Leu Pro Ala Gln Leu Leu Gly Leu Leu Met Leu Trp Val Ser
 1               5                  10                  15 gga tcc agt ggg gat att gtg atg act cag tct cca ctc tcc ctg acc      96
```

```
Gly Ser Ser Gly Asp Ile Val Met Thr Gln Ser Pro Leu Ser Leu Thr
            20                  25                  30 gtc acc cct gga gag ccg gcc tcc atc tcc tgc agg tcc agt cag agc      144
Val Thr Pro Gly Glu Pro Ala Ser Ile Ser Cys Arg Ser Ser Gln Ser
        35                  40                  45 ctc ctg tat agt aat gga tac aac tat ttg gat tgg tac ctg cag aag      192
Leu Leu Tyr Ser Asn Gly Tyr Asn Tyr Leu Asp Trp Tyr Leu Gln Lys
    50                  55                  60 cca ggg cag tct cca cag gtc ctg atc tct ttg ggt tct aat cgg gcc      240
Pro Gly Gln Ser Pro Gln Val Leu Ile Ser Leu Gly Ser Asn Arg Ala
65                  70                  75                  80 tcc ggg gtc cct gac agg ttc agt ggc agt gga tca ggc aca gat ttt      288
Ser Gly Val Pro Asp Arg Phe Ser Gly Ser Gly Ser Gly Thr Asp Phe
                85                  90                  95 aca ctg aaa atc agc aga gtg gag gct gag gat gtt ggg gtt tat tac      336
Thr Leu Lys Ile Ser Arg Val Glu Ala Glu Asp Val Gly Val Tyr Tyr
            100                 105                 110 tgc atg caa gct cga caa act cca ttc act ttc ggc cct ggg acc aaa      384
Cys Met Gln Ala Arg Gln Thr Pro Phe Thr Phe Gly Pro Gly Thr Lys
        115                 120                 125 gtg gat atc aga cga act gtg gct gca cca tct gtc ttc atc ttc ccg      432
Val Asp Ile Arg Arg Thr Val Ala Ala Pro Ser Val Phe Ile Phe Pro
    130                 135                 140 cca tct gat gag cag ttg aaa tct gga act gcc tct gtt gtg tgc ctg      480
Pro Ser Asp Glu Gln Leu Lys Ser Gly Thr Ala Ser Val Val Cys Leu
145                 150                 155                 160 ctg aat aac ttc tat ccc aga gag gcc aaa gta cag tgg aag gtg gat      528
Leu Asn Asn Phe Tyr Pro Arg Glu Ala Lys Val Gln Trp Lys Val Asp
                165                 170                 175 aac gcc ctc caa tcg ggt aac tcc cag gag agt gtc aca gag cag gac      576
Asn Ala Leu Gln Ser Gly Asn Ser Gln Glu Ser Val Thr Glu Gln Asp
            180                 185                 190 agc aag gac agc acc tac agc ctc agc agc acc ctg acg ctg agc aaa      624
Ser Lys Asp Ser Thr Tyr Ser Leu Ser Ser Thr Leu Thr Leu Ser Lys
        195                 200                 205 gca gac tac gag aaa cac aaa gtc tac gcc tgc gaa gtc acc cat cag      672
Ala Asp Tyr Glu Lys His Lys Val Tyr Ala Cys Glu Val Thr His Gln
    210                 215                 220 ggc ctg agc tcg ccc gtc aca aag agc ttc aac agg gga gag tgt tag      720
Gly Leu Ser Ser Pro Val Thr Lys Ser Phe Asn Arg Gly Glu Cys  *
225                 230                 235

<210> SEQ ID NO 2
<211> LENGTH: 239
<212> TYPE: PRT
<213> ORGANISM: Artificial Sequence
<220> FEATURE:
<223> OTHER INFORMATION: Coding sequence for light chain of 12.12 human
      anti-CD40 antibody

<400> SEQUENCE: 2

Met Ala Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Thr
            20                  25                  30

Val Thr Pro Gly Glu Pro Ala Ser Ile Ser Cys Arg Ser Ser Gln Ser
        35                  40                  45

Leu Leu Tyr Ser Asn Gly Tyr Asn Tyr Leu Asp Trp Tyr Leu Gln Lys
    50                  55                  60

Pro Gly Gln Ser Pro Gln Val Leu Ile Ser Leu Gly Ser Asn Arg Ala
65                  70                  75                  80
```

```
Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Arg Gln Thr Pro Phe Thr Phe Gly Pro Gly Thr Lys
        115                 120                 125

Val Asp Ile Arg Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 3
<211> LENGTH: 2016
<212> TYPE: DNA
<213> ORGANISM: Artificial Sequence
<220> FEATURE:
<223> OTHER INFORMATION: Coding sequence for heavy chain of 12.12 human
      anti-CD40 antibody (with introns)

<400> SEQUENCE: 3
atggagtttg ggctgagctg ggttttcctt gttgctattt taagaggtgt ccagtgtcag      60
gtgcagttgg tggagtctgg gggaggcgtg gtccagcctg gaggtccct gagactctcc     120 tgtgcagcct ctggattcac cttcagtagc tatggcatgc actgggtccg ccaggctcca    180 ggcaagggc tggagtgggt ggcagttata tcatatgagg aaagtaatag ataccatgca    240
gactccgtga agggccgatt caccatctcc agagacaatt ccaagatcac gctgtatctg    300
caaatgaaca gcctcagaac tgaggacacg gctgtgtatt actgtgcgag agatgggggt    360
atagcagcac tgggcctga ctactggggc cagggaaccc tggtcaccgt ctcctcagca    420
agtaccaagg gcccatccgt cttccccctg gcgcccgcta gcaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagagagt tggtgagagg    720
ccagcacagg gagggagggt gtctgctgga agccaggctc agcgctcctg cctggacgca    780
tcccggctat gcagtcccag tccagggcag caaggcaggc cccgtctgcc tcttcacccg    840
gaggcctctg cccgcccac tcatgctcag ggagagggtc ttctggcttt ttccccaggc    900
tctgggcagg cacaggctag gtgcccctaa cccaggccct gcacacaaag ggcaggtgc    960 tgggctcaga cctgccaaga gccatatccg gaggaccct gccctgacc taagcccacc    1020 ccaaaggcca aactctccac tccctcagct cggacacctt ctctcctccc agattccagt    1080
aactcccaat cttctctctg cagagcccaa atcttgtgac aaaactcaca catgcccacc    1140
```

```
gtgcccaggt aagccagccc aggcctcgcc ctccagctca aggcgggaca ggtgccctag    1200
agtagcctgc atccagggac aggccccagc cgggtgctga cacgtccacc tccatctctt    1260
cctcagcacc tgaactcctg ggggaccgt cagtcttcct cttccccca aacccaagg      1320 acaccctcat gatctcccgg acccctgagg tcacatgcgt ggtggtggac gtgagccacg   1380
aagaccctga ggtcaagttc aactggtacg tggacggcgt ggaggtgcat aatgccaaga   1440
caaagccgcg ggaggagcag tacaacagca cgtaccgtgt ggtcagcgtc ctcaccgtcc   1500
tgcaccagga ctggctgaat ggcaaggagt acaagtgcaa ggtctccaac aaagccctcc   1560
cagcccccat cgagaaaacc atctccaaag ccaaaggtgg acccgtgggg gtgcgagggc   1620
cacatggaca gaggccggct cggcccaccc tctgccctga gagtgaccgc tgtaccaacc   1680
tctgtcccta cagggcagcc ccgagaacca caggtgtaca ccctgccccc atcccgggag   1740
gagatgacca agaaccaggt cagcctgacc tgcctggtca aaggcttcta tcccagcgac   1800
atcgccgtgg agtgggagag caatgggcag ccggagaaca actacaagac cacgcctccc   1860
gtgctggact ccgacggctc cttcttcctc tatagcaagc tcaccgtgga caagagcagg   1920
tggcagcagg ggaacgtctt ctcatgctcc gtgatgcatg aggctctgca caaccactac   1980
acgcagaaga gcctctccct gtctccgggt aaatga                             2016
```

<210> SEQ ID NO 4
<211> LENGTH: 469
<212> TYPE: PRT
<213> ORGANISM: Artificial Sequence
<220> FEATURE:
<223> OTHER INFORMATION: Heavy chain of 12.12 human anti-CD40 antibody

<400> SEQUENCE: 4

```
Met Glu Phe Gly Leu Ser Trp Val Phe Leu Val Ala Ile Leu Arg Gly
  1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser Ser Tyr Gly Met His Trp Val Arg Gln Ala Pro Gly Lys Gly Leu
     50                  55                  60

Glu Trp Val Ala Val Ile Ser Tyr Glu Glu Ser Asn Arg Tyr His Ala
 65                  70                  75                  80

Asp Ser Val Lys Gly Arg Phe Thr Ile Ser Arg Asp Asn Ser Lys Ile
                 85                  90                  95

Thr Leu Tyr Leu Gln Met Asn Ser Leu Arg Thr Glu Asp Thr Ala Val
            100                 105                 110

Tyr Tyr Cys Ala Arg Asp Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
```

```
                    210                 215                 220
Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                    245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460

Leu Ser Pro Gly Lys
465

<210> SEQ ID NO 5
<211> LENGTH: 469
<212> TYPE: PRT
<213> ORGANISM: Artificial Sequence
<220> FEATURE:
<223> OTHER INFORMATION: Heavy chain of variant of 12.12 human anti-CD40
      antibody

<400> SEQUENCE: 5

Met Glu Phe Gly Leu Ser Trp Val Phe Leu Val Ala Ile Leu Arg Gly
 1               5                  10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
    50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
```

```
                100                 105                 110
Tyr Tyr Cys Ala Arg Asp Gly Ile Ala Ala Pro Gly Pro Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 6
<211> LENGTH: 239
<212> TYPE: PRT
<213> ORGANISM: Artificial Sequence
<220> FEATURE:
<223> OTHER INFORMATION: Light chain of 5.9 human anti-CD40 antibody

<400> SEQUENCE: 6
```

Met Ala Leu Leu Ala Gln Leu Leu Gly Leu Met Leu Trp Val Pro
1               5                   10                  15

Gly Ser Ser Gly Ala Ile Val Met Thr Gln Pro Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Asn Trp Leu Gln Gln Arg
    50                  55                  60

Pro Gly Gln Pro Pro Arg Leu Leu Ile Tyr Lys Phe Phe Arg Arg Leu
65                  70                  75                  80

Ser Gly Val Pro Asp Arg Phe Ser Gly Ser Gly Ala Gly Thr Asp Phe
                85                  90                  95

Thr Leu Lys Ile Ser Arg Val Glu Ala Glu Asp Val Gly Val Tyr Tyr
            100                 105                 110

Cys Met Gln Val Thr Gln Phe Pro His Thr Phe Gly Gln Gly Thr Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 7
<211> LENGTH: 474
<212> TYPE: PRT
<213> ORGANISM: Artificial Sequence
<220> FEATURE:
<223> OTHER INFORMATION: Heavy chain of 5.9 human anti-CD40 antibody

<400> SEQUENCE: 7

Met Gly Ser Thr Ala Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Gly Thr Ala Ala Gly Arg Asp Tyr Tyr Tyr Tyr
        115                 120                 125

```
Tyr Gly Met Asp Val Trp Gly Gln Gly Thr Thr Val Thr Val Ser Ser
            130                 135                 140

Ala Ser Thr Lys Gly Pro Ser Val Phe Pro Leu Ala Pro Ala Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Leu Gly Thr Gln Thr
            210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 8
<211> LENGTH: 474
<212> TYPE: PRT
<213> ORGANISM: Artificial Sequence
<220> FEATURE:
<223> OTHER INFORMATION: Heavy chain of variant of 5.9 human anti-CD40
      antibody

<400> SEQUENCE: 8

Met Gly Ser Thr Ala Ile Leu Ala Leu Leu Leu Ala Val Leu Gln Gly
1               5                   10                  15
```

Val Cys Ala Glu Val Gln Leu Val Gln Ser Gly Ala Glu Val Lys Lys
    20                  25                  30

Pro Gly Glu Ser Leu Lys Ile Ser Cys Lys Gly Ser Gly Tyr Ser Phe
            35                  40                  45

Thr Ser Tyr Trp Ile Gly Trp Val Arg Gln Met Pro Gly Lys Gly Leu
50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Gly Thr Ala Ala Gly Arg Asp Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

```
Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 9
<211> LENGTH: 612
<212> TYPE: DNA
<213> ORGANISM: Homo sapiens
<220> FEATURE:
<221> NAME/KEY: CDS
<222> LOCATION: (1)...(612)
<221> NAME/KEY: misc_feature
<222> LOCATION: (0)...(0)
<223> OTHER INFORMATION: Coding sequence for short isoform of human CD40

<400> SEQUENCE: 9 atg gtt cgt ctg cct ctg cag tgc gtc ctc tgg ggc tgc ttg ctg acc      48
Met Val Arg Leu Pro Leu Gln Cys Val Leu Trp Gly Cys Leu Leu Thr
  1               5                  10                  15 gct gtc cat cca gaa cca ccc act gca tgc aga gaa aaa cag tac cta      96
Ala Val His Pro Glu Pro Pro Thr Ala Cys Arg Glu Lys Gln Tyr Leu
             20                  25                  30 ata aac agt cag tgc tgt tct ttg tgc cag cca gga cag aaa ctg gtg     144
Ile Asn Ser Gln Cys Cys Ser Leu Cys Gln Pro Gly Gln Lys Leu Val
         35                  40                  45 agt gac tgc aca gag ttc act gaa acg gaa tgc ctt cct tgc ggt gaa     192
Ser Asp Cys Thr Glu Phe Thr Glu Thr Glu Cys Leu Pro Cys Gly Glu
     50                  55                  60 agc gaa ttc cta gac acc tgg aac aga gag aca cac tgc cac cag cac     240
Ser Glu Phe Leu Asp Thr Trp Asn Arg Glu Thr His Cys His Gln His
 65                  70                  75                  80 aaa tac tgc gac ccc aac cta ggg ctt cgg gtc cag cag aag ggc acc     288
Lys Tyr Cys Asp Pro Asn Leu Gly Leu Arg Val Gln Gln Lys Gly Thr
                 85                  90                  95 tca gaa aca gac acc atc tgc acc tgt gaa gaa ggc tgg cac tgt acg     336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc     384
Ser Glu Ala Cys Glu Ser Cys Val Leu His Arg Ser Cys Ser Pro Gly
        115                 120                 125 ttt ggg gtc aag cag att gct aca ggg gtt tct gat acc atc tgc gag     432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa     480
Pro Cys Pro Val Gly Phe Phe Ser Asn Val Ser Ser Ala Phe Glu Lys
145                 150                 155                 160 tgt cac cct tgg aca agg tcc cca gga cga gct gag agc cct ggt ggt     528
Cys His Pro Trp Thr Arg Ser Pro Gly Arg Ala Glu Ser Pro Gly Gly
                165                 170                 175 gat ccc cat cat ctt cgg gat cct gtt tgc cat cct ctt ggt gct ggt     576
Asp Pro His His Leu Arg Asp Pro Val Cys His Pro Leu Gly Ala Gly
            180                 185                 190 ctt tat caa aaa ggt ggc caa gaa gcc aac caa taa                     612
Leu Tyr Gln Lys Gly Gly Gln Glu Ala Asn Gln *
        195                 200

<210> SEQ ID NO 10
<211> LENGTH: 203
<212> TYPE: PRT
<213> ORGANISM: Homo sapiens

<400> SEQUENCE: 10
```

```
Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
             20                  25                  30

Ile Asn Ser Gln Cys Cys Ser Leu Cys Gln Pro Gly Gln Lys Leu Val
         35                  40                  45

Ser Asp Cys Thr Glu Phe Thr Glu Thr Glu Cys Leu Pro Cys Gly Glu
 50                  55                  60

Ser Glu Phe Leu Asp Thr Trp Asn Arg Glu Thr His Cys His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Arg Ser Pro Gly Ser Ala Glu Ser Pro Gly Gly
                165                 170                 175

Asp Pro His His Leu Arg Asp Pro Val Cys His Pro Leu Gly Ala Gly
            180                 185                 190

Leu Tyr Gln Lys Gly Gly Gln Glu Ala Asn Gln
            195                 200
```

```
<210> SEQ ID NO 11
<211> LENGTH: 834
<212> TYPE: DNA
<213> ORGANISM: Homo sapiens
<220> FEATURE:
<221> NAME/KEY: CDS
<222> LOCATION: (1)...(834)
<221> NAME/KEY: misc_feature
<222> LOCATION: (0)...(0)
<223> OTHER INFORMATION: Coding sequence for long isoform of human CD40

<400> SEQUENCE: 11
```

```
atg gtt cgt ctg cct ctg cag tgc gtc ctc tgg ggc tgc ttg ctg acc      48
Met Val Arg Leu Pro Leu Gln Cys Val Leu Trp Gly Cys Leu Leu Thr
 1               5                  10                  15 gct gtc cat cca gaa cca ccc act gca tgc aga gaa aaa cag tac cta      96
Ala Val His Pro Glu Pro Pro Thr Ala Cys Arg Glu Lys Gln Tyr Leu
             20                  25                  30 ata aac agt cag tgc tgt tct ttg tgc cag cca gga cag aaa ctg gtg     144
Ile Asn Ser Gln Cys Cys Ser Leu Cys Gln Pro Gly Gln Lys Leu Val
         35                  40                  45 agt gac tgc aca gag ttc act gaa acg gaa tgc ctt cct tgc ggt gaa     192
Ser Asp Cys Thr Glu Phe Thr Glu Thr Glu Cys Leu Pro Cys Gly Glu
 50                  55                  60 agc gaa ttc cta gac acc tgg aac aga gag aca cac tgc cac cag cac     240
Ser Glu Phe Leu Asp Thr Trp Asn Arg Glu Thr His Cys His Gln His
 65                  70                  75                  80 aaa tac tgc gac ccc aac cta ggg ctt cgg gtc cag cag aag ggc acc     288
Lys Tyr Cys Asp Pro Asn Leu Gly Leu Arg Val Gln Gln Lys Gly Thr
                 85                  90                  95 tca gaa aca gac acc atc tgc acc tgt gaa gaa ggc tgg cac tgt acg     336
Ser Glu Thr Asp Thr Ile Cys Thr Cys Glu Glu Gly Trp His Cys Thr
```

```
agt gag gcc tgt gag agc tgt gtc ctg cac cgc tca tgc tcg ccc ggc    384
Ser Glu Ala Cys Glu Ser Cys Val Leu His Arg Ser Cys Ser Pro Gly
            115                 120                 125 ttt ggg gtc aag cag att gct aca ggg gtt tct gat acc atc tgc gag    432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa    480
Pro Cys Pro Val Gly Phe Phe Ser Asn Val Ser Ser Ala Phe Glu Lys
145                 150                 155                 160 tgt cac cct tgg aca agc tgt gag acc aaa gac ctg gtt gtg caa cag    528
Cys His Pro Trp Thr Ser Cys Glu Thr Lys Asp Leu Val Val Gln Gln
                165                 170                 175 gca ggc aca aac aag act gat gtt gtc tgt ggt ccc cag gat cgg ctg    576
Ala Gly Thr Asn Lys Thr Asp Val Val Cys Gly Pro Gln Asp Arg Leu
            180                 185                 190 aga gcc ctg gtg gtg atc ccc atc atc ttc ggg atc ctg ttt gcc atc    624
Arg Ala Leu Val Val Ile Pro Ile Ile Phe Gly Ile Leu Phe Ala Ile
    195                 200                 205 ctc ttg gtg ctg gtc ttt atc aaa aag gtg gcc aag aag cca acc aat    672
Leu Leu Val Leu Val Phe Ile Lys Lys Val Ala Lys Lys Pro Thr Asn
210                 215                 220 aag gcc ccc cac ccc aag cag gaa ccc cag gag atc aat ttt ccc gac    720
Lys Ala Pro His Pro Lys Gln Glu Pro Gln Glu Ile Asn Phe Pro Asp
225                 230                 235                 240 gat ctt cct ggc tcc aac act gct gct cca gtg cag gag act tta cat    768
Asp Leu Pro Gly Ser Asn Thr Ala Ala Pro Val Gln Glu Thr Leu His
                245                 250                 255 gga tgc caa ccg gtc acc cag gag gat ggc aaa gag agt cgc atc tca    816
Gly Cys Gln Pro Val Thr Gln Glu Asp Gly Lys Glu Ser Arg Ile Ser
            260                 265                 270 gtg cag gag aga cag tga                                            834
Val Gln Glu Arg Gln *
    275

<210> SEQ ID NO 12
<211> LENGTH: 277
<212> TYPE: PRT
<213> ORGANISM: Homo sapiens

<400> SEQUENCE: 12

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140
```

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
            165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 13
<211> LENGTH: 786
<212> TYPE: DNA
<213> ORGANISM: Homo sapiens
<220> FEATURE:
<221> NAME/KEY: CDS
<222> LOCATION: (1)...(786)
<221> NAME/KEY: misc_feature
<222> LOCATION: (0)...(0)
<223> OTHER INFORMATION: CD40L

<400> SEQUENCE: 13

| | |
|---|---|
| atg atc gaa aca tac aac caa act tct ccc cga tct gcg gcc act gga<br>Met Ile Glu Thr Tyr Asn Gln Thr Ser Pro Arg Ser Ala Ala Thr Gly<br>1               5                   10                  15 | 48 |
| ctg ccc atc agc atg aaa att ttt atg tat tta ctt act gtt ttt ctt<br>Leu Pro Ile Ser Met Lys Ile Phe Met Tyr Leu Leu Thr Val Phe Leu<br>                20                  25                  30 | 96 |
| atc acc cag atg att ggg tca gca ctt ttt gct gtg tat ctt cat aga<br>Ile Thr Gln Met Ile Gly Ser Ala Leu Phe Ala Val Tyr Leu His Arg<br>            35                  40                  45 | 144 |
| agg ttg gac aag ata gaa gat gaa agg aat ctt cat gaa gat ttt gta<br>Arg Leu Asp Lys Ile Glu Asp Glu Arg Asn Leu His Glu Asp Phe Val<br>        50                  55                  60 | 192 |
| ttc atg aaa acg ata cag aga tgc aac aca gga gaa aga tcc tta tcc<br>Phe Met Lys Thr Ile Gln Arg Cys Asn Thr Gly Glu Arg Ser Leu Ser<br>65                  70                  75                  80 | 240 |
| tta ctg aac tgt gag gag att aaa agc cag ttt gaa ggc ttt gtg aag<br>Leu Leu Asn Cys Glu Glu Ile Lys Ser Gln Phe Glu Gly Phe Val Lys<br>                85                  90                  95 | 288 |
| gat ata atg tta aac aaa gag gag acg aag aaa gaa aac agc ttt gaa<br>Asp Ile Met Leu Asn Lys Glu Glu Thr Lys Lys Glu Asn Ser Phe Glu<br>            100                 105                 110 | 336 |
| atg caa aaa ggt gat cag aat cct caa att gcg gca cat gtc ata agt<br>Met Gln Lys Gly Asp Gln Asn Pro Gln Ile Ala Ala His Val Ile Ser<br>        115                 120                 125 | 384 |
| gag gcc agc agt aaa aca aca tct gtg tta cag tgg gct gaa aaa gga<br>Glu Ala Ser Ser Lys Thr Thr Ser Val Leu Gln Trp Ala Glu Lys Gly<br>    130                 135                 140 | 432 |
| tac tac acc atg agc aac aac ttg gta acc ctg gaa aat ggg aaa cag<br>Tyr Tyr Thr Met Ser Asn Asn Leu Val Thr Leu Glu Asn Gly Lys Gln | 480 |

```
ctg acc gtt aaa aga caa gga ctc tat tat atc tat gcc caa gtc acc     528
Leu Thr Val Lys Arg Gln Gly Leu Tyr Tyr Ile Tyr Ala Gln Val Thr
                165                 170                 175 ttc tgt tcc aat cgg gaa gct tcg agt caa gct cca ttt ata gcc agc     576
Phe Cys Ser Asn Arg Glu Ala Ser Ser Gln Ala Pro Phe Ile Ala Ser
            180                 185                 190 ctc tgc cta aag tcc ccc ggt aga ttc gag aga atc tta ctc aga gct     624
Leu Cys Leu Lys Ser Pro Gly Arg Phe Glu Arg Ile Leu Leu Arg Ala
        195                 200                 205 gca aat acc cac agt tcc gcc aaa cct tgc ggg caa caa tcc att cac     672
Ala Asn Thr His Ser Ser Ala Lys Pro Cys Gly Gln Gln Ser Ile His
    210                 215                 220 ttg gga gga gta ttt gaa ttg caa cca ggt gct tcg gtg ttt gtc aat     720
Leu Gly Gly Val Phe Glu Leu Gln Pro Gly Ala Ser Val Phe Val Asn
225                 230                 235                 240 gtg act gat cca agc caa gtg agc cat ggc act ggc ttc acg tcc ttt     768
Val Thr Asp Pro Ser Gln Val Ser His Gly Thr Gly Phe Thr Ser Phe
                245                 250                 255 ggc tta ctc aaa ctc tga                                             786
Gly Leu Leu Lys Leu *
            260

<210> SEQ ID NO 14
<211> LENGTH: 261
<212> TYPE: PRT
<213> ORGANISM: Homo sapiens

<400> SEQUENCE: 14

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220
```

```
Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 15
<211> LENGTH: 648
<212> TYPE: DNA
<213> ORGANISM: Homo sapiens
<220> FEATURE:
<221> NAME/KEY: CDS
<222> LOCATION: (1)...(648)
<221> NAME/KEY: misc_feature
<222> LOCATION: (0)...(0)
<223> OTHER INFORMATION: Soluble CD40L

<400> SEQUENCE: 15 cat aga agg ttg gac aag ata gaa gat gaa agg aat ctt cat gaa gat      48
His Arg Arg Leu Asp Lys Ile Glu Asp Glu Arg Asn Leu His Glu Asp
 1               5                  10                  15 ttt gta ttc atg aaa acg ata cag aga tgc aac aca gga gaa aga tcc      96
Phe Val Phe Met Lys Thr Ile Gln Arg Cys Asn Thr Gly Glu Arg Ser
                20                  25                  30 tta tcc tta ctg aac tgt gag gag att aaa agc cag ttt gaa ggc ttt     144
Leu Ser Leu Leu Asn Cys Glu Glu Ile Lys Ser Gln Phe Glu Gly Phe
            35                  40                  45 gtg aag gat ata atg tta aac aaa gag gag acg aag aaa gaa aac agc     192
Val Lys Asp Ile Met Leu Asn Lys Glu Glu Thr Lys Lys Glu Asn Ser
 50                  55                  60 ttt gaa atg caa aaa ggt gat cag aat cct caa att gcg gca cat gtc     240
Phe Glu Met Gln Lys Gly Asp Gln Asn Pro Gln Ile Ala Ala His Val
 65                  70                  75                  80 ata agt gag gcc agc agt aaa aca aca tct gtg tta cag tgg gct gaa     288
Ile Ser Glu Ala Ser Ser Lys Thr Thr Ser Val Leu Gln Trp Ala Glu
                85                  90                  95 aaa gga tac tac acc atg agc aac aac ttg gta acc ctg gaa aat ggg     336
Lys Gly Tyr Tyr Thr Met Ser Asn Asn Leu Val Thr Leu Glu Asn Gly
            100                 105                 110 aaa cag ctg acc gtt aaa aga caa gga ctc tat tat atc tat gcc caa     384
Lys Gln Leu Thr Val Lys Arg Gln Gly Leu Tyr Tyr Ile Tyr Ala Gln
        115                 120                 125 gtc acc ttc tgt tcc aat cgg gaa gct tcg agt caa gct cca ttt ata     432
Val Thr Phe Cys Ser Asn Arg Glu Ala Ser Ser Gln Ala Pro Phe Ile
    130                 135                 140 gcc agc ctc tgc cta aag tcc ccc ggt aga ttc gag aga atc tta ctc     480
Ala Ser Leu Cys Leu Lys Ser Pro Gly Arg Phe Glu Arg Ile Leu Leu
145                 150                 155                 160 aga gct gca aat acc cac agt tcc gcc aaa cct tgc ggg caa caa tcc     528
Arg Ala Ala Asn Thr His Ser Ser Ala Lys Pro Cys Gly Gln Gln Ser
                165                 170                 175 att cac ttg gga gga gta ttt gaa ttg caa cca ggt gct tcg gtg ttt     576
Ile His Leu Gly Gly Val Phe Glu Leu Gln Pro Gly Ala Ser Val Phe
            180                 185                 190 gtc aat gtg act gat cca agc caa gtg agc cat ggc act ggc ttc acg     624
Val Asn Val Thr Asp Pro Ser Gln Val Ser His Gly Thr Gly Phe Thr
        195                 200                 205 tcc ttt ggc tta ctc aaa ctc tga                                     648
Ser Phe Gly Leu Leu Lys Leu *
    210                 215
```

```
<210> SEQ ID NO 16
<211> LENGTH: 215
<212> TYPE: PRT
<213> ORGANISM: Homo sapiens

<400> SEQUENCE: 16

His Arg Arg Leu Asp Lys Ile Glu Asp Glu Arg Asn Leu His Glu Asp
 1               5                  10                  15

Phe Val Phe Met Lys Thr Ile Gln Arg Cys Asn Thr Gly Glu Arg Ser
            20                  25                  30

Leu Ser Leu Leu Asn Cys Glu Glu Ile Lys Ser Gln Phe Glu Gly Phe
        35                  40                  45

Val Lys Asp Ile Met Leu Asn Lys Glu Glu Thr Lys Lys Glu Asn Ser
 50                  55                  60

Phe Glu Met Gln Lys Gly Asp Gln Asn Pro Gln Ile Ala Ala His Val
 65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
            100                 105                 110

Lys Gln Leu Thr Val Lys Arg Gln Gly Leu Tyr Tyr Ile Tyr Ala Gln
        115                 120                 125

Val Thr Phe Cys Ser Asn Arg Glu Ala Ser Ser Gln Ala Pro Phe Ile
130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
        195                 200                 205

Ser Phe Gly Leu Leu Lys Leu
210                 215
```